(12) United States Patent
Yu et al.

(10) Patent No.: US 11,702,657 B2
(45) Date of Patent: Jul. 18, 2023

(54) TRNA/PRE-MIRNA COMPOSITIONS AND METHODS FOR TREATING HEPATOCELLULAR CARCINOMA

(71) Applicant: The Regents of the University of California, Oakland, CA (US)

(72) Inventors: Aiming Yu, Sacramento, CA (US); Joseph L Jilek, Davis, CA (US); Qianyu Zhang, Davis, CA (US); Pui Yan Ho, Davis, CA (US); Meijuan Tu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 252 days.

(21) Appl. No.: 17/048,466

(22) PCT Filed: Apr. 19, 2019

(86) PCT No.: PCT/US2019/028331
§ 371 (c)(1),
(2) Date: Oct. 16, 2020

(87) PCT Pub. No.: WO2019/204733
PCT Pub. Date: Oct. 24, 2019

(65) Prior Publication Data
US 2021/0087564 A1 Mar. 25, 2021

Related U.S. Application Data

(60) Provisional application No. 62/660,919, filed on Apr. 20, 2018.

(51) Int. Cl.
| | | |
|---|---|---|
| *C12N 15/113* | (2010.01) | |
| *A61P 35/00* | (2006.01) | |
| *C12N 15/115* | (2010.01) | |

(52) U.S. Cl.
CPC ............ *C12N 15/113* (2013.01); *A61P 35/00* (2018.01); *C12N 15/115* (2013.01); *C12N 2310/141* (2013.01); *C12N 2310/16* (2013.01); *C12N 2310/3519* (2013.01)

(58) Field of Classification Search
None
See application file for complete search history.

(56) References Cited

U.S. PATENT DOCUMENTS

| | | | | |
|---|---|---|---|---|
| 10,422,003 | B2* | 9/2019 | Yu | C12Q 1/6876 |
| 10,619,156 | B2* | 4/2020 | Yu | C12N 15/111 |
| 11,041,201 | B2* | 6/2021 | Yu | C12N 15/115 |
| 2009/0004668 | A1 | 1/2009 | Chen et al. | |
| 2009/0298920 | A1 | 3/2009 | Dardel et al. | |
| 2018/0237772 | A1* | 8/2018 | Yu | C12N 15/11 |
| 2018/0245152 | A1* | 8/2018 | Yu | C12Q 1/6876 |

FOREIGN PATENT DOCUMENTS

| | | |
|---|---|---|
| CN | 108753780 | 11/2018 |
| CN | 109022442 | 12/2018 |
| WO | 2015183667 | 3/2015 |
| WO | WO 2016153880 | 9/2016 |
| WO | WO 2019226603 | 11/2019 |

OTHER PUBLICATIONS

Chen et al (2015) "A General Approach to High-Yield Biosynthesis of Chimeric RNAs Bearing Various Types of Functional Small RNAs for Broad Applications" Nucleic Acids Research, 43(7):3857-3869.
Ewe et al. (2016) "Liposome-polyethylenimine complexes (DPPC-PEI lipopolyplexes) for therapeutic siRNA delivery in vivo" Nanomedicine: Nanotechnology, Biology, And Medicine, 13(1):209-218.
Ho et al. (2016) "Bioengineering of Noncoding RNAs for Research Agents and Therapeutics: Bioengineering of ncRNAs" Wiley Interdisciplinary Reviews: RNA, 7(2):186-197.
Ho et al. (2018) "Bioengineered Noncoding RNAs Selectively Change Cellular miRNome Profiles for Cancer Therapy" Journal of Pharmacology and Experimental Therapeutics, 365(3):494-506.
Jilek et al. (2019) "Bioengineered Let-7c Inhibits Orthotopic Hepatocellular Carcinoma and Improves Overall Survival with Minimal Immunogenicity" Molecular Therapy-Nucleic Acids, 14:498-508.
Shimizu et al. (2010) "The Let-7 Family of MicrorRNAs Inhibits Bcl-xL Expression and Potentiates Sorafenib-Induced Apoptosis in Human Hepatocellular Carcinoma" Journal of Hepatology, 52:5.
Wang et al. (2015) "Bioengineering Novel Chimeric microRNA-34a for Prodrug Cancer Therapy: High-Yield Expression and Purification, and Structural and Functional Characterization" Journal of Pharmacology and Experimental Therapeutics, 354(2):131-141.
Farra et al. (2015) "Therapeutic potential of small interfering RNAs/micro interfering RNA in hepatocellular carcinoma" World Journal of Gastroenterology, 21(30):8994-9001.
Scherer et al. (2007) "Optimization and characterization of tRNA-shRNA expression constructs" Nucleic Acids Research, 35(8):2620-2628.

* cited by examiner

*Primary Examiner* — Brian Whiteman
(74) *Attorney, Agent, or Firm* — Brian E. Davy; Bozicevic, Field & Francis LLP

(57) ABSTRACT

Provided are hybrid tRNA/pre-microRNA and tRNA molecules and their use in methods of preventing and treating hepatocellular carcinoma (HCC). In some embodiments, provided are polynucleotides that include a tRNA operably linked to one or more pre-microRNA (pre-miRNA), where the tRNA and/or pre-miRNA are operably linked to one or more inserted RNA molecules that inhibit the growth or proliferation of a hepatocellular carcinoma (HCC) cell.

17 Claims, 32 Drawing Sheets
Specification includes a Sequence Listing.

| Huh7 | | | |
|---|---|---|---|
| RNA Agent | EC50 (nM) | Hill slope | R2 |
| MSA | 116.1±8.28 | 1.00 | 0.86 |
| miR-298 | 4.34±1.12* | 0.47±0.06 | 0.98 |
| miR-124 | 1.13±1.16* | 0.52±0.10 | 0.98 |
| let-7c | 0.51±1.25* | 0.73±0.39 | 0.94 |
| miR-328 | 0.81±1.14* | 0.56±0.26 | 0.86 |
| miR-126 | 1.67±1.25 | 0.46±0.13 | 0.94 |
| miR-144 | 25.41±2.21 | 1.00 | 0.92 |

| Sk-Hep-1 | | | |
|---|---|---|---|
| RNA Agent | EC50 (nM) | Hill slope | R2 |
| MSA | 63.01±1.69 | 0.27±0.05 | 0.80 |
| miR-298 | 11.28±1.24* | 0.34±0.04 | 0.93 |
| miR-124 | 1.41±1.16* | 0.37±0.03 | 0.97 |
| let-7c | 0.78±1.20* | 0.39±0.03 | 0.96 |
| miR-328 | 0.87±1.29 | 0.43±0.05 | 0.93 |
| miR-126 | 3.18±1.23* | 0.35±0.04 | 0.94 |
| miR-144 | 89.17±1.43 | 0.34±0.05 | 0.90 |

Secondary Tumorspheres

Size:
98.35±5.11 nm

PDI: 0.227±0.019

Zeta Potential:
43.9±2.2 mV

Size:
102.4±5.9 nm

PDI: 0.245±0.012

Zeta Potential:
45.1±1.2 mV

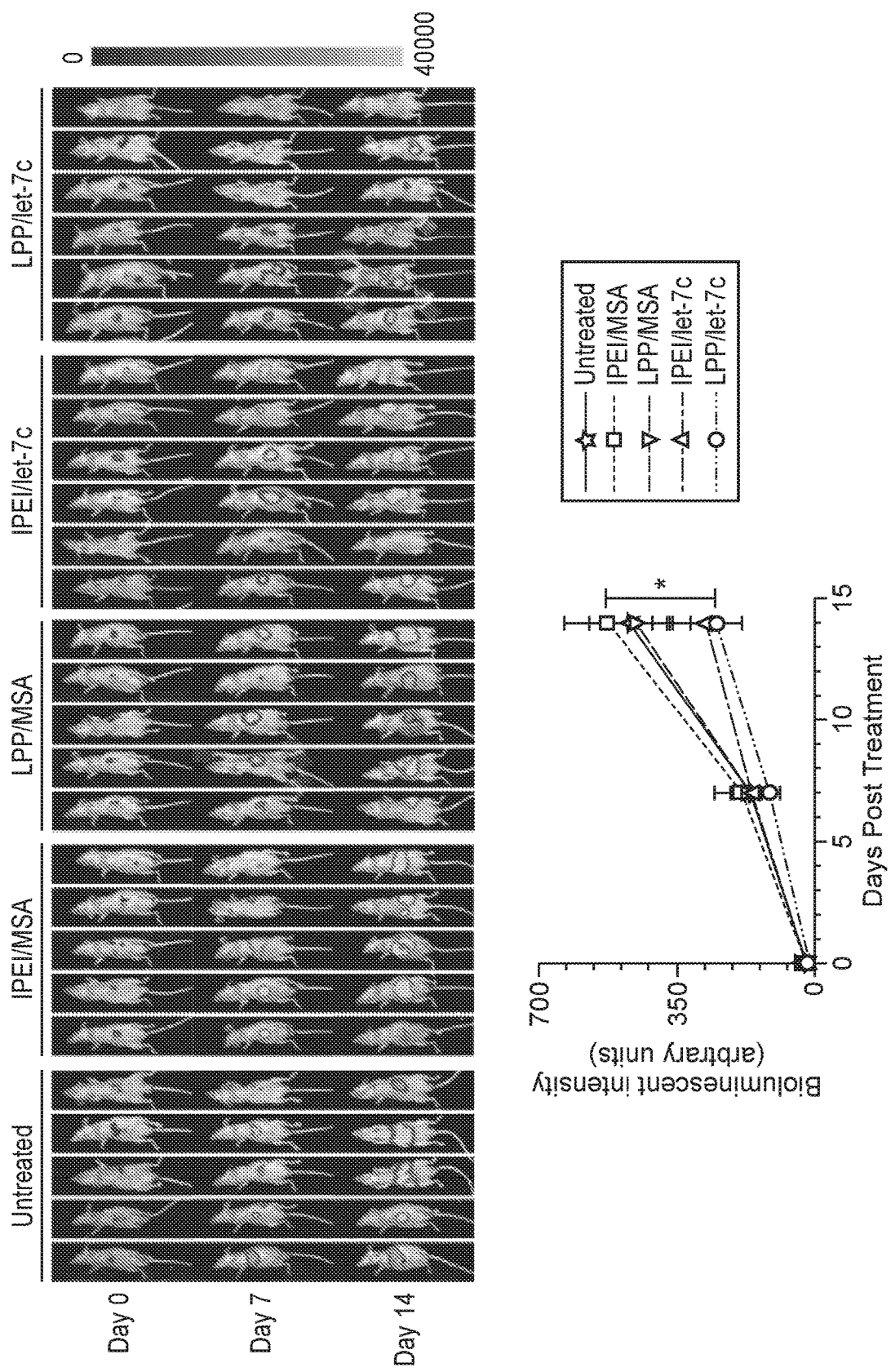

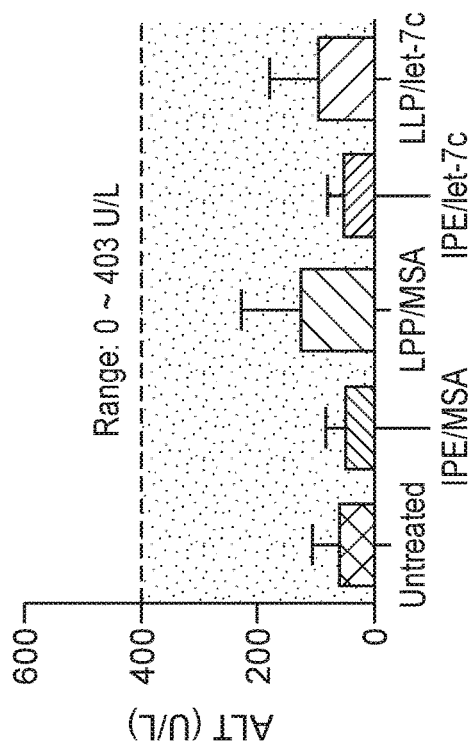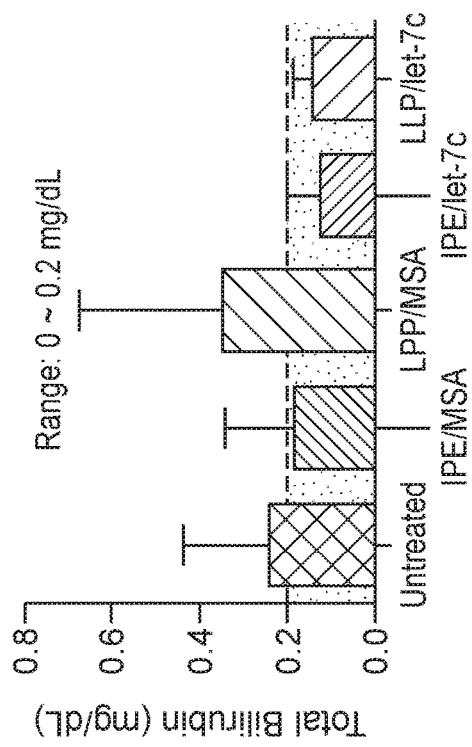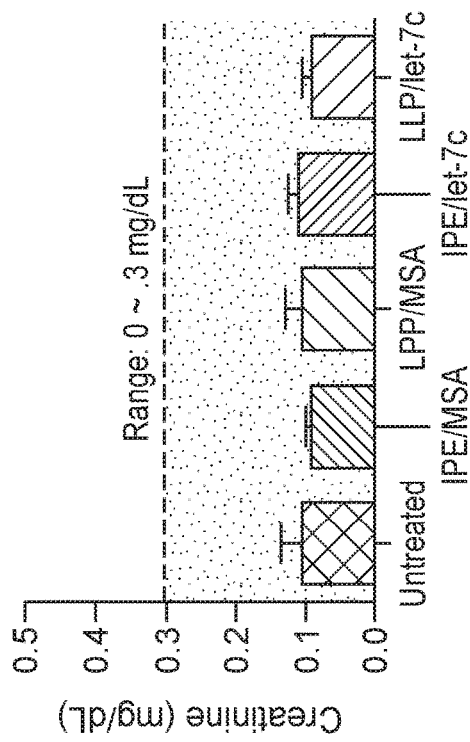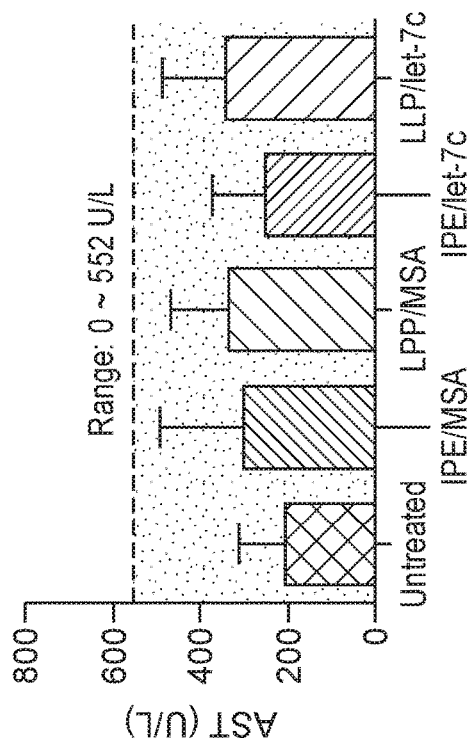

LPP/MSA

LPP/let-7c

Human PBMCs

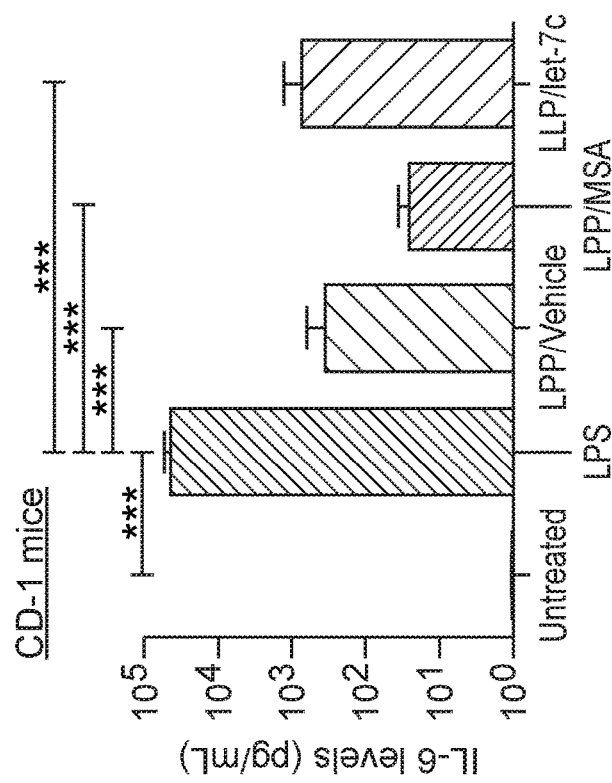
FIG. 13B
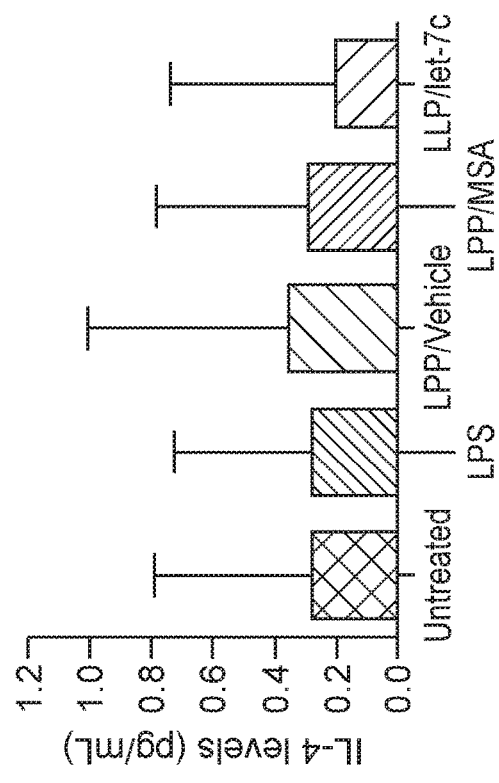
FIG. 13C
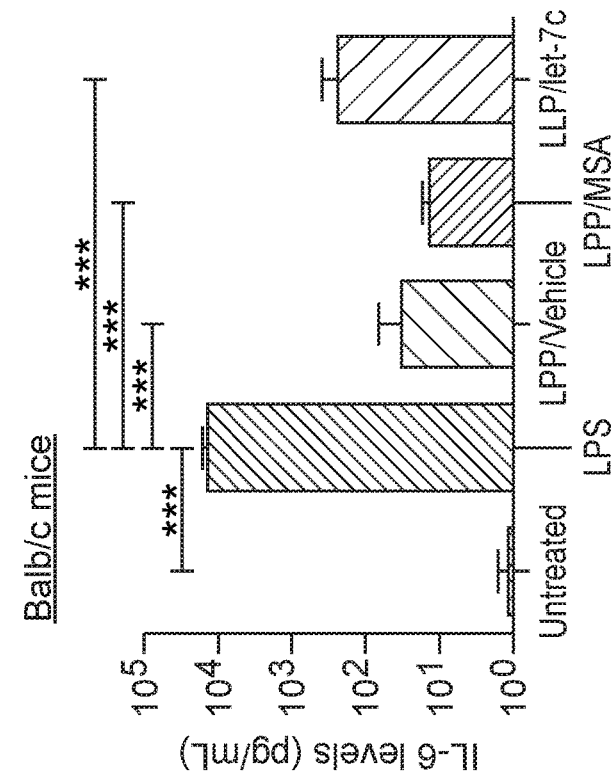
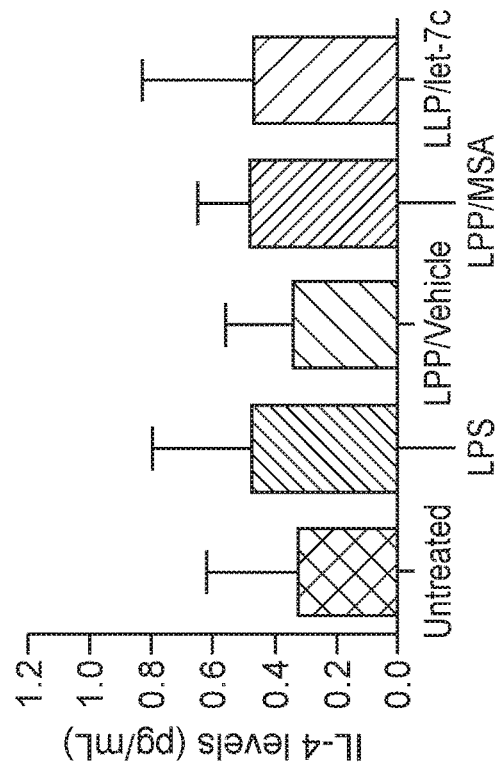

1) Optimize human pre-miR

2) Use human tRNAs (htRNAs)

SEQUENCE LISTING

```
<160> NUMBER OF SEQ ID NOS: 87

<210> SEQ ID NO 1
<211> LENGTH: 180
<212> TYPE: RNA
<213> ORGANISM: Artificial Sequence
<220> FEATURE:
<223> OTHER INFORMATION: Synthetic sequence

<400> SEQUENCE: 1
ggcuacguag cucaguuggu uagagcagcg gccgggccag cugugagugu uucuuuggca     60
gugucuuagc ugguuguugu gagcaauagu aaggaagcaa ucagcaagua uacugcccua    120
gaagugcugc acguuguugg cccccgcggg ucacagguuc gaaucccguc guagccacca    180

<210> SEQ ID NO 2
<211> LENGTH: 192
<212> TYPE: RNA
<213> ORGANISM: Artificial Sequence
<220> FEATURE:
<223> OTHER INFORMATION: Synthetic sequence

<400> SEQUENCE: 2
accaggaugg ccgagugguu aaggcguugg acuggccagc ugugagguguu ucuuuggcag    60 ugucuuagcu gguuguugug agcaauagua aggaagcaau cagcaaguau acugcccuag   120
aagugcugca cguuguuggc ccgauccaau ggacauaugu ccgcgugggu ucgaaccccca  180 cuccugguac ca                                                      192

<210> SEQ ID NO 3
<211> LENGTH: 191
<212> TYPE: RNA
<213> ORGANISM: Artificial Sequence
<220> FEATURE:
<223> OTHER INFORMATION: Synthetic sequence

<400> SEQUENCE: 3
gcagcgaugg ccgagugguu aaggcguugg acuggccagc ugugagguguu ucuuuggcag    60 ugucuuagcu gguuguugug agcaauagua aggaagcaau cagcaaguau acugcccuag   120
aagugcugca cguuguuggc ccaauccaau gggucuccc cgcgcagguu cgaacccugc    180
ucgcugcgcc a                                                        191

<210> SEQ ID NO 4
<211> LENGTH: 182
<212> TYPE: RNA
<213> ORGANISM: Artificial Sequence
<220> FEATURE:
<223> OTHER INFORMATION: Synthetic sequence
```

```
<400> SEQUENCE: 4
gccuggauag cucaguuggu agagcaucag acuggccagc ugugaguguu ucuuuggcag      60
ugucuuagcu gguuguugug agcaauagua aggaagcaau cagcaaguau acugcccuag     120
aagugcugca cguuguuggc ccaaucugag gguccagggu caaguccccu guucaggcgc     180
ca                                                                    182

<210> SEQ ID NO 5
<211> LENGTH: 181
<212> TYPE: RNA
<213> ORGANISM: Artificial Sequence
<220> FEATURE:
<223> OTHER INFORMATION: Synthetic sequence

<400> SEQUENCE: 5
ggucccaugg uguaaugguu agcacucugg acuggccagc ugugaguguu ucuuuggcag      60
ugucuuagcu gguuguugug agcaauagua aggaagcaau cagcaaguau acugcccuag     120
aagugcugca cguuguuggc ccaauccagc gauccgaguu caaaucucgg ugggaccucc     180
a                                                                    181

<210> SEQ ID NO 6
<211> LENGTH: 181
<212> TYPE: RNA
<213> ORGANISM: Artificial Sequence
<220> FEATURE:
<223> OTHER INFORMATION: Synthetic sequence

<400> SEQUENCE: 6
gggggcauag cucaguggua gagcauuuga cuggccagcu gugaguguuu cuuuggcagu      60
gucuuagcug guuguuguga gcaauaguaa ggaagcaauc agcaaguaua cugcccuaga     120
agugcugcac guuguuggcc cgaucaagag gucccugguu caaauccagg ugcccccucc     180
a                                                                    181

<210> SEQ ID NO 7
<211> LENGTH: 167
<212> TYPE: RNA
<213> ORGANISM: Artificial Sequence
<220> FEATURE:
<223> OTHER INFORMATION: Synthetic sequence

<400> SEQUENCE: 7
accaggaugg ccgagugguu aaggcguugg acaggccucu cucccgugu ucacagcgga      60 ccuugauuua aauguccaua caauuaaggc acgcggugaa ugccaagaau ggggcuggau     120
ccaauggaca uauguccgcg uggguucgaa ccccacuccu gguacca                  167

<210> SEQ ID NO 8
<211> LENGTH: 167
<212> TYPE: RNA
<213> ORGANISM: Artificial Sequence
<220> FEATURE:
<223> OTHER INFORMATION: Synthetic sequence

<400> SEQUENCE: 8
gcagcgaugg ccgaguggu u aaggcguugg acuaggccuc ucucccgug uucacagcgg      60 accuugauuu aaauguccau acaauuaagg cacgcgguga augccaagaa uggggcugaa     120 uccaauggg ucuccccgcg cagguucgaa cccugcucgc ugcgcca                   167
```

```
<210> SEQ ID NO 9
<211> LENGTH: 158
<212> TYPE: RNA
<213> ORGANISM: Artificial Sequence
<220> FEATURE:
<223> OTHER INFORMATION: Synthetic sequence

<400> SEQUENCE: 9
gccuggauag cucaguuggu agagcaucag acuaggccuc ucucuccgug uucacagcgg    60
accuugauuu aaauguccau acaauuaagg cacgcgguga augccaagaa ugggcugaa    120 ucugagggguc caggguucaa gucccuguuc aggcgcca                          158

<210> SEQ ID NO 10
<211> LENGTH: 157
<212> TYPE: RNA
<213> ORGANISM: Artificial Sequence
<220> FEATURE:
<223> OTHER INFORMATION: Synthetic sequence

<400> SEQUENCE: 10
ggucccaugg uguaaugguu agcacucugg acuaggccuc ucucuccgug uucacagcgg    60
accuugauuu aaauguccau acaauuaagg cacgcgguga augccaagaa ugggcugaa    120 uccagcgauc cgaguucaaa ucucggguggg accucca                           157

<210> SEQ ID NO 11
<211> LENGTH: 157
<212> TYPE: RNA
<213> ORGANISM: Artificial Sequence
<220> FEATURE:
<223> OTHER INFORMATION: Synthetic sequence

<400> SEQUENCE: 11
gggggcauag cucaguggua gagcauuuga cuaggccucu cucuccgugu ucacagcgga    60
ccuugauuua aauguccaua caauuaaggc acgcggugaa ugccaagaau ggggcuggau    120
caagaggucc cugguucaaa uccaggugcc cccucca                            157

<210> SEQ ID NO 12
<211> LENGTH: 181
<212> TYPE: RNA
<213> ORGANISM: Artificial Sequence
<220> FEATURE:
<223> OTHER INFORMATION: Synthetic sequence

<400> SEQUENCE: 12
ggcuacguag cucaguuggu uagagcagcg gccgggccag cugugagugu uucuuugagg    60 uaguagguu uaugguuugu gagcaauagu aaggaagaac uguacaccuu acuaccuuuc    120
agaagugcug cacguuguug gccccgcgg gucacagguu cgaaucccgu cguagccacc    180
a                                                                   181

<210> SEQ ID NO 13
<211> LENGTH: 193
<212> TYPE: RNA
<213> ORGANISM: Artificial Sequence
<220> FEATURE:
<223> OTHER INFORMATION: Synthetic sequence

<400> SEQUENCE: 13
accaggaugg ccgagugguu aaggcguugg acuggccagc ugugagguguu ucuuugaggu    60 aguagguugu augguuugug agcaauagua aggaagaacu guacaccuua cuaccuuuca    120
```

```
gaagugcugc acguuguugg cccgauccaa uggacauaug uccgcguggg uucgaacccc      180
acuccuggua cca                                                        193

<210> SEQ ID NO 14
<211> LENGTH: 192
<212> TYPE: RNA
<213> ORGANISM: Artificial Sequence
<220> FEATURE:
<223> OTHER INFORMATION: Synthetic sequence

<400> SEQUENCE: 14
gcagcgaugg ccgagugguu aaggcguugg acuggccagc ugugaguguu ucuuugaggu      60
aguagguugu augguuugug agcaauagua aggaagaacu guacaccuua cuaccuuuca     120
gaagugcugc acguuguugg cccaauccaa ugggguccuc ccgcgcaggu ucgaaccccug    180 cucgcugcgc ca                                                        192

<210> SEQ ID NO 15
<211> LENGTH: 183
<212> TYPE: RNA
<213> ORGANISM: Artificial Sequence
<220> FEATURE:
<223> OTHER INFORMATION: Synthetic sequence

<400> SEQUENCE: 15
gccuggauag cucaguuggu agagcaucag acuggccagc ugugaguguu ucuuugaggu      60
aguagguugu augguuugug agcaauagua aggaagaacu guacaccuua cuaccuuuca     120
gaagugcugc acguuguugg cccaaucuga ggguccaggg uucaaguccc guucaggcg      180 cca                                                                   183

<210> SEQ ID NO 16
<211> LENGTH: 182
<212> TYPE: RNA
<213> ORGANISM: Artificial Sequence
<220> FEATURE:
<223> OTHER INFORMATION: Synthetic sequence

<400> SEQUENCE: 16
ggucccaugg uguaaugguu agcacucugg acuggccagc ugugaguguu ucuuugaggu      60
aguagguugu augguuugug agcaauagua aggaagaacu guacaccuua cuaccuuuca     120
gaagugcugc acguuguugg cccaauccag cgauccgagu ucaaaucucg gugggaccuc     180
ca                                                                   182

<210> SEQ ID NO 17
<211> LENGTH: 182
<212> TYPE: RNA
<213> ORGANISM: Artificial Sequence
<220> FEATURE:
<223> OTHER INFORMATION: Synthetic sequence

<400> SEQUENCE: 17
gggggcauag cucaguggua gagcauuuga cuggccagcu gugaguguuu cuuugaggua      60
guagguugua ugguuuguga gcaauaguaa ggaagaacug uacaccuuac uaccuuucag     120
aagugcugca cguuguuggc ccgaucaaga ggucccuggu ucaaauccag gugccccuc      180 ca                                                                   182
```

```
<210> SEQ ID NO 18
<211> LENGTH: 166
<212> TYPE: RNA
<213> ORGANISM: Artificial Sequence
<220> FEATURE:
<223> OTHER INFORMATION: Synthetic sequence

<400> SEQUENCE: 18
gcagcgaugg ccgagugguu aaggcguugg acugcauccg gguugaggua guagguugua      60
ugguuuagag uuacacccug ggaguuaacu guacaaccuu cuagcuuucc uuggagcaau     120
ccaauggggu uccccgcgc agguucgaac ccugcucgcu gcgcca                    166

<210> SEQ ID NO 19
<211> LENGTH: 168
<212> TYPE: RNA
<213> ORGANISM: Artificial Sequence
<220> FEATURE:
<223> OTHER INFORMATION: Synthetic sequence

<400> SEQUENCE: 19
accaggaugg ccgagugguu aaggcguugg acugcauccg gguugaggua guagguugua      60
ugguuuagag uuacacccug ggaguuaacu guacaaccuu cuagcuuucc uuggagcaga     120
uccaauggac auaugccgc guggguucga accccacucc gguacca                   168

<210> SEQ ID NO 20
<211> LENGTH: 152
<212> TYPE: RNA
<213> ORGANISM: Artificial Sequence
<220> FEATURE:
<223> OTHER INFORMATION: Synthetic sequence

<400> SEQUENCE: 20
gccuggauag cucaguuggu agagcaugca uccggguuga gguaguaggu uguaugguuu      60
agaguuacac ccugggaguu aacuguacaa ccuucuagcu uccuuggag caaaucugag     120 gguccagggu ucaagucccu guucaggcgc ca                                 152

<210> SEQ ID NO 21
<211> LENGTH: 157
<212> TYPE: RNA
<213> ORGANISM: Artificial Sequence
<220> FEATURE:
<223> OTHER INFORMATION: Synthetic sequence

<400> SEQUENCE: 21
gggggcauag cucaguggua gagcauuuga cugcauccgg guugagguag uagguuguau      60
gguuuagagu uacacccugg gaguuaacug uacaaccuuc uagcuuuccu uggagcagau     120 caagagagucc cugguucaaa uccaggugcc cccucca                           157

<210> SEQ ID NO 22
<211> LENGTH: 157
<212> TYPE: RNA
<213> ORGANISM: Artificial Sequence
<220> FEATURE:
<223> OTHER INFORMATION: Synthetic sequence

<400> SEQUENCE: 22
ggucccaugg uguaauggu agcacucugg acugcauccg gguugaggua guagguugua      60
ugguuuagag uuacacccug ggaguuaacu guacaaccuu cuagcuuucc uuggagcaaa     120
uccagcgauc cgaguucaaa ucucgguggg accucca                            157
```

```
<210> SEQ ID NO 23
<211> LENGTH: 180
<212> TYPE: RNA
<213> ORGANISM: Artificial Sequence
<220> FEATURE:
<223> OTHER INFORMATION: Synthetic sequence

<400> SEQUENCE: 23
ggcuacguag ucaguuggu uagagcagcg gccgggccag cugugagugu uucuucuggc      60
ccucucugcc cuuccguugu gagcaauagu aaggaagcgg ggggggagaug ggggccauua    120 gaagugcugc acguuguugg cccccgcggg ucacagguuc gaaucccguc guagccacca    180

<210> SEQ ID NO 24
<211> LENGTH: 192
<212> TYPE: RNA
<213> ORGANISM: Artificial Sequence
<220> FEATURE:
<223> OTHER INFORMATION: Synthetic sequence

<400> SEQUENCE: 24
accaggaugg ccgagugguu aaggcguugg acuggccagc ugugaguguu ucuucuggcc     60
cucucugccc uuccguugug agcaauagua aggaagcggg ggggagaugg gggccauuag    120
aagugcugca cguuguuggc ccgauccaau ggacauaugu ccgcguggu ucgaaccccca    180 cuccugguac ca                                                        192

<210> SEQ ID NO 25
<211> LENGTH: 191
<212> TYPE: RNA
<213> ORGANISM: Artificial Sequence
<220> FEATURE:
<223> OTHER INFORMATION: Synthetic sequence

<400> SEQUENCE: 25
gcagcgaugg ccgagugguu aaggcguugg acuggccagc ugugaguguu ucuucuggcc     60
cucucugccc uuccguugug agcaauagua aggaagcggg ggggagaugg gggccauuag    120
aagugcugca cguuguuggc ccaauccaau ggggucuccc cgcgcagguu cgaacccugc    180
ucgcugcgcc a                                                         191

<210> SEQ ID NO 26
<211> LENGTH: 182
<212> TYPE: RNA
<213> ORGANISM: Artificial Sequence
<220> FEATURE:
<223> OTHER INFORMATION: Synthetic sequence

<400> SEQUENCE: 26
gccuggauag ucaguuggu agagcaucag acuggccagc ugugaguguu ucuucuggcc      60
cucucugccc uuccguugug agcaauagua aggaagcggg ggggagaugg gggccauuag    120
aagugcugca cguuguuggc ccaaucugag gguccagggu ucaagucccu guucaggcgc    180
ca                                                                   182

<210> SEQ ID NO 27
<211> LENGTH: 181
<212> TYPE: RNA
<213> ORGANISM: Artificial Sequence
<220> FEATURE:
<223> OTHER INFORMATION: Synthetic sequence
```

```
<400> SEQUENCE: 27
ggucccaugg uguaaugguu agcacucugg acuggccagc ugugaguguu ucuucuggcc      60
cucucugccc uuccguugug agcaauagua aggaagcggg ggggagaugg gggccauuag     120
aagugcugca cguuguuggc ccaauccagc gauccgaguu caaaucucgg ugggaccucc     180
a                                                                    181

<210> SEQ ID NO 28
<211> LENGTH: 181
<212> TYPE: RNA
<213> ORGANISM: Artificial Sequence
<220> FEATURE:
<223> OTHER INFORMATION: Synthetic sequence

<400> SEQUENCE: 28
gggggcauag ucaguggua gagcauuuga cuggccagcu gugaguguuu cuucggccc       60 ucucugcccu uccguuguga gcaauaguaa ggaagcgggg gggagaugg ggccauuaga     120 agugcugcac guuguuggcc cgaucaagag gucccugguu caaaccaggu gcccccucc     180 a                                                                    181

<210> SEQ ID NO 29
<211> LENGTH: 180
<212> TYPE: RNA
<213> ORGANISM: Artificial Sequence
<220> FEATURE:
<223> OTHER INFORMATION: Synthetic sequence

<400> SEQUENCE: 29
ggcuacguag ucaguuggu uagagcagcg gccgggccag cugugagugu uucuuuaagg      60
cacgcgguga augccguugu gagcaauagu aaggaagcgg uguucccguc gugccuucua    120
gaagugcugc acguuguugg ccccgcggg ucacagguuc gaaucccguc guagccacca    180

<210> SEQ ID NO 30
<211> LENGTH: 192
<212> TYPE: RNA
<213> ORGANISM: Artificial Sequence
<220> FEATURE:
<223> OTHER INFORMATION: Synthetic sequence

<400> SEQUENCE: 30
accaggaugg ccgaguggu aaggcguugg acuggccagc ugugaguguu ucuuuaaggc      60
acgcggugaa ugccguugug agcaauagua aggaagcggu guucccgucg ugccuucuag    120
aagugcugca cguuguuggc ccgauccaau ggacauaugu ccgcgugggu ucgaacccca    180
cuccugguac ca                                                        192

<210> SEQ ID NO 31
<211> LENGTH: 191
<212> TYPE: RNA
<213> ORGANISM: Artificial Sequence
<220> FEATURE:
<223> OTHER INFORMATION: Synthetic sequence

<400> SEQUENCE: 31
gcagcgaugg ccgaguggu aaggcguugg acuggccagc ugugaguguu ucuuuaaggc      60
acgcggugaa ugccguugug agcaauagua aggaagcggu guucccgucg ugccuucuag    120
aagugcugca cguuguuggc ccaauccaau gggucuccc cgcgcagguu cgaacccugc     180
ucgcugcgcc a                                                         191
```

<210> SEQ ID NO 32
<211> LENGTH: 182
<212> TYPE: RNA
<213> ORGANISM: Artificial Sequence
<220> FEATURE:
<223> OTHER INFORMATION: Synthetic sequence

<400> SEQUENCE: 32

```
gccuggauag cucaguuggu agagcaucag acuggccagc ugugaguguu ucuuuaaggc    60
acgcggugaa ugccguugug agcaauagua aggaagcggu uucccgucg  ugccuucuag   120
aagugcugca cguuguuggc ccaaucugag gguccagggu ucaagucccu guucaggcgc   180
ca                                                                 182
```

<210> SEQ ID NO 33
<211> LENGTH: 181
<212> TYPE: RNA
<213> ORGANISM: Artificial Sequence
<220> FEATURE:
<223> OTHER INFORMATION: Synthetic sequence

<400> SEQUENCE: 33

```
ggucccaugg uguaaugguu agcacucugg acuggccagc ugugaguguu ucuuuaaggc    60
acgcggugaa ugccguugug agcaauagua aggaagcggu uucccgucg  ugccuucuag   120
aagugcugca cguuguuggc ccaauccagc gauccgaguu caaaucucgg ugggaccucc   180
a                                                                  181
```

<210> SEQ ID NO 34
<211> LENGTH: 181
<212> TYPE: RNA
<213> ORGANISM: Artificial Sequence
<220> FEATURE:
<223> OTHER INFORMATION: Synthetic sequence

<400> SEQUENCE: 34

```
gggggcauag cucaguggua gagcauuuga cuggccagcu gugaguguuu cuuuaaggca    60
cgcggugaau gccguuguga gcaauaguaa ggaagcggug uucccgucgu gccuucuaga   120
agugcugcac guuguuggcc cgaucaagag gucccugguu caaauccagg ugcccccucc   180
a                                                                  181
```

<210> SEQ ID NO 35
<211> LENGTH: 180
<212> TYPE: RNA
<213> ORGANISM: Artificial Sequence
<220> FEATURE:
<223> OTHER INFORMATION: Synthetic sequence

<400> SEQUENCE: 35

```
ggcuacguag cucaguuggu uagagcagcg gccgggccag cugugagugu uucuuucgua    60
ccgugaguaa uaaugcgugu gagcaauagu aaggaagugc auuauucucu augguacgca   120
gaagugcugc acguuguugg cccccgcggg ucacagguuc gaauccguc  guagccacca   180
```

<210> SEQ ID NO 36
<211> LENGTH: 192
<212> TYPE: RNA
<213> ORGANISM: Artificial Sequence
<220> FEATURE:
<223> OTHER INFORMATION: Synthetic sequence

```
<400> SEQUENCE: 36
accaggaugg ccgagugguu aaggcguugg acuggccagc ugugaguguu ucuuucguac       60
cgugaguaau aaugcgugug agcaauagua aggaaggugc auuauucucu augguacgag      120
aagugcugca cguuguuggc ccgauccaau ggacauaugu ccgcggggu cgaaccccca       180 cuccugguac ca                                                          192

<210> SEQ ID NO 37
<211> LENGTH: 191
<212> TYPE: RNA
<213> ORGANISM: Artificial Sequence
<220> FEATURE:
<223> OTHER INFORMATION: Synthetic sequence

<400> SEQUENCE: 37
gcagcgaugg ccgagugguu aaggcguugg acuggccagc ugugaguguu ucuuucguac       60
cgugaguaau aaugcgugug agcaauagua aggaaggugc auuauucucu augguacgag      120
aagugcugca cguuguuggc ccaauccaau ggggucuccc cgcgcagguu cgaacccugc      180
ucgcugcgcc a                                                           191

<210> SEQ ID NO 38
<211> LENGTH: 182
<212> TYPE: RNA
<213> ORGANISM: Artificial Sequence
<220> FEATURE:
<223> OTHER INFORMATION: Synthetic sequence

<400> SEQUENCE: 38
gccuggauag cucaguuggu agagcaucag acuggccagc ugugaguguu ucuuucguac       60
cgugaguaau aaugcgugug agcaauagua aggaaggugc auuauucucu augguacgag      120
aagugcugca cguuguuggc ccaaucugag gguccagggu caagucccu guucaggcgc       180 ca                                                                     182

<210> SEQ ID NO 39
<211> LENGTH: 181
<212> TYPE: RNA
<213> ORGANISM: Artificial Sequence
<220> FEATURE:
<223> OTHER INFORMATION: Synthetic sequence

<400> SEQUENCE: 39
ggucccaugg uguaaugguu agcacucugg acuggccagc ugugaguguu ucuuucguac       60
cgugaguaau aaugcgugug agcaauagua aggaaggugc auuauucucu augguacgag      120
aagugcugca cguuguuggc ccaauccagc gauccgaguu caaaucucgg ugggaccucc      180
a                                                                      181

<210> SEQ ID NO 40
<211> LENGTH: 181
<212> TYPE: RNA
<213> ORGANISM: Artificial Sequence
<220> FEATURE:
<223> OTHER INFORMATION: Synthetic sequence

<400> SEQUENCE: 40
gggggcauag cucaguggua gagcauuuga cuggccagcu gugaguguuu cuuucguacc       60
gugaguaaua augcguguga gcaauaguaa ggaaggugca uuauucucua ugguacgaga      120
```

```
agugcugcac guuguuggcc cgaucaagag gucccugguu caaauccagg ugcccccucc      180
a                                                                      181

<210> SEQ ID NO 41
<211> LENGTH: 180
<212> TYPE: RNA
<213> ORGANISM: Artificial Sequence
<220> FEATURE:
<223> OTHER INFORMATION: Synthetic sequence

<400> SEQUENCE: 41
ggcuacguag ucaguuggu uagagcagcg gccgggccag cugugagugu uucuuagcag       60
aagcagggag guucucccau gagcaauagu aaggagggga gaaccccau gcuuuugaca      120 gaagugcugc acguuguugg cccccgcggg ucacagguuc gaaucccguc guagccacca    180

<210> SEQ ID NO 42
<211> LENGTH: 194
<212> TYPE: RNA
<213> ORGANISM: Artificial Sequence
<220> FEATURE:
<223> OTHER INFORMATION: Synthetic sequence

<400> SEQUENCE: 42
accaggaugg ccgagugguu aaggcguugg acuggccagc ugugagguu ucuuagcaga       60 agcagggagg uucucccaug ugagcaauag uaaggaaggg agaaccccca ugcuuuugac    120
agaagugcug cacguuguug gcccgaucca auggacauau guccgcgugg guucgaaccc    180
cacuccuggu acca                                                       194

<210> SEQ ID NO 43
<211> LENGTH: 193
<212> TYPE: RNA
<213> ORGANISM: Artificial Sequence
<220> FEATURE:
<223> OTHER INFORMATION: Synthetic sequence

<400> SEQUENCE: 43
gcagcgaugg ccgagugguu aaggcguugg acuggccagc ugugagguu ucuuagcaga       60 agcagggagg uucucccaug ugagcaauag uaaggaaggg agaaccccca ugcuuuugac    120
agaagugcug cacguuguug gcccaaucca auggggucuc cccgcgcagg uucgaacccu    180
gcucgcugcg cca                                                        193

<210> SEQ ID NO 44
<211> LENGTH: 184
<212> TYPE: RNA
<213> ORGANISM: Artificial Sequence
<220> FEATURE:
<223> OTHER INFORMATION: Synthetic sequence

<400> SEQUENCE: 44
gccuggauag ucaguuggu agagcaucag acuggccagc ugugagguu ucuuagcaga       60 agcagggagg uucucccaug ugagcaauag uaaggaaggg agaaccccca ugcuuuugac    120
agaagugcug cacguuguug gcccaaucug agggccagg uucaagucc cuguucaggc      180 gcca                                                                  184

<210> SEQ ID NO 45
<211> LENGTH: 183
<212> TYPE: RNA
<213> ORGANISM: Artificial Sequence
```

<220> FEATURE:
<223> OTHER INFORMATION: Synthetic sequence

<400> SEQUENCE: 45

```
ggucccaugg uguaaugguu agcacucugg acuggccagc ugugaguguu ucuuagcaga      60
agcagggagg uucucccaug ugagcaauag uaaggaaggg agaaccccca ugcuuuugac     120
agaagugcug cacguuguug gcccaaucca gcgauccgag uucaaaucuc ggugggaccu     180
cca                                                                   183
```

<210> SEQ ID NO 46
<211> LENGTH: 183
<212> TYPE: RNA
<213> ORGANISM: Artificial Sequence
<220> FEATURE:
<223> OTHER INFORMATION: Synthetic sequence

<400> SEQUENCE: 46

```
gggggcauag cucaguggua gagcauuuga cuggccagcu gugaguguuu cuuagcagaa      60
gcagggaggu ucucccaugu gagcaauagu aaggaaggga gaaccccau gcuuuugaca     120
gaagugcugc acguuguugg cccgaucaag aggucccugg uucaaaucca ggugccccu     180
cca                                                                   183
```

<210> SEQ ID NO 47
<211> LENGTH: 119
<212> TYPE: RNA
<213> ORGANISM: Artificial Sequence
<220> FEATURE:
<223> OTHER INFORMATION: Synthetic sequence

<400> SEQUENCE: 47

```
accaggaugg ccgagugguu aaggcguugg acuaguaauu acgucgacg gugacgucga       60
ugguugcggg auccaaugga cauauguccg cgugggttucg aaccccacuc cugguacca    119
```

<210> SEQ ID NO 48
<211> LENGTH: 118
<212> TYPE: RNA
<213> ORGANISM: Artificial Sequence
<220> FEATURE:
<223> OTHER INFORMATION: Synthetic sequence

<400> SEQUENCE: 48

```
gcagcgaugg ccgagugguu aaggcguugg acuaguaauu acgucgacg gugacgucga       60
ugguugcgga auccaauggg gucuccccgc gcagguucga acccugcucg cugcgcca     118
```

<210> SEQ ID NO 49
<211> LENGTH: 109
<212> TYPE: RNA
<213> ORGANISM: Artificial Sequence
<220> FEATURE:
<223> OTHER INFORMATION: Synthetic sequence

<400> SEQUENCE: 49

```
gccuggauag cucaguuggu agagcaucag acuaguaauu acgucgacg gugacgucga       60
ugguugcgga aucgagggu ccaggguuca aguccccuguu caggcacca                109
```

<210> SEQ ID NO 50
<211> LENGTH: 108
<212> TYPE: RNA
<213> ORGANISM: Artificial Sequence
<220> FEATURE:
<223> OTHER INFORMATION: Synthetic sequence

<400> SEQUENCE: 50
ggucccaugg uguaaugguu agcacucugg acuaguaauu uacgucgacg gugacgucga    60
ugguugcgga auccagcgau ccgaguucaa aucucggugg gaccucca    108

<210> SEQ ID NO 51
<211> LENGTH: 108
<212> TYPE: RNA
<213> ORGANISM: Artificial Sequence
<220> FEATURE:
<223> OTHER INFORMATION: Synthetic sequence

<400> SEQUENCE: 51
gggggcauag cucagugguu gagcauuuga cuaguaauuu acgucgacgg ugacgucgau    60
gguugcggga ucaagagguc ccugguucaa auccaggugc ccccucca    108

<210> SEQ ID NO 52
<211> LENGTH: 109
<212> TYPE: RNA
<213> ORGANISM: Artificial Sequence
<220> FEATURE:
<223> OTHER INFORMATION: Synthetic sequence

<400> SEQUENCE: 52
gccucguuag cgcaguaggu agcgcgucag ucuaguaauu uacgucgacg gugacgucga    60
ugguugcgga aucugaaggu cgugaguucg auccucacac ggggcacca    109

<210> SEQ ID NO 53
<211> LENGTH: 102
<212> TYPE: RNA
<213> ORGANISM: Artificial Sequence
<220> FEATURE:
<223> OTHER INFORMATION: Synthetic sequence

<400> SEQUENCE: 53
accaggaugg ccgagugguu aaggcguugg acugcgacug guuacccggu cggauccaau    60
ggacauaugu ccgcguggu ucgaaccca cuccugguac ca    102

<210> SEQ ID NO 54
<211> LENGTH: 101
<212> TYPE: RNA
<213> ORGANISM: Artificial Sequence
<220> FEATURE:
<223> OTHER INFORMATION: Synthetic sequence

<400> SEQUENCE: 54
gcagcgaugg ccgagugguu aaggcguugg acugcgacug guuacccggu cgaauccaau    60
ggggucuccc cgcgcagguu cgaacccugc ucgcugcgcc a    101

<210> SEQ ID NO 55
<211> LENGTH: 92
<212> TYPE: RNA
<213> ORGANISM: Artificial Sequence
<220> FEATURE:
<223> OTHER INFORMATION: Synthetic sequence

<400> SEQUENCE: 55
gccuggauag cucaguuggu agagcaucag acugcgacug guuacccggu cgaaucugag    60
gguccagggu ucaagucccu guucaggcac ca    92

<210> SEQ ID NO 56
<211> LENGTH: 91
<212> TYPE: RNA
<213> ORGANISM: Artificial Sequence
<220> FEATURE:
<223> OTHER INFORMATION: Synthetic sequence

<400> SEQUENCE: 56
ggucccaugg uguaauggu uagcacucugg acugcgacug guuacccggu cgaauccagc    60
gauccgaguu caaaucucgg ugggaccucc a                                  91

<210> SEQ ID NO 57
<211> LENGTH: 91
<212> TYPE: RNA
<213> ORGANISM: Artificial Sequence
<220> FEATURE:
<223> OTHER INFORMATION: Synthetic sequence

<400> SEQUENCE: 57
gggggcauag cucaguggua gagcauuuga cugcgacugg uuacccgguc ggaucaagag    60
gucccugguu caaaccagg ugcccccucc a                                   91

<210> SEQ ID NO 58
<211> LENGTH: 92
<212> TYPE: RNA
<213> ORGANISM: Artificial Sequence
<220> FEATURE:
<223> OTHER INFORMATION: Synthetic sequence

<400> SEQUENCE: 58
gccucguuag cgcaguaggu agcgcgucag ucugcgacug guuacccggu cgaaucugaa    60
ggucgugagu ucgauccuca cacggggcac ca                                 92

<210> SEQ ID NO 59
<211> LENGTH: 116
<212> TYPE: RNA
<213> ORGANISM: Artificial Sequence
<220> FEATURE:
<223> OTHER INFORMATION: Synthetic sequence

<400> SEQUENCE: 59
accaggaugg ccgagugguu aaggcguugg acuggcgaua ccagccgaaa ggcccuuggc    60
agcgucgauc caauggacau auguccgcgu ggguucgaac cccacuccug guacca       116

<210> SEQ ID NO 60
<211> LENGTH: 115
<212> TYPE: RNA
<213> ORGANISM: Artificial Sequence
<220> FEATURE:
<223> OTHER INFORMATION: Synthetic sequence

<400> SEQUENCE: 60
gcagcgaugg ccgagugguu aaggcguugg acuggcgaua ccagccgaaa ggcccuuggc    60
agcgucaauc caauggguc uccccgcgca gguucgaacc cugcucgcug cgcca         115

<210> SEQ ID NO 61
<211> LENGTH: 106
<212> TYPE: RNA
<213> ORGANISM: Artificial Sequence
<220> FEATURE:
<223> OTHER INFORMATION: Synthetic sequence

```
<400> SEQUENCE: 61
gccuggauag cucaguuggu agagcaucag acuggcgaua ccagccgaaa ggcccuuggc    60
agcgucaauc ugagggucca ggguucaagu cccuguucag gcacca                 106

<210> SEQ ID NO 62
<211> LENGTH: 105
<212> TYPE: RNA
<213> ORGANISM: Artificial Sequence
<220> FEATURE:
<223> OTHER INFORMATION: Synthetic sequence

<400> SEQUENCE: 62
ggucccaugg uguaaugguu agcacucugg acuggcgaua ccagccgaaa ggcccuuggc    60
agcgucaauc cagcgauccg aguucaaauc ucggugggac cucca                  105

<210> SEQ ID NO 63
<211> LENGTH: 105
<212> TYPE: RNA
<213> ORGANISM: Artificial Sequence
<220> FEATURE:
<223> OTHER INFORMATION: Synthetic sequence

<400> SEQUENCE: 63
gggggcauag cucaguggua gagcauuuga cuggcgauac cagccgaaag gcccuuggca    60
gcgucgauca agaggucccu gguucaaauc caggugcccc cucca                  105

<210> SEQ ID NO 64
<211> LENGTH: 106
<212> TYPE: RNA
<213> ORGANISM: Artificial Sequence
<220> FEATURE:
<223> OTHER INFORMATION: Synthetic sequence

<400> SEQUENCE: 64
gccucguuag cgcaguaggu agcgcgucag ucuggcgaua ccagccgaaa ggcccuuggc    60
agcgucaauc ugaaggucgu gaguucgauc cucacacggg gcacca                 106

<210> SEQ ID NO 65
<211> LENGTH: 50
<212> TYPE: DNA
<213> ORGANISM: Artificial Sequence
<220> FEATURE:
<223> OTHER INFORMATION: Synthetic sequence

<400> SEQUENCE: 65
gtcgtatcca gtgcagggtc ccaggtattc gcactggata cgacaaccat               50

<210> SEQ ID NO 66
<211> LENGTH: 18
<212> TYPE: DNA
<213> ORGANISM: Artificial Sequence
<220> FEATURE:
<223> OTHER INFORMATION: Synthetic sequence

<400> SEQUENCE: 66
gcgctaaggc acgcggtg                                                  18

<210> SEQ ID NO 67
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 67
cgcgctgagg tagtaggttg t                                           21

<210> SEQ ID NO 68
<211> LENGTH: 20
<212> TYPE: DNA
<213> ORGANISM: Artificial Sequence
<220> FEATURE:
<223> OTHER INFORMATION: Synthetic sequence

<400> SEQUENCE: 68
acgtaaacgg ccacaagttc                                             20

<210> SEQ ID NO 69
<211> LENGTH: 20
<212> TYPE: DNA
<213> ORGANISM: Artificial Sequence
<220> FEATURE:
<223> OTHER INFORMATION: Synthetic sequence

<400> SEQUENCE: 69
aagtcgtgct gcttcatgtg                                             20

<210> SEQ ID NO 70
<211> LENGTH: 20
<212> TYPE: DNA
<213> ORGANISM: Artificial Sequence
<220> FEATURE:
<223> OTHER INFORMATION: Synthetic sequence

<400> SEQUENCE: 70
gtaacccgtt gaacccccatt                                            20

<210> SEQ ID NO 71
<211> LENGTH: 20
<212> TYPE: DNA
<213> ORGANISM: Artificial Sequence
<220> FEATURE:
<223> OTHER INFORMATION: Synthetic sequence

<400> SEQUENCE: 71
ccatccaatc ggtagtagcg                                             20

<210> SEQ ID NO 72
<211> LENGTH: 17
<212> TYPE: DNA
<213> ORGANISM: Artificial Sequence
<220> FEATURE:
<223> OTHER INFORMATION: Synthetic sequence

<400> SEQUENCE: 72
ctcgcttcgg cagcaca                                                17

<210> SEQ ID NO 73
<211> LENGTH: 20
<212> TYPE: DNA
<213> ORGANISM: Artificial Sequence
<220> FEATURE:
<223> OTHER INFORMATION: Synthetic sequence

<400> SEQUENCE: 73
aacgcttcac gaatttgcgt                                             20

```
<210> SEQ ID NO 74
<211> LENGTH: 29
<212> TYPE: RNA
<213> ORGANISM: Artificial Sequence
<220> FEATURE:
<223> OTHER INFORMATION: Synthetic sequence

<400> SEQUENCE: 74
guggaccggc cagcugugag uguuucuuu                                              29

<210> SEQ ID NO 75
<211> LENGTH: 39
<212> TYPE: RNA
<213> ORGANISM: Artificial Sequence
<220> FEATURE:
<223> OTHER INFORMATION: Synthetic sequence

<400> SEQUENCE: 75
uagaagggag aacccggggu guugcacguc gugaagauc                                   39

<210> SEQ ID NO 76
<211> LENGTH: 22
<212> TYPE: RNA
<213> ORGANISM: Artificial Sequence
<220> FEATURE:
<223> OTHER INFORMATION: Synthetic sequence

<400> SEQUENCE: 76
ggccagcugu gaguguuucu uu                                                     22

<210> SEQ ID NO 77
<211> LENGTH: 27
<212> TYPE: RNA
<213> ORGANISM: Artificial Sequence
<220> FEATURE:
<223> OTHER INFORMATION: Synthetic sequence

<400> SEQUENCE: 77
cccggggugu ugcacgucgu gaagauc                                                27

<210> SEQ ID NO 78
<211> LENGTH: 26
<212> TYPE: RNA
<213> ORGANISM: Artificial Sequence
<220> FEATURE:
<223> OTHER INFORMATION: Synthetic sequence

<400> SEQUENCE: 78 ccggggoguu gcacgucgug aagauc                                                 26

<210> SEQ ID NO 79
<211> LENGTH: 26
<212> TYPE: RNA
<213> ORGANISM: Artificial Sequence
<220> FEATURE:
<223> OTHER INFORMATION: Synthetic sequence

<400> SEQUENCE: 79
cccgguuguu gcacgucgug aagauc                                                 26

<210> SEQ ID NO 80
<211> LENGTH: 23
<212> TYPE: RNA
<213> ORGANISM: Artificial Sequence
<220> FEATURE:
<223> OTHER INFORMATION: Synthetic sequence
```

```
<400> SEQUENCE: 80
ggccccgcug ugaguguuuc uuu                                              23

<210> SEQ ID NO 81
<211> LENGTH: 26
<212> TYPE: RNA
<213> ORGANISM: Artificial Sequence
<220> FEATURE:
<223> OTHER INFORMATION: Synthetic sequence

<400> SEQUENCE: 81
cccggggugu ucacgucgug aagauc                                           26

<210> SEQ ID NO 82
<211> LENGTH: 24
<212> TYPE: RNA
<213> ORGANISM: Artificial Sequence
<220> FEATURE:
<223> OTHER INFORMATION: Synthetic sequence

<400> SEQUENCE: 82
cgggccagcu gugaguguuu cuuu                                             24

<210> SEQ ID NO 83
<211> LENGTH: 28
<212> TYPE: RNA
<213> ORGANISM: Artificial Sequence
<220> FEATURE:
<223> OTHER INFORMATION: Synthetic sequence

<400> SEQUENCE: 83
ccccggggug uugcacgucg ugaagauc                                         28

<210> SEQ ID NO 84
<211> LENGTH: 28
<212> TYPE: RNA
<213> ORGANISM: Artificial Sequence
<220> FEATURE:
<223> OTHER INFORMATION: Synthetic sequence

<400> SEQUENCE: 84
cggccgggcc agcugugagu guuucuuu                                         28

<210> SEQ ID NO 85
<211> LENGTH: 33
<212> TYPE: RNA
<213> ORGANISM: Artificial Sequence
<220> FEATURE:
<223> OTHER INFORMATION: Synthetic sequence

<400> SEQUENCE: 85
ggcgcccccg ggguguugca cgucgugaag auc                                   33

<210> SEQ ID NO 86
<211> LENGTH: 32
<212> TYPE: RNA
<213> ORGANISM: Artificial Sequence
<220> FEATURE:
<223> OTHER INFORMATION: Synthetic sequence

<400> SEQUENCE: 86 ggcgccccccg guguugcac gucgugaaga uc                                    32
```

```
<210> SEQ ID NO 87
<211> LENGTH: 29
<212> TYPE: RNA
<213> ORGANISM: Artificial Sequence
<220> FEATURE:
<223> OTHER INFORMATION: Synthetic sequence

<400> SEQUENCE: 87
cggccgggcc ccgcugugag uguuucuuu                              29
```

TRNA/PRE-MIRNA COMPOSITIONS AND METHODS FOR TREATING HEPATOCELLULAR CARCINOMA

CROSS-REFERENCE TO RELATED APPLICATIONS

This application claims the benefit of U.S. Provisional Patent Application No. 62/660,919, filed Apr. 20, 2018, which application is incorporated herein by reference in its entirety.

INCORPORATION BY REFERENCE OF SEQUENCE LISTING PROVIDED AS A TEXT FILE

A Sequence Listing is provided herewith in a text file, UCDV-352WO_SEQ_LISTING_ST25, created on Nov. 12, 2020 and having a size of 28,069 bytes. The contents of the text file are incorporated herein by reference in its entirety.

STATEMENT OF GOVERNMENTAL SUPPORT

This invention was made with government support under Grant Nos. R01GM113888, U01CA175315, T32GM099608 and P30CA093373, awarded by the National Institutes of Health. The government has certain rights in the invention.

BACKGROUND

Hepatocellular carcinoma (HCC) is the most common malignancy of liver with a 5-year relative survival rate of 18% (1) and an overall median survival of 29.8 months without improvement over time (2). Furthermore, the incidence of HCC continues to increase, in contrast to a declining trend of all cancers as well as the most common cancers (e.g., lung, breast, prostate and colon cancer, etc.) since 2009 (1). While surgical resection represents a favorable treatment strategy to improve long-term survival of HCC patients, it is impractical for patients with advanced HCC or at late stages, and pharmacological intervention is also limited (3-5). The multi-kinase inhibitor sorafenib has been a first-line therapy for patients with advanced HCC, whereas it only increases overall survival by only three months (6). Second-line treatment with regorafenib following progression on sorafenib yielded a similar three-month extension of median survival in patients, whereas was accompanied by adverse effects (7). Although very recent accelerated approval of nivolumab as immunotherapy brings hopes to HCC patients who have been previously treated with sorafenib (8), advances in HCC therapy have been slow compared to most solid tumors. As a result, liver cancer is now the fifth and second leading cause of cancer-related deaths in the United States (1) and worldwide (9), respectively. Therefore, more effective therapeutic strategies are urgently needed for HCC.

Pharmacological interventions are hindered, in part, by the molecular heterogeneity and complex etiology of HCC. The discovery of genomically-transcribed noncoding microRNAs (miRNA or miR) behind cancer cellular processes offers clue to developing novel miRNA based therapies for the treatment of cancers (10-14). For instance, tumor suppressive miRNAs (e.g., miR-124 and -206, etc.) depleted in HCC tissues may be reintroduced into cancer cells to manage HCC progression (15-19). This approach is named as "miRNA replacement therapy" (11), different from the miRNA antagonism strategy. Given the fact that miRNAs are normal constituents of healthy cells, restoration of miRNA expression/function using the same sequence of ncRNA molecules is likely more tolerable in cells.

To investigate miRNA based cancer therapies, we have developed a novel bioengineering platform to produce recombinant miRNA agents, based upon the stable hybrid tRNA/pre-miRNA molecules (e.g., tRNAmet/pre-miR-34a) identified in our lab (20, 21). By replacing the miRNA (e.g., miR-34a) duplexes with target miRNA (e.g., let-7c) or siRNA (e.g., GFP-siRNA), we are able to produce a set of miRNA/siRNA agents (21). Folded and tolerated in living cells, biologic/bioengineered miRNA agents are distinguished from conventional miRNA mimics or molecules made in test tubes through chemical synthesis or enzymatic reactions (22). This is in line with the ultimate success of protein research and therapy using recombinant proteins instead of synthetic polypeptides/proteins as both RNAs and proteins are biological macromolecules. Further studies have demonstrated that bioengineered noncoding RNA (ncRNA) molecules are selectively processed to target miRNA/siRNA molecules in human cells, which consequently modulate target gene expression, control cancer cellular processes and suppress tumor progression (20, 21, 23-26).

Systemic RNA therapy is also hampered by the susceptibility of RNA molecules to serum RNases and ability to cross membrane barrier, warranting proper delivery systems. Polyethylenimine (PEI)-based polyplexes (complexes of nucleic acids and PEI) have been revealed to offer high delivery efficiency, whereas polyplexes may increase the risk of toxicity (27). Lipidation of polyplexes can reduce the toxicity of polyplexes (28) because the resultant lipopolyplexes (LPP) exhibit more favorable biological properties and biocompatibilities (29-31). Our recent studies have also revealed that PEI-based cationic LPP nanocomplex offers efficient delivery of bioengineered RNA molecules in an orthotopic HCC xenograft mouse models, leading to more consistent knockdown of target gene expression than polyplex in tumoral tissues.

SUMMARY

In one aspect, provided are polynucleotides comprising a tRNA operably linked to one or more pre-microRNA (pre-miRNA), wherein the tRNA and/or pre-miRNA are operably linked to one or more inserted RNA molecules that reduce or inhibit the growth or proliferation of a hepatocellular carcinoma (HCC) cell. In some embodiments, all or part of the stem-loop anticodon of the tRNA is replaced with the pre-miRNA. In some embodiments, the inserted RNA molecule is inserted at, abutted with or operably linked to: (a) the 5' end of the pre-miRNA; (b) the 3' end of the pre-miRNA; (c) 5' of a dicer or RNase cleavage site of the pre-miRNA; or (d) 3' of a dicer or RNase cleavage site of the pre-miRNA. In some embodiments, the polynucleotide is from about 75 nucleotides, e.g., from about 100 nucleotides, e.g., from about 125 nucleotides, e.g., from about 150 nucleotides and up to about 200 nucleotides in length. In some embodiments, the tRNA is a tRNA coding for any naturally occurring amino acid, e.g., glycine, alanine, aspartate, glutamate, asparagine, glutamine, arginine, lysine, cysteine, phenylalanine, tyrosine, histidine, tryptophan, leucine, isoleucine, valine, threonine, serine, proline, and methionine. In some embodiments, the tRNA is a tRNA coding for an amino acid selected from the group consisting of leucine, serine, glutamine, lysine, cysteine and methionine. In some embodiments, the tRNA is a mammalian tRNA, e.g., a human tRNA. In some embodiments, the tRNA has a nucleic acid sequence having at least about 90%, 91%, 92%, 93%, 94%, 95%, 96%, 97%, 98%, 99% or 100% sequence identity to one of SEQ ID NOs:47-64. In some embodiments, the one or more pre-miRNA are selected from the group consisting of pre-miR-34a, pre-miR-124, pre-let-7c, pre-miR-328, pre-miR-126, pre-miR-298 and pre-miR-200. In some embodiments, the one or more pre-miRNA are selected from the group consisting of pre-miR-34a-5p, pre-miR-124-3p, pre-let-7c-5p, pre-miR-328-3p, pre-miR-126-3p, and pre-miR-298-5p. In some embodiments, the polynucleotide comprises two or more pre-miRNA, wherein each pre-miRNA is operably linked to an inserted RNA molecule, e.g., wherein the two or more pre-miRNA are the same or different, e.g., wherein the inserted RNA is the same or different. In some embodiments, the inserted RNA is selected from the group consisting of a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a guide RNA (gRNA), an antisense RNA (asRNA), a small activating RNA (saRNA), a catalytic RNA, a riboswitch, and an RNA aptamer. In some embodiments, the inserted RNA is a noncoding RNA. In some embodiments, the inserted RNA is a mature miRNA selected from the group consisting of let-7c, miR-298, miR-216, miR-124, miR-328, miR-144, miR-126, miR-16, miR-18, miR-125a, miR-195, miR-199a, miR-200, and miR-224. In some embodiments, the inserted RNA prevents, reduces or inhibits the expression of a target polypeptide in an HCC cell. In some embodiments, the tRNA and/or pre-miRNA are operably linked to an aptamer. In some embodiments, the aptamer is inserted at, abutted with or operably linked to: (a) the 5' end of the pre-miRNA; (b) the 3' end of the pre-miRNA; (c) 5' of a dicer or RNase cleavage site of the pre-miRNA; or (d) 3' of a dicer or RNase cleavage site of the pre-miRNA. In some embodiments, the aptamer binds to a target antigen selected from the group consisting of EpCam, vascular endothelial growth factor (VEGF), fms related tyrosine kinase 1 (FLT1), theophylline, malachite green, HCC-22-5, keratin 23 (KRT23), alpha 2-HS glycoprotein (AHSG) and ferritin light chain (FTL). In some embodiments, the pre-miRNA is naturally or artificially derived, e.g., is expressed in a cell or synthetically produced. In some embodiments, the polynucleotide comprises at least about 90%, 91%, 92%, 93%, 94%, 95%, 96%, 97%, 98%, 99% or 100% sequence identity to one of SEQ ID NOs:1-46. In some embodiments, the polynucleotide is substantially non-immunogenic to a mammal, e.g., to a human.

In a further aspect, provided is an expression cassette comprising the polynucleotide, as described above and herein.

In a further aspect, provided is a viral vector comprising the polynucleotide or the expression cassette, as described above and herein.

In a further aspect, provided is a liposome or a nanoparticle comprising the polynucleotide or the expression cassette, as described above and herein. In some embodiments, the liposome comprises an inner core comprising the polynucleotide of any complexed with a polyethylenimine (PEI) and an outer lipid bilayer. In some embodiments, the inner core comprises a liposomal-branched polyethylenimine (PEI) polyplex (LPP), e.g., having a molecular weight of about 10,000 daltons. In some embodiments, the outer lipid bilayer comprises a mixture of 1,2-di-O-octadecenyl-3-trimethylammonium propane (DOTMA), cholesterol and 1,2-Dimyristoyl-sn-glycerol, methoxypolyethylene glycol (DMG-PEG2000).

In a further aspect, provided is a host cell transfected or transformed with the polynucleotide. the expression cassette, the liposome or nanoparticle, as described above and herein. In some embodiments, the host cell is a prokaryotic cell or a eukaryotic cell. In some embodiments, the host cell is selected from a bacterial cell, a mammalian cell, an insect cell or a plant cell.

In a further aspect, provided are methods of preventing, mitigating, reducing, reversing and/or inhibiting the growth, proliferation, and/or progression of hepatocellular cancer (HCC) in a subject in need thereof. In some embodiments, the methods entail administering to the subject the polynucleotide, the expression cassette, the liposome or nanoparticle, as described above and herein. In some embodiments, the polynucleotide, liposome or nanoparticle is administered via a route selected from intravenously, intraarterially, intraperitoneally, intrahepatically, subcutaneously or intratumorally. In some embodiments, a therapeutic regimen of the polynucleotide, liposome or nanoparticle is administered is ad ministered multiple times, e.g., daily, weekly, bi-weekly, monthly, e.g., until a predetermined or desired endpoint is reached. In some embodiments, the subject is exhibiting symptoms of HCC, e.g., has one or more tumors. In some embodiments, the subject is in remission and is at risk of redeveloping HCC tumors. In some embodiments, the methods comprise co-administration of one or more chemotherapeutic or anticancer agents. In some embodiments, the subject is tested for the overexpression or underexpression of one or more miRNAs prior to administration.

Definitions

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Green and Sambrook et al. Molecular Cloning: A Laboratory Manual, 4th ed., Cold Spring Harbor Laboratory Press, Cold Spring Harbor, N.Y. (2012) and Ausubel, ed., Current Protocols in Molecular Biology, John Wiley Interscience, (1990-2018)), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

The term "polynucleotide" refers to polymers composed of deoxyribonucleotides, ribonucleotides or any combination thereof.

As used herein, the term "nucleotide" refers to a chemical moiety having a sugar (modified, unmodified, or an analog thereof), a nucleotide base (modified, unmodified, or an analog thereof), and a phosphate group (modified, unmodified, or an analog thereof). Nucleotides include deoxyribonucleotides, ribonucleotides, and modified nucleotide analogs including, for example, locked nucleic acids ("LNAs"), peptide nucleic acids ("PNAs"), L-nucleotides, ethylene-bridged nucleic acids ("EN As"), arabinoside, and nucleotide analogs (including abasic nucleotides). Similarly, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. RNA may be used in the methods described herein and/or may be converted to cDNA by reverse-transcription and/or RNA for use in the methods described herein.

As used herein interchangeably, a "microRNA," "miR," or "miRNA" refer to the unprocessed or processed RNA transcript from a miRNA gene. The unprocessed miRNA gene transcript is also called a "miRNA precursor," and typically comprises an RNA transcript of about 70-100 nucleotides in length. The miRNA precursor can be processed by digestion with an RNAse (for example, Dicer, Argonaut, or RNAse III) into an active 19-25 nucleotide RNA molecule. This active 19-25 nucleotide RNA molecule is also called the "processed" miRNA gene transcript or "mature" miRNA.

The terms "pre-microRNA" or "pre-miR" or pre-miRNA" interchangeably refer to an RNA hairpin comprising within its polynucleotide sequence at least one mature micro RNA sequence and at least one dicer cleavable site.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., the tRNA, pre-microRNA and tRNA/microRNA hybrid polynucleotide molecules described herein, e.g, SEQ ID NOs:1-64 when compared and aligned for maximum correspondence over a comparison window, or designated region as measured using a sequence comparison algorithms (e.g., BLAST, ALIGN, FASTA or any other known alignment algorithm) or by manual alignment and visual inspection. Such sequences are then said to be "substantially identical." This definition also refers to the compliment of a test sequence. Preferably, the identity exists over a region that is at least about 10, 15, 20, 25, 35, 40, 45, 50, 60, 70, 80, 90, 100, 110, 120 nucleotides in length, or over the full-length of a reference sequence.

As used herein, the term "short interfering nucleic acid" or "siRNA" refers to any nucleic acid molecule capable of down regulating {i.e., inhibiting) gene expression in a mammalian cells (preferably a human cell). siRNA includes without limitation nucleic acid molecules that are capable of mediating sequence specific RNAi, for example short interfering RNA (siRNA), double-stranded RNA (dsRNA), micro-RNA (miRNA), and short hairpin RNA (shRNA). Likewise, the term "sense region" refers to a nucleotide sequence of a siRNA molecule complementary (partially or fully) to an antisense region of the siRNA molecule. Optionally, the sense strand of a siRNA molecule may also include additional nucleotides not complementary to the antisense region of the siRNA molecule. Conversely, as used herein, the term "antisense region" refers to a nucleotide sequence of a siRNA molecule complementary (partially or fully) to a target nucleic acid sequence. Optionally, the antisense strand of a siRNA molecule may include additional nucleotides not complementary to the sense region of the siRNA molecule.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against the ncRNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of any one or more of transcription of a microRNA, siRNA, piRNA, snRNA, lncRNA, antisense nucleic acid, or mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

A "target site" or "target sequence" is the nucleic acid sequence recognized (i.e., sufficiently complementary for hybridization) by an antisense oligonucleotide or inhibitory RNA molecule.

As used herein, the term "subject" refers to a mammal, such as a human, but can also be another animal such as a non-human primate, a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a subject who is, or is suspected to be, afflicted with a disease.

As used herein, the terms "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions described herein can also be administered in combination with one or more additional therapeutic compounds.

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for the preferential targeting of a pharmacological agent to the cancer cell. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Illustrative cell surface tumor markers for HCC include without limitation, EpCam, VEGF, FLT1, theophylline, malachite green, HCC-22-5 tumor-associated antigen (Zhou, et al., Clin Chim Acta. 2006 April; 366(1-2):274-80) and KRT23, AHSG and FTL antigens (Wang, et al., Cancer Lett. 2009 Aug. 28; 281(2):144-50). Aptamers that specifically bind HCC tumor associated antigens can be included in the hybrid tRNA-pre-miRNA molecules described herein.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced, e.g., in comparison to the tumor burden prior to administration of a hybrid tRNA/pre-miRNA molecule, as described herein, optionally in combination with a chemotherapeutic or anticancer agent. In some embodiments, the growth, progression or spread of a tumor or cancer is inhibited, reduced or decreased by at least about 1-fold, 2-fold, 3-fold, 4-fold, or more in comparison to the tumor burden prior to administration of the hybrid tRNA/pre-miRNA molecule, optionally in combination with a chemotherapeutic or anticancer agent.

BRIEF DESCRIPTION OF THE DRAWINGS

FIGS. 10A-F illustrate that LPP/let-7c nanotherapeutics largely reduces tumor growth in orthotopic HCC Huh7 xenograft mouse models. (A) Timeline of establishment of HCC xenograft mouse models and drug treatment. (B) Suppression of orthotopic HCC progression by LPP/let-7c was demonstrated by live animal imaging of luciferase bioluminescent signals. In vivo-jetPEI (IPEI)-formulated let-7c and MSA were used for comparison. (C) Ex vivo GFP fluorescence images of HCC-bearing livers further demonstrated the effectiveness of let-7c, which was associated with high levels of tumoral let-7c (D). (E) Serum AFP levels were significantly reduced in let-7c treated mice. (F) Representative H&E staining of tumor-bearing liver tissues and quantitative measurement of the percentage of tumor areas in corresponding liver slices. Areas circled in blue lines are necrotic areas, and the red lines are applied to distinguish tumors from healthy liver (L) tissues. Values are mean±SD (N=4-6 in each group). *P<0.05 and ***P<0.001 (1- or 2-way ANOVA with Bonferroni's post-hoc test).

FIGS. 11A-F illustrate treatments are well tolerated in orthotopic HCC xenograft mice, as indicated the lack of differences in animal body weights during therapy (A) as well as blood chemistry profiles including blood urea nitrogen (BUN; B), creatinine (C), alanine transaminase (ALT; D), aspartate transaminase (AST; E). Interestingly, total bilirubin (F) levels were high in untreated and MSA-treated mice, whereas they are within normal range in let-7c-treated mice. Values are mean±SD (N=4-6 in each group). The ranges of individual blood chemistry biomarkers (derived from BALB/c mice; Comparative Pathology Laboratory at UC-Davis) were marked as references.

FIGS. 13A-C illustrate that LPP/let-7c has no or limited impact on cytokine release in human PBMCs (A) and two stains of immunocompetent mice (B and C). LPS was used as positive control to induce cytokine release storm while untreated and LPP vehicle-treated mice or cells were considered as negative controls. Values are mean±SD. For Balb/c and CD-1 mice, 3 females and 3 males were included in each group (N=6). Bloods were harvested 1 h post treatment and serum samples were prepared for cytokine measurement. For human PBMCs, each treatment was conducted in triplicate (N=3), and cell culture medium was collected 24 h post treatment. n.d., non-detectable. P<0.01 and *P<0.001 (2-way ANOVA with Bonferroni's post-hoc test).

DETAILED DESCRIPTION

1. Introduction

Figure 1A:
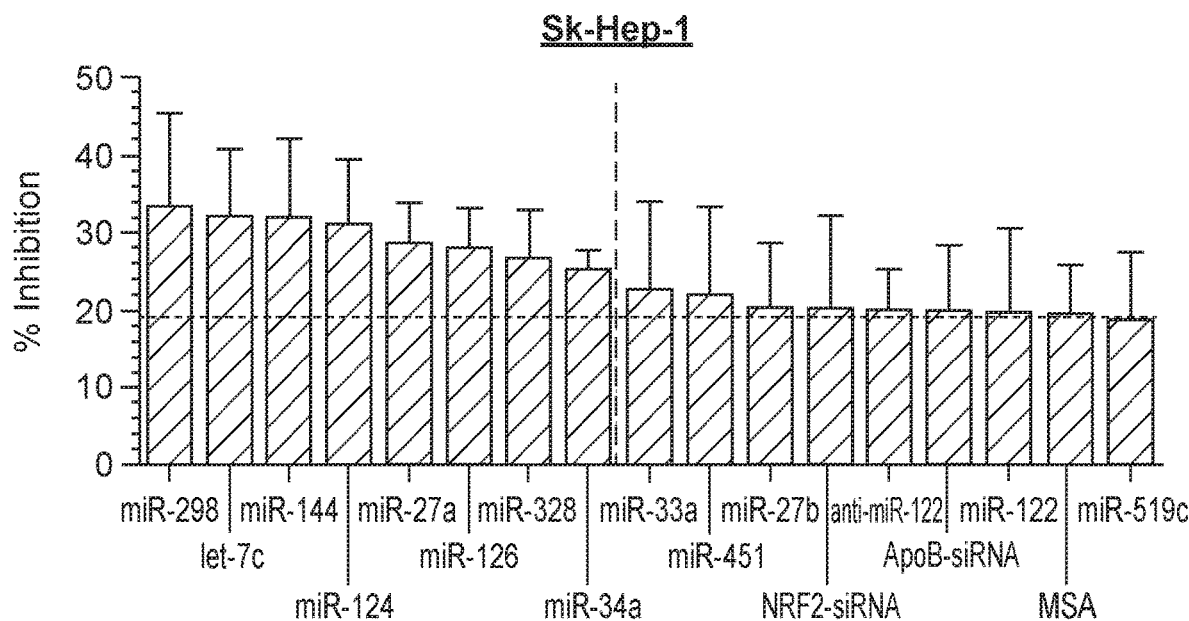
FIGS. 1A-C illustrates bioengineered let-7c is identified as the most potent inhibitor against HCC cell proliferation among a small collection of ncRNAs. (A) Antiproliferative activities of a collection of bioengineered ncRNA agents (5 nM) against luciferase/GFP-expressing Sk-Hep-1 and Huh7 cells were examined by luminometric ATP assay. Values were normalized to transfection reagent/vehicle control (0% Inhibition). (B) Dose-response curves of the top ranked ncRNA agents were further determined and (C) their pharmacodynamic parameters were estimated, which indicate that let-7c is the most potent inhibitor of HCC cell viability in this collection of ncRNA agents. Values are mean±SD (N=3 per group). *P<0.05, compared to MSA control.
Figure 1A:
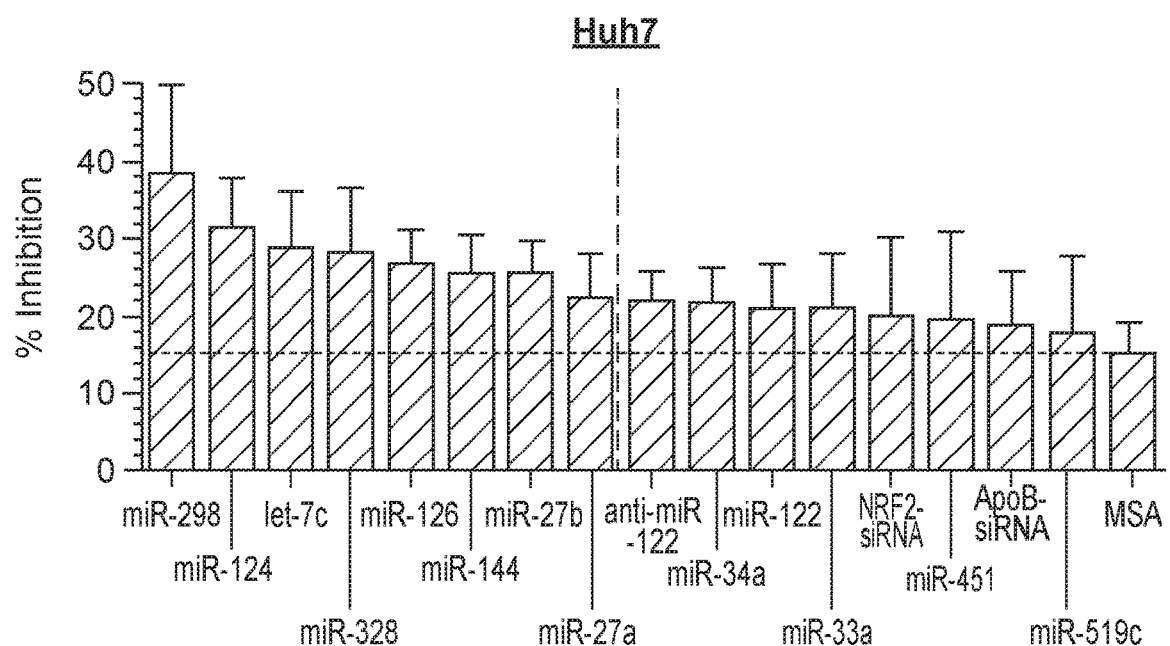

Hepatocellular carcinoma (HCC) remains a leading cause of cancer-related deaths and warrants more effective therapies. Restoration of multi-targeting microRNA (miRNA) depleted in HCC represents a new therapeutic strategy. In this study, we sought to identify potent miRNA agent that could alleviate HCC tumor burden and improve survival. Among a collection of unique bioengineered non-coding RNA molecules purified from bacterial fermentation, we have identified let-7c agent as the most potent inhibitor against both Huh7 and Sk-Hep-1 cell proliferation in vitro. We present further studies to demonstrate the mechanistic actions of bioengineered let-7c in selective modulation of target gene expression (Lin28B, ARID3B, Bcl-xl, and c-Myc), induction of apoptosis, and inhibition of tumor-sphere growth. Biologic let-7c formulated with liposomal-branched polyethylenimine (PEI) polyplex (LPP) exhibited much higher serum stability than in vivo-jetPEI (IPEI). Furthermore, LPP/let-7c nanotherapeutics was revealed to be more effective than IPEI/let-7c in the control of tumor progression in orthotopic HCC Huh7 xenograft mouse models, manifested by a more ubiquitous and greater degree of reduction of tumor burden determined by live animal and ex vivo tissue imaging as well as histopathological examination and blood chemistry profiling (e.g., α-fetoprotein and bilirubin levels). In addition, LPP/let-7c significantly extended overall survival of orthotopic HCC mice, whereas elicited no or minimal immune responses in immunocompetent mice and human peripheral blood mononuclear cells. Herein, we present our findings on the identification of bioengineered let-7c as the most potent inhibitor against HCC cell proliferation among a small collection of recombinant ncRNA agents. Following the delineation of mechanistic actions of let-7c on target gene expression as well as HCC cell stemness and apoptosis, our results demonstrate the utility of LPP/let-7c nanotherapeutics to reduce tumor progression and improve overall survival in orthotopic HCC xenograft mouse models. In addition, LPP/let-7c treatment is well tolerated in mice, showing no or minimal immunogenicity in human peripheral blood mononuclear cells (PBMCs) and two different strains of immunocompetent mice.: These results demonstrate that bioengineered let-7c is a useful molecule for the treatment of advanced HCC and LPP is a superior modality for in vivo RNA delivery.

2. Hybrid tRNA-miRNA Molecules for Use in Treating Hepatocellular Carcinoma (HCC)

tRNA/Pre-microRNA Scaffolds

Generally, the polynucleotides comprise a tRNA operably linked to a pre-microRNA. In some embodiments, the anticodon of the tRNA is replaced with a pre-microRNA molecule. For example, in some embodiments, the 3'-terminus and the 5'-terminus of the pre-microRNA are ligated or fused to the 3'-terminus and the 5'-terminus of the tRNA that are created when the anticodon is removed. The tRNA molecule and the pre-microRNA molecule can be, but need not be directly ligated or fused to one another to be operably linked. In some embodiments, the pre-microRNA can contain one or more dicer cleavable sites to allow for the high level expression and efficient cleavage of an inserted RNA molecule desired to be expressed from the hybrid tRNA/pre-microRNA polynucleotide. tRNA/pre-microRNA scaffolds are described, e.g., in Intl. Publ. No. WO 2015/183667, which is hereby incorporated herein by reference in its entirety for all purposes.

The hybrid tRNA/pre-microRNA molecules can be produced by standard recombinant methods, or can be synthetically prepared. In some embodiments, the polynucleotides can have one or more chemical modifications, including without limitation, e.g., internucleotide linkages, internucleoside linkages, dideoxyribonucleotides, 2'-sugar modification, 2'-amino groups, 2'-fluoro groups, 2'-methoxy groups, 2'-alkoxy groups, 2'-alkyl groups, 2'-deoxyribonucleotides, 2'-O-methyl ribonucleotides, 2'-deoxy-2'-fluoro ribonucleotides, universal base nucleotides, acyclic nucleotides, 5-C-methyl nucleotides, biotin groups, terminal glyceryl incorporation, inverted deoxy abasic residue incorporation, sterically hindered molecules, 3'-deoxyadenosine (cordycepin), 3'-azido-3'-deoxythymidine (AZT), 2',3'-dideoxyinosine (ddl), 2',3'-dideoxy-3'-thiacytidine (3TC), 2',3'-didehydro-2',3'-dideoxythymidi-ne (d4T), monophosphate nucleotide modification (MNM) of 3'-azido-3'-deoxythymidine (AZT), MNM-2',3'-dideoxy-3'-thiacytidine (3TC), MNM-2',3'-didehydro-2',3'-dide-oxythymidine (d4T), capping moieties, L-nucleotides locked nucleic acid (LNA) nucleotides, 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, 2'-O-methyl, cholesterol groups, 2'-O-methyl groups, phosphorothioate groups, 2'-fluoro groups, 2'-O-methyoxyethyl groups, boranophosphate groups, 4'-thioribose groups, bile acid, lipids, and bridges connecting the 2'-oxygen and 4'-carbon.

In some embodiments, the hybrid tRNA/pre-microRNA molecules comprise analog ribonucleotide bases. As used herein, the term "analog" defines possible derivatives of the ribonucleotide originating from the activity of tRNA post-transcriptional modification enzymes of the cell in which they are produced. The analogs of the ribonucleotides A, C, G and U which may be found in a tRNA depend on the cell in which that tRNA is produced and on the position of the ribonucleotide in question in the tRNA. A large number of analogs are given in Sprinzl et al. (1998) "Compilation of tRNA sequences and sequences of tRNA genes". Nucleic Acids Res., 26, 148-153 and on the basis of "RNA modification database" data (http://medstat.med.utah.edu/RNAmods/). The analogs of A may be selected more particularly from the group constituted by 1-methyl-A, inosine and 2'-O-methyl-A. The analogs of C may be selected more particularly from the group constituted by 5-methyl-C and 2'-O-methyl-C. The analogs of G may be selected more particularly from the group constituted by 7-methyl-G and 2'-O-methyl-G. The analogs of U may be selected more particularly from the group constituted by pseudouridine, ribothymidine, 2'-O-methyl-ribothymidine, dihydrouridine, 4-thiouridine and 3-(3-amino-3-carboxypropyl)-uridine.

a. tRNA

The general characteristics of a tRNA are well-known to the person skilled in the art. In some embodiments, a tRNA is formed of a single ribonucleotide chain which is capable of folding to adopt a characteristic, so-called cloverleaf secondary structure. This characteristic secondary structure comprises:

(i) an acceptor stem composed of the first 7 ribonucleotides of the 5' end of the ribonucleotide chain and the 7 ribonucleotides that precede the last 4 ribonucleotides of the 3' end of the ribonucleotide chain, thus forming a double-stranded structure comprising 6 or 7 pairs of ribonucleotides, it being possible for the ribonucleotides constituted by the first ribonucleotide of the 5' end of the ribonucleotide chain and the ribonucleotide that precedes the last 4 ribonucleotides of the 3' end of the ribonucleotide chain not to be paired;

(ii) a D arm constituted by 4 pairs of ribonucleotides and a D loop constituted by 8 to 10 ribonucleotides, formed by the folding of a part of the ribonucleotide chain that follows the first 7 ribonucleotides of the 5' end of the ribonucleotide chain;

(iii) a stem of the anticodon constituted by 5 pairs of ribonucleotides, and a loop of the anticodon constituted by 7 ribonucleotides (stem-loop of the anticodon), formed by the folding of a part of the ribonucleotide chain that follows the D arm and the D loop;

(iv) a variable loop constituted by from 4 to 21 ribonucleotides and formed by a part of the ribonucleotide chain that follows the stem of the anticodon and the loop of the anticodon;

(v) a T arm constituted by 5 pairs of ribonucleotides, and a T loop constituted by 8 ribonucleotides, formed by the folding of a part of the ribonucleotide chain that follows the variable loop and precedes the ribonucleotides of the 3' end of the ribonucleotide chain which are involved in the constitution of the acceptor stem.

The hybrid tRNA/pre-microRNA polynucleotides can contain any tRNA known in the art, e.g., for encoding any amino acid. The selection of an appropriate tRNA molecule may be, in part, driven by the host cells to be used for expression of the inserted RNA. For example, when seeking to produce high expression levels of a desired inserted RNA molecule, the tRNA selected can be from a tRNA encoding for codon preferred by the species of host cell rather than from a rare codon in that species of host cell. In some embodiments, the tRNA codes for a leucine, serine, glutamine, lysine, cysteine or methionine. In some embodiments, the tRNA is derived from the host cell used for expression. In some embodiments, the tRNA is a mammalian tRNA. In some embodiments, the tRNA is a human tRNA.

In some embodiments, the chimeric tRNA defined above does not comprise the substantially intact stem of the anticodon of the tRNA from which it is derived. For example, in the chimeric tRNA, between the ribonucleotide that precedes the stem-loop of the anticodon in the tRNA before modification and the ribonucleotide that follows the stem-loop of the anticodon in the tRNA before modification, the stem of the anticodon of the tRNA before modification is no longer present.

b. pre-microRNA

The hybrid tRNA/pre-microRNA polynucleotides can contain one or more of any pre-microRNA molecule known in the art, and can be obtained from naturally occurring sources (e.g., pre-miRNAs or miRNAs), or artificially derived (e.g., shRNAs). In some embodiments, the one or more pre-microRNA components are selected from human pre-miRNA-1291 (MI0006353), human pre-miRNA-34a (MI0000268), human pre-miRNA-125 (MI0000469, MI0000446, MI0000470), human pre-miRNA-124 (MI0000443, MI0000444, MI0000445), human pre-miRNA-27b (MI0000440), human pre-miRNA-22 (MI0000078), pre-let-7c (MI0000064), pre-miR-328 (MI0000804), pre-miR-126 (MI0000471), pre-miR-298 (MI0005523) and pre-miR-200 (MI0000342, MI0000650, MI0000737), and mutants or variants thereof, e.g., having at least about 90%, 91%, 92%, 93%, 94%, 95%, 96%, 97%, 98%, 99% or 100% sequence identity to the reference sequence. See, e.g., pre-microRNAs listed on miRBase.org. In some embodiments, the pre-microRNA is a stabilized pre-miRNA-34a, e.g., having at least about 90%, 91%, 92%, 93%, 94%, 95%, 96%, 97%, 98%, 99% or 100% sequence identity to SEQ ID NOs:1-6. In some embodiments, the pre-microRNA has at least about 90%, 91%, 92%, 93%, 94%, 95%, 96%, 97%, 98%, 99% or 100% sequence identity to SEQ ID NOs:1-46. Other pre-microRNA molecules that can be used in the hybrid tRNA/pre-microRNA polynucleotides include pre-microRNA molecules that express in the host cell (e.g., E. coli host cell) at or above the levels of expression of human (hsa) pre-miRNA-1291, human pre-miRNA-34a, human pre-miRNA-125-1, human pre-miRNA-124, human pre-miRNA-27b, human pre-miRNA-22, in the same host cell (e.g., E. coli host cell). In hybrid tRNA/pre-miRNA scaffolds that have two or more pre-miRNA molecules, the first and subsequent (e.g., second, third, fourth, etc.) pre-miRNA molecules can be the same or different. In some embodiments, the pre-microRNA molecule is from a mammalian pre-microRNA molecule. In some embodiments, the pre-microRNA molecule is from a human pre-microRNA molecule. In some embodiments, the pre-microRNA component of the hybrid tRNA/pre-microRNA polynucleotides is from about 80 nucleotides to about 120 nucleotides in length, e.g., from about 80 nucleotides to about 100 nucleotides in length, e.g., about 80, 85, 90, 95, 100, 105, 110, 115 or 120 nucleotides in length.

c. Inserted RNA Molecules

In some embodiments, the hybrid tRNA/pre-microRNA molecules contain an inserted RNA sequence and serve as a scaffold for the high-level production of the inserted RNA sequence, which can be cleaved from the hybrid tRNA/pre-microRNA molecule, e.g., by an endoribonuclease, e.g., by Dicer. In some embodiments, the inserted RNA molecule can be from about 18 nucleotides and up to about 200 nucleotides, e.g., at least about 18 nucleotides and up to about 150 nucleotides, e.g., at least about 18 nucleotides and up to about 125 nucleotides, e.g., at least about 18 nucleotides and up to about 100 nucleotides, e.g., at least about 18 nucleotides and up to about 75 nucleotides, e.g., at least about 18 nucleotides and up to about 50 nucleotides, e.g., at least about 18 nucleotides and up to about 40 nucleotides, e.g., at least about 18 nucleotides and up to about 30 nucleotides. In some embodiments, the inserted RNA molecule can be about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

As appropriate or desired, the inserted RNA can be an inhibitory nucleic acid, that prevents, reduces or inhibits the transcription or translation of a target nucleic acid or protein. In some embodiments, the inhibitory nucleic acid is a noncoding RNA (ncRNA), mature microRNA (miRNA), a small interfering RNA (siRNA), a short hairpin RNA (shRNA), a Piwi-interacting RNA (piRNA), a small nuclear RNA (snRNA), or a small nucleolar RNA (snoRNA). In some embodiments, the inserted RNA is a mature miRNA, e.g., that is derived from (e.g., is homologous to) or is heterologous to the pre-microRNA molecule in the hybrid tRNA/pre-microRNA scaffold. In some embodiments, the inserted RNA is a mature miRNA, e.g., a human mature miRNA, selected from the group consisting of let-7c (MI0000064), miR-298 (MI0005523), miR-216 (MI0000292, MI0005569), miR-124 (MI0000443, MI0000444, MI0000445), miR-328 (MI0000804), miR-144 (MI0000460), miR-126 (MI0000471), miR-16 (MI0000070, MI0000115), miR-18 (MI0000072; MI0001518), miR-125a (MI0000469), miR-195 (MI0000489), miR-199a (MI0000242, MI0000281), miR-200 (MI0000342, MI0000650, MI0000737), and miR-224 (MI0000301). In some embodiments, the inserted RNA is a noncoding RNA. See, e.g., microRNAs listed on miRBase.org.

3. Formulation and Administration

The hybrid tRNA/pre-microRNA scaffolds can be administered to a subject in need thereof (e.g., a subject diagnosed as having hepatocellular carcinoma) for delivery of an inserted RNA of interest (e.g., an inhibitory nucleic acid, an aptamer) to interior of a target cell. Generally, the subject is a mammal and therefore comprises eukaryotic cells which express endoribonucleases (e.g., Dicer). Once the target eukaryotic cells of the subject have been transfected or transformed with the hybrid tRNA/pre-microRNA scaffolds, the endoribonucleases (e.g., Dicer) within the target cell cleave out or release the inserted RNA of interest.

In some embodiments, the inserted RNA is an inhibitory nucleic acid (e.g., a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), an aptamer). In some embodiments, the inhibitory RNA once released from the hybrid scaffold in a eukaryotic cell reduces the amount and/or activity of the target nucleic acid or polypeptide by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%.

In certain embodiments, the hybrid tRNA/pre-microRNA scaffolds are expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application in a general, illustrative sense, and are not intended to limit the invention.

In one embodiment, an expression vector for expressing the hybrid tRNA/pre-microRNA scaffolds comprises a promoter "operably linked" to a polynucleotide encoding the hybrid tRNA/pre-microRNA scaffolds (e.g., containing an inserted RNA). The phrase "operably linked" or "under transcriptional control" as used herein means that the promoter is in the correct location and orientation in relation to a polynucleotide to control the initiation of transcription by RNA polymerase and expression of the polynucleotide.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Illustrative promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences include UTRs which include an Internal Ribosome Entry Site (IRES) present in the leader sequences of picornaviruses such as the encephalomyocarditis virus (EMCV) UTR (Jang et al. J. Virol. (1989) 63:1651-1660. Other picornavirus UTR sequences that will also find use include the polio leader sequence and hepatitis A virus leader and the hepatitis C IRES.

There are a number of ways in which expression vectors may be introduced into cells. In certain embodiments, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the available methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice. The adenovirus may be of any of the 42 different known serotypes or subgroups A-F. Adenovirus type 5 of subgroup C is the preferred starting material in order to obtain the conditional replication-defective adenovirus vector for use. This is because Adenovirus type 5 is a human adenovirus about which a great deal of biochemical and genetic information is known, and it has historically been used for most constructions employing adenovirus as a vector.

The typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing the hybrid tRNA/pre-microRNA scaffolds (e.g., containing an inserted RNA) in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect cleavage and expression of inserted RNA, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Porter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the hybrid tRNA/pre-microRNA scaffolds, e.g., containing the inserted RNA of interest, may be positioned and expressed at different sites. In certain embodiments, the nucleic acid encoding the hybrid tRNA/pre-microRNA scaffolds may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In some embodiments, the hybrid tRNA/pre-miRNA construct is packaged within and delivered in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ohosh and Bachhawat, 1991). Also contemplated are lipofectamine-DNA complexes. In one embodiment, the hybrid tRNA/pre-miRNA construct is complexed with a polyethylenimine (PEI), e.g., liposomal-branched polyethylenimine (PEI) polyplex (LPP) or in vivo-jetPEI (IPEI). In some embodiments, the tRNA/pre-miRNA construct is complexed with a branched polyethylenimine have an average molecular weight of about 10,000 Da. The complex can then be encapsulated in a lipid bilayer, e.g., comprising a mixture of 1,2-di-O-octadecenyl-3-trimethylammonium propane (DOTMA), cholesterol and 1,2-Dimyristoyl-sn-glycerol, methoxypolyethylene glycol (DMG-PEG2000).

In certain embodiments, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-I) (Kato et al., 1991). In yet further embodiments, the liposome may be complexed or employed in conjunction with both HVJ and HMG-I. In that such expression constructs have been successfully employed in transfer and expression of nucleic acid in vitro and in vivo, then they are applicable. Where a bacterial promoter is employed in the DNA construct, it also will be desirable to include within the liposome an appropriate bacterial polymerase.

Other expression constructs which can be employed to deliver a nucleic acid encoding a particular lncRNA or inhibitor into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise an encapsulating particle and an external targeting ligand, e.g., that specifically binds to a tumor associated antigen. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. Illustrative tumor-associated or surface antigens for delivering the hybrid tRNA/pre-miRNA constructs to HCC cells include without limitation, EpCam, VEGF, fms related tyrosine kinase 1 (FLT1), theophylline, malachite green, HCC-22-5, keratin 23 (KRT23), alpha 2-HS glycoprotein (AHSG) and ferritin light chain (FTL). Other TAAs are known and find use for the formulation and targeted delivery of the hybrid tRNA/pre-microRNA scaffolds.

In a particular example, the oligonucleotide may be administered in combination with a cationic lipid. Examples of cationic lipids include, but are not limited to, lipofectin, DOTMA, DOPE, and DOTAP. The publication of WO00/71096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Also encompassed are pharmaceutical compositions comprising the hybrid tRNA/pre-microRNA scaffolds and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the hybrid tRNA/pre-microRNA scaffolds described herein. Commercially available fat emulsions that are suitable for delivering the nucleic acids to tissues, such as cardiac muscle tissue and smooth muscle tissue, include Intralipid, Liposyn, Liposyn II, Liposyn III, Nutrilipid, and other similar lipid emulsions. One colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

One will generally desire to employ appropriate salts and buffers to render delivery vehicles stable and allow for uptake by target cells. Buffers also will be employed when recombinant cells are introduced into a patient. Aqueous compositions can comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the hybrid tRNA/pre-miRNA scaffolds, its use in therapeutic compositions is contemplated. Supplementary active ingredients also can be incorporated into the compositions, provided they do not inactivate the nucleic acids of the compositions.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous, intrahepatic, intratumoral and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15$^{th}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

The skilled artisan will be able to select and use an appropriate system for delivering the inhibitory nucleic acid or an expression vector to target cells in vitro or in vivo without undue experimentation.

The hybrid tRNA/pre-microRNA scaffolds (e.g., containing an inserted RNA) may be administered to a subject with cancer to enhance or increase the responsiveness to chemotherapy comprising a platinum coordination complex. In alternative embodiments, the cancer is resistant to treatment with a chemotherapy regime. By "resistant to chemotherapy" is meant that the cancer does not substantially respond to treatment with the chemotherapy. Identification of such resistant cancers and cancer In some embodiments, the hybrid tRNA/pre-microRNA scaffolds (e.g., containing an inserted RNA) may be used to treat subjects who have failed (relapsed) after standard chemotherapy or bone marrow transplantation or other emerging or novel targeted therapies. By "treat," "treatment" or "treating" is meant ameliorating symptoms associated with cancer, including preventing or delaying the onset of the disease symptoms and/or lessening the severity or frequency of the disease symptoms and/or prolonging remission and/or decreasing the frequency or severity of relapse. In some embodiments, the hybrid tRNA/pre-microRNA scaffolds (e.g., containing an inserted RNA) can be administered to the subject in conjunction with chemotherapy comprising a platinum coordination complex (e.g., prior to or concurrently with chemotherapy comprising a platinum coordination complex.

The hybrid tRNA/pre-microRNA scaffolds (e.g., containing an inserted RNA) may be provided alone or in combination with other compounds (for example, chemotherapeutics), in the presence of a liposome, an adjuvant, or any pharmaceutically acceptable carrier, in a form suitable for administration to mammals, for example, humans, cattle, sheep, etc. If desired, treatment with the hybrid tRNA/pre-microRNA scaffolds (e.g., containing an inserted RNA) may be combined with traditional and existing, or emerging, therapies for cancer, e.g., targeted chemotherapies using cancer-specific peptides described, e.g., in Intl. Publ. No. 2011/038142.

The hybrid tRNA/pre-microRNA scaffolds (e.g., containing an inserted RNA) may be administered chronically or intermittently. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature. In alternative embodiments, the hybrid tRNA/pre-microRNA scaffolds (e.g., containing an inserted RNA) are administered to a subject in need of such inhibitors, e.g., a subject diagnosed with or suspected of having a cancer.

In alternative embodiments, a hybrid tRNA/pre-microRNA scaffold (e.g., containing an inserted RNA) may be effectively delivered to cancer cells, by a variety of methods known to those skilled in the art. Such methods include but are not limited to liposomal encapsulation/delivery, vector-based gene transfer, fusion to peptide or immunoglobulin sequences (peptides described, e.g., in Intl. Publ. No. 2011/

038142) for enhanced cell targeting and other techniques. Suitable viral vectors include retroviral vectors such as lentiviral vectors, adenovirus vectors, adeno-associated virus vectors, etc. In alternative embodiments, a hybrid tRNA/pre-microRNA scaffold (e.g., containing an inserted RNA), may also be formulated in pharmaceutical compositions well known to those in the field. These include liposomal formulations and combinations with other agents or vehicles/excipients such as cyclodextrins which may enhance delivery of the inhibitory nucleic acid. In alternative embodiments, suitable carriers include lipid-based carriers such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In alternative embodiments, the carrier system is a cyclodextrin-based carrier system such as a cyclodextrin polymer-nucleic acid complex. In further embodiments, the carrier system is a protein-based carrier system such as a cationic peptide-nucleic acid complex.

Suitable carriers are known in the art and are described in, without limitation, United States Patent Application Nos. 20070173476 published Jul. 26, 2007; 20050008617 published Jan. 13, 2005; 20050014962 published Jan. 20, 2005; 20050064595 published Mar. 24, 2005; 20060008910 published Jan. 12, 2006; 20060051405 published Mar. 9, 2006; 20060083780 published Apr. 20, 2006; 20050008689 published Jan. 13, 2005; 20070172950 published Jul. 26, 2007; U.S. Pat. No. 7,101,995 issued Sep. 5, 2006 to Lewis, et al.; U.S. Pat. No. 7,220,400 issued May 22, 2007, to Monahan, et al.; U.S. Pat. No. 5,705,385 issued Jan. 6, 1998 to Bally, et al.; U.S. Pat. No. 5,965,542 issued Oct. 12, 1999 to Wasan, et al.; U.S. Pat. No. 6,287,591 issued Sep. 11, 2001 to Semple, et al., all of which are hereby incorporated by reference.

In one embodiment, a nucleic acid-lipid particle comprising a hybrid tRNA/pre-microRNA scaffold (e.g., containing an inserted RNA) is provided. In addition to the references described above, suitable nucleic acid-lipid particles and their use are described in U.S. Pat. Nos. 6,815,432, 6,586,410, and 6,534,484.

Conventional pharmaceutical practice may be employed to provide suitable formulations or compositions to administer the hybrid tRNA/pre-microRNA scaffolds (e.g., containing an inserted RNA) to subjects suffering from, at risk of, or presymptomatic for cancer. Suitable pharmaceutical compositions may be formulated by means known in the art and their mode of administration and dose determined by the skilled practitioner. Any appropriate route of administration may be employed, for example, parenteral, intravenous, subcutaneous, intramuscular, intraventricular, intraurethral, intraperitoneal, intrahepatic, intratumoral, intranasal, aerosol, oral administration, or any mode suitable for the selected treatment. Therapeutic formulations may be in the form of liquid solutions or suspensions. For enteral administration, the compound may be administered in a tablet, capsule or dissolved in liquid form. The table or capsule may be enteric coated, or in a formulation for sustained release. For intranasal formulations, in the form of powders, nasal drops, or aerosols. For parenteral administration, a hybrid tRNA/pre-microRNA scaffold (e.g., containing an inserted RNA) may be dissolved in sterile water or saline or a pharmaceutically acceptable vehicle used for administration of non-water soluble hybrid tRNA/pre-microRNA scaffold (e.g., containing an inserted RNA) such as those used for vitamin K Suitable formulations include those that have desirable pharmaceutical properties, such as targeted delivery to cancer cells, improved serum half-life/stability of a hybrid tRNA/pre-microRNA scaffold (e.g., containing an inserted RNA), improved intracellular penetration and cytoplasmic delivery, improved persistence of in-vivo activity, reduction in dose required for efficacy, reduction in required dosing frequency, etc. In alternative embodiments, a liposomal nanoparticle-based dosing formulation of a hybrid tRNA/pre-microRNA scaffold (e.g., containing an inserted RNA) may be prepared using methods well known to those skilled in the art and currently practiced for the preparation pharmaceutical formulations of other oligonucleotide-based reagents/therapeutics including anti-sense oligonucleotides and/or RNAi (siRNA)-based agents. In alternative embodiments, a gene therapy approach for transduction of hybrid tRNA/pre-microRNA scaffolds (e.g., containing an inserted RNA) to target cells (e.g., cancer cells) using for example lentiviral-based vectors, may be used.

Methods well known in the art for making formulations are found in, for example, Remington: the Science & Practice of Pharmacy, Loyd, et al., eds., $22^{nd}$ ed., Pharmaceutical Press, (2012). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the hybrid tRNA/pre-microRNA scaffolds (e.g., containing an inserted RNA) are administered to an individual in an amount sufficient to stop or slow a cancer, or to promote differentiation, or inhibit or decrease self-renewal, or inhibit or decrease engraftment or metastasis of cancer cells.

An "effective amount" of a hybrid tRNA/pre-microRNA scaffold (e.g., containing an inserted RNA) includes a therapeutically effective amount or a prophylactically effective amount. A "therapeutically effective amount" refers to an amount effective, at dosages and for periods of time necessary, to achieve the desired therapeutic result, such as treatment of a cancer or promotion of differentiation, or inhibition or decrease of self-renewal or inhibition or decrease of engraftment or metastasis of a cancer cell. The increase or decrease may be between 10% and 90%, e.g., 10%, 20%, 30%, 40%, 50%, 60%, 70%, 80%, 90%, or may be over 100%, such as 200%, 300%, 500% or more, when compared with a control or reference subject, sample or compound.

A therapeutically effective amount of a hybrid tRNA/pre-microRNA scaffold (e.g., containing an inserted RNA) may vary according to factors such as the disease state, age, sex, and weight of the individual subject, and the ability of the hybrid tRNA/pre-microRNA scaffolds (e.g., containing an inserted RNA) to elicit a desired response in the individual. Dosage regimens may be adjusted to provide the optimum therapeutic response. A therapeutically effective amount is also one in which any toxic or detrimental effects of the hybrid tRNA/pre-microRNA scaffold (e.g., containing an inserted RNA) are outweighed by the therapeutically beneficial effects. A "prophylactically effective amount" refers to an amount effective, at dosages and for periods of time necessary, to achieve the desired prophylactic result, such as prevention or protection against a cancer or promotion of differentiation, inhibition or decrease of self-renewal or inhibition or decrease of engraftment or metastasis of cancer cells. Typically, a prophylactic dose is used in subjects prior to or at an earlier stage of disease, so that a prophylactically effective amount may be less than a therapeutically effective amount. In alternative embodiments, dosages may be adjusted depending on whether the subject is in remission from cancer or not. A preferred range for therapeutically or prophylactically effective amounts of a hybrid tRNA/pre-microRNA scaffolds (e.g., containing an inserted RNA) may be any integer from 0.1 nM-0.1M, 0.1 nM-0.05M, 0.05 nM-15 µM or 0.01 nM-10 µM. In alternative embodiments, a therapeutically or prophylactically effective amount that is administered to a subject may range from about 5 to about 3000 micrograms/kg if body weight of the subject, or any number therebetween.

In alternative embodiments, the hybrid tRNA/pre-microRNA scaffold (e.g., containing an inserted RNA) is provided in an amount that is from 10% to 99% greater than the amount of target nucleic acid or polypeptide present in cancer cells, or more generally at least 10%, 20%, 30%, 40%, 50, 55% or 60%, or at least 65%, 75%, 80%, 85%, 90%, or 95%, or as much as 96%, 97%, 98%, or 99% greater than the amount present in cancer cells. In alternative embodiments, the hybrid tRNA/pre-microRNA scaffold (e.g., containing an inserted RNA) is provided in an amount that is 0.5 to 50 fold greater than the amount present in cancer cells, or more generally at least 0.5, 1, 1.5, 2, 5, 10, 20, 25, 30, 35, 40, 45 fold greater than the amount present in cancer cells. In alternative embodiments, the hybrid tRNA/pre-microRNA scaffold (e.g., containing an inserted RNA) is provided in an amount that is equivalent to the amount present in non-cancerous bladder cells or the amount present in normal bladder cells.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

4. Chemotherapeutic or Anticancer Agents

In various embodiments, the hybrid tRNA/pre-microRNA molecule is co-administered with one or more chemotherapeutic or anticancer agents.

Examples of chemotherapeutic or anticancer agents that can be co-administered with the hybrid tRNA/pre-microRNA molecule are known in the art and include without limitation alkylating agent(s) (e.g., nitrogen mustards, nitrogen ureas, ethylenimines, methylmelamines, alkyl sulfonates, carmustine, triazenes), platinum-coordination complexes (e.g., cisplatin, carboplatin, and oxaliplatin), anti-metabolite(s) (e.g., folic acid analogs (e.g., methotrexate), pyrimidine analogs (e.g., capecitabine, 5-fluorouracil, 5-fluorodeoxyuridine, 5-fluorodeoxyuridine monophosphate, cytosine arabinoside, 5-azacytidine, gemcitabine), purine analogs (e.g., mercaptopurine, thioguanine, azathioprine, pentostatin, erythrohydroxynonyladenine, fludarabine, cladribine)), plant alkaloid(s) and/or terpenoid(s), vinca alkaloid(s) (e.g., vincristine, vinblastine, vinorelbine, and vindesine), podophyllotoxin(s) (e.g., etoposide and teniposide), camptothecin(s) (e.g., irinotecan and topotecan), anthracycline(s), aromatase inhibitor(s), taxane(s) (e.g., paclitaxel, taxol and docetaxel), topoisomerase inhibitor(s) (e.g., (Type I inhibitors: camptothecins, including irinotecan and topotecan; Type II Inhibitors: amsacrine, etoposide, etoposide phosphate, and teniposide), antibiotic(s) (e.g., dactinomycin, daunorubicin, doxorubincin, idarubicin, epirubicin, bleomycins, mitomycin), hormone(s), differentiating agent(s), kinase inhibitor(s) (e.g., Bevacizumab, BIBW 2992, Cetuximab, Imatinib, Trastuzumab, Gefitinib, Ranibizumab, Pegaptanib, Sorafenib, Dasatinib, Sunitinib, Erlotinib, Nilotinib, Lapatinib, Panitumumab, Vandetanib, E7080, Pazopanib, Mubritinib and Fostamatinib) and antineoplastic agent(s) (e.g., (dactinomycin, doxorubicin, epirubicin, fludarabine and bleomycin). Any chemotherapeutic or anticancer agent being used to treat the cancer of interest can be co-administered in a combination therapy regime with the hybrid tRNA/pre-microRNA molecule. Chemotherapeutic or anticancer agents of use are known in the art and described in reference texts, e.g., Physicians' Desk Reference, 71st Ed., 2017, PDR Network or Brunton and Knollmann, Goodman & Gilman's The Pharmacological Basis of Therapeutics, 13th edition, 2017, McGraw-Hill.

5. Methods of Monitoring

A variety of methods can be employed in determining efficacy of therapeutic and prophylactic treatment with a hybrid tRNA/pre-microRNA scaffold (e.g., containing an inserted RNA), e.g., in combination with a chemotherapeutic or anticancer agent. Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. The hybrid tRNA/pre-microRNA scaffold (e.g., containing an inserted RNA), e.g., in combination with a chemotherapeutic or anticancer agent can be screened for prophylactic or therapeutic efficacy in animal models in comparison with untreated or placebo controls. A hybrid tRNA/pre-microRNA scaffold (e.g., containing an inserted RNA), e.g., in combination with a chemotherapeutic or anticancer agent identified by such screens can be then analyzed for the capacity to induce tumor cell death or enhanced immune system activation. For example, multiple dilutions of sera can be tested on tumor cell lines in culture and standard methods for examining cell death or inhibition of cellular growth can be employed. (See, e.g., Green and Sambrook, Molecular Cloning: A Laboratory Manual, Cold Spring Harbor Laboratory Press; 4th edition (2012); Ausubel, et al. Editor, *Current Protocols in Molecular Biology*, USA, 1984-2018; and Ausubel, et al. Editor, *Current Protocols in Molecular Biology, USA,* 1984-2018; Bonifacino, et al., Editor, *Current Protocols in Cell Biology*, USA, through 2018; all of which are incorporated herein by reference in their entirety.)

The methods provide for detecting inhibition disease in patient suffering from or susceptible to various cancers. A variety of methods can be used to monitor both therapeutic treatment for symptomatic patients and prophylactic treatment for asymptomatic patients.

Monitoring methods entail determining a baseline value of a tumor burden in a patient before administering a dosage of a hybrid tRNA/pre-microRNA scaffold (e.g., containing an inserted RNA), e.g., in combination with a chemotherapeutic or anticancer agent, and comparing this with a value for the tumor burden after treatment, respectively.

With respect to therapies using a hybrid tRNA/pre-microRNA scaffold (e.g., containing an inserted RNA), e.g., in combination with a chemotherapeutic or anticancer agent, a significant decrease (i.e., greater than the typical margin of experimental error in repeat measurements of the same sample, expressed as one standard deviation from the mean of such measurements) in value of the tumor burden signals a positive treatment outcome (i.e., that administration of a hybrid tRNA/pre-microRNA scaffold (e.g., containing an inserted RNA), e.g., in combination with a chemotherapeutic or anticancer agent has blocked or inhibited, or reduced progression of tumor growth and/or metastasis).

In other methods, a control value of tumor burden (e.g., a mean and standard deviation) is determined from a control population of individuals who have undergone treatment with a hybrid tRNA/pre-microRNA scaffold (e.g., containing an inserted RNA), e.g., in combination with a chemotherapeutic or anticancer agent Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant decrease in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can be analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

Further, the level of immune system activity in conjunction with tumor burden in a patient before administering a dosage of a hybrid tRNA/pre-microRNA scaffold (e.g., containing an inserted RNA), e.g., in combination with a chemotherapeutic or anticancer agent, can be compared this with a value for the immune system activity in conjunction with tumor burden after treatment, again respectively.

With respect to therapies involving enhanced immune system activity, a significant increase (i.e., greater than the typical margin of experimental error in repeat measurements of the same sample, expressed as one standard deviation from the mean of such measurements) in value of immune response signals a positive treatment outcome (i.e., that administration of a hybrid tRNA/pre-microRNA scaffold (e.g., containing an inserted RNA), e.g., in combination with a chemotherapeutic or anticancer agent, has achieved or augmented an immune response) Immune response signals can include but are not limited to for example assessing the enhancement of the lymphoma-specific cytotoxic effect of human peripheral blood mononuclear cells (PBMCs). If the value for the immune response signal does not change significantly, or decreases, a negative treatment outcome is indicated. In general, patients undergoing an initial course of treatment with an immunogenic agent are expected to show an increase in immune response activity with successive dosages, which eventually reaches a plateau. Administration of an agent is often continued while the immune response is increasing. Once a plateau is obtained, that is an indicator if the treatment is solely for the immune the administration of the treatment can be discontinued or reduced in dosage or frequency.

6. Kits

Further provided are kits comprising one or more containers comprising the hybrid tRNA/pre-microRNA scaffolds (e.g., containing an inserted RNA for reducing or inhibiting growth of an HCC cell), including any of the polynucleotides, expression cassettes, liposomes or nanoparticles, or compositions described herein, and any combinations thereof. Kits containing multiple containers can have aliquots providing unitary doses of the hybrid tRNA/pre-microRNA molecules in a formulation suitable for administration, e.g., an aqueous solution comprising liposomes encapsulating the tRNA/pre-microRNA scaffolds.

In various embodiments, suitable formulations may be provided in a kit including one or more hybrid tRNA/pre-microRNA (e.g., containing an inserted RNA for reducing or inhibiting growth of an HCC cell), together with instructions for using the hybrid tRNA/pre-microRNA molecules to treat HCC. The kit may contain additional agents such as a pharmaceutical carrier e.g, a liposomal carrier or additional active ingredients such as a chemotherapeutic or anticancer agent. The additional agents may be provided in the same container as that containing the hybrid tRNA/pre-microRNA scaffolds (e.g., containing an inserted RNA) or may be provided in a container separate from that containing the hybrid tRNA/pre-microRNA scaffolds (e.g., containing an inserted RNA).

In some embodiments, a subject kit includes a quantity of any of the polynucleotides, expression cassettes, liposomes or nanoparticles, or compositions described herein, and any combinations thereof, present in unit dosages, e.g., ampoules, or a multi-dosage format. As such, in certain embodiments, the kits may include one or more (e.g., two or more) unit dosages (e.g., ampoules) of the polynucleotide, expression cassette, liposome or nanoparticle, composition, or any combination thereof.

The term "unit dosage", as used herein, refers to physically discrete units suitable as unitary dosages for human and animal subjects, each unit containing a predetermined quantity calculated in an amount sufficient to produce the desired effect. The amount of the unit dosage depends on various factors, such as the particular bifunctional molecule employed, the effect to be achieved, and the pharmacodynamics associated with the bifunctional molecule, in the subject. In yet other embodiments, the kits may include a single multi dosage amount of the bifunctional molecule or pharmaceutical composition.

The kits of the present disclosure may include instructions, e.g., for using the polynucleotide, expression cassette, liposome or nanoparticle, composition, or any combination thereof. For example, in some embodiments, a kit includes instructions for administering the polynucleotide, expression cassette, liposome or nanoparticle, composition, or any combination thereof, to a subject in need thereof. In some embodiments, the subject in need thereof has hepatocellular carcinoma (HCC).

The instructions included in the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

```
NUCLEOTIDE SEQUENCES
(underlined, tRNA sequence; italic, pre-miRNA sequence; bold
underlined, mature miRNA; italic underlined, passenger sequence)
nCAR^Met/miR-34a-5p(180 nt)
                                                        SEQ ID NO: 1
5'-GGCUACGUAGCUCAGUUGGUUAGAGCAGCGGCCGGGCCAGCUGUGAGUGUU

UCUUUGGCAGUGUCUUAGCUGGUUGUUGUGAGCAAUAGUAAGGAAGCAAUCAGCAAGUAUACUG

CCCUAGAAGUGCUGCACGUUGUUGGCCCCCGCGGGUCACAGGUUCGAAUCCCGUCGUAGCCACC

A-3' hCAR^Leu/miR-34a-5p(192 nt)
                                                        SEQ ID NO: 2
5'- ACCAGGAUGGCCGAGUGGUUAAGGCGUUGGACUGGCCAGCUGUGAGUGUUU

CUUUGGCAGUGUCUUAGCUGGUUGUUGUGAGCAAUAGUAAGGAAGCAAUCAGCAAGUAUACUGC

CCUAGAAGUGCUGCACGUUGUUGGCCCGAUCCAAUGGACAUAUGUCCGCGUGGGUUCGAACCCC

ACUCCUGGUACCA-3' hCAR^Ser/miR-34a-5p(191 nt)
                                                        SEQ ID NO: 3
5'- GCAGCGAUGGCCGAGUGGUUAAGGCGUUGGACUGGCCAGCUGUGAGUGUU

UCUUUGGCAGUGUCUUAGCUGGUUGUUGUGAGCAAUAGUAAGGAAGCAAUCAGCAAGUAUACUG

CCCUAGAAGUGCUGCACGUUGUUGGCCCAAUCCAAUGGGGUCUCCCCGCGCAGGUUCGAACCCU

GCUCGCUGCGCCA-3' hCAR^Lys/miR-34a-5p(182 nt)
                                                        SEQ ID NO: 4
5'- GCCUGGAUAGCUCAGUUGGUAGAGCAUCAGACUGGCCAGCUGUGAGUGUUU

CUUUGGCAGUGUCUUAGCUGGUUGUUGUGAGCAAUAGUAAGGAAGCAAUCAGCAAGUAUACUGC

CCUAGAAGUGCUGCACGUUGUUGGCCCAAUCUGAGGGUCCAGGGUUCAAGUCCCUGUUCAGGCG

CCA-3' hCAR^Gln/miR-34a-5p (181 nt)
                                                        SEQ ID NO: 5
5'- GGUCCCAUGGUGUAAUGGUUAGCACUCUGGACUGGCCAGCUGUGAGUGUUU
CUUUGGCAGUGUCUUAGCUGGUUGUUGUGAGCAAUAGUAAGGAAGCAAUCAGCAAGUAUACUGC

CCUAGAAGUGCUGCACGUUGUUGGCCCAAUCCAGCGAUCCGAGUUCAAAUCUCGGUGGGACCUC

CA-3'
```

-continued hCAR$^{Cys}$/miR-34a-5p (181 nt)

SEQ ID NO: 6

5'- GGGGGCAUAGCUCAGUGGUAGAGCAUUUGACU*GGCCAGCUGUGAGUGUUUC*

*UU*UGGCAGUGUCUUAGCUGGUUGU*UGUGAGCAAUAGUAAGGAAG*CAAUCAGCAAGUAUACUGCC

*CU*AGAAGUGCUGCACGUUGUUGGCCC*GAUCAAGAGGUCCCUGGUUCAAAUCCAGGUGCCCCCUC*

*CA*-3' htRNA$^{Leu}$/miR-124-3p (167 nt)

SEQ ID NO: 7

5'- ACCAGGAUGGCCGAGUGGUUAAGGCGUUGGAC*AGGCCUCUCUCUC*CGUGU

UCACAGCGGACCUUGAU*UUAAAUGUCCAUACAAU*UAAGGCACGCGGUGAAUGCC*AAGAAUGGGG*

*CUGGAUCCAAUGGACAUAUGUCCGCGUGGGUUCGAACCCCACUCCUGGUACCA*-3' htRNA$^{Ser}$/miR-124-3p (167 nt)

SEQ ID NO: 8

5'- GCAGCGAUGGCCGAGUGGUUAAGGCGUUGGACU*AGGCCUCUCUCUC*CGUGU

UCACAGCGGACCUUGAU*UUAAAUGUCCAUACAAU*UAAGGCACGCGGUGAAUGCC*AAGAAUGGGG*

*CUGAAUCCAAUGGGGUCUCCCCGCGCAGGUUCGAACCCUGCUCGCUGCGCCA*-3' htRNA$^{Lys}$/miR-124-3p (158 nt)

SEQ ID NO: 9

5'- GCCUGGAUAGCUCAGUUGGUAGAGCAUCAGACU*AGGCCUCUCUCUC*CGUGU

UCACAGCGGACCUUGAU*UUAAAUGUCCAUACAAU*UAAGGCACGCGGUGAAUGCC*AAGAAUGGGG*

*CUGAAUCUGAGGGUCCAGGGUUCAAGUCCCUGUUCAGGCGCCA*-3' htRNA$^{Gln}$/miR-124-3p (157 nt)

SEQ ID NO: 10

5'- GGUCCCAUGGUGUAAUGGUUAGCACUCUGGACU*AGGCCUCUCUCUC*CGUGU

UCACAGCGGACCUUGAU*UUAAAUGUCCAUACAAU*UAAGGCACGCGGUGAAUGCC*AAGAAUGGGG*

*CUGAAUCCAGCGAUCCGAGUUCAAAUCUCGGUGGGACCUCCA*-3' htRNA$^{Cys}$/miR-124-3p (157 nt)

SEQ ID NO: 11

5'- GGGGGCAUAGCUCAGUGGUAGAGCAUUUGACU*AGGCCUCUCUCUC*CGUGU

UCACAGCGGACCUUGAU*UUAAAUGUCCAUACAAU*UAAGGCACGCGGUGAAUGCC*AAGAAUGGGG*

*CUGGAUCAAGAGGUCCCUGGUUCAAAUCCAGGUGCCCCCUCCA*-3' nCAR$^{Met}$/let-7c-5p (181 nt)

SEQ ID NO: 12

5'- GGCUACGUAGCUCAGUUGGUUAGAGCAG*CGGCCGGGCCAGCUGUGAGUGUU*

*UCUU*UGAGGUAGUAGGUUGUAUGGUU*UGUGAGCAAUAGUAAGGAAG*AACUGUACACCUUACUAC*

*CUUUC*AGAAGUGCUGCACGUUGUUGGCCCCC*GCGGGUCACAGGUUCGAAUCCCGUCGUAGCCAC*

*CA*-3' hCAR$^{Leu}$/let-7c-5p (193 nt)

SEQ ID NO: 13

5'- ACCAGGAUGGCCGAGUGGUUAAGGCGUUGGACU*GGCCAGCUGUGAGUGUUU*

*CUU*UGAGGUAGUAGGUUGUAUGGUU*UGUGAGCAAUAGUAAGGAAG*AACUGUACACCUUACUACC*

*UUUC*AGAAGUGCUGCACGUUGUUGGCCC*GAUCCAAUGGACAUAUGUCCGCGUGGGUUCGAACCC*

*CACUCCUGGUACCA*-3' hCAR$^{Ser}$/let-7c-5p (192 nt)

SEQ ID NO: 14

5'- GCAGCGAUGGCCGAGUGGUUAAGGCGUUGGACU*GGCCAGCUGUGAGUGUUU*

*CUU*UGAGGUAGUAGGUUGUAUGGUU*UGUGAGCAAUAGUAAGGAAG*AACUGUACACCUUACUACC*

*UUUC*AGAAGUGCUGCACGUUGUUGGCCC*AAUCCAAUGGGGUCUCCCCGCGCAGGUUCGAACCCU*

*GCUCGCUGCGCCA*-3' hCAR<sup>Lys</sup>/let-7c-5p(183 nt)

SEQ ID NO: 15

5'- GCCUGGAUAGCUCAGUUGGUAGAGCAUCAGACUGGCCAGCUGUGAGUGUUU

CUUUGAGGUAGUAGGUUGUAUGGUUUGUGAGCAAUAGUAAGGAAGAACUGUACACCUUACUACC

UUUCAGAAGUGCUGCACGUUGUUGGCCCAAUCUGAGGGUCCAGGGUUCAAGUCCCUGUUCAGGC

GCCA-3' hCAR<sup>Gln</sup>/let-7c-5p(182 nt)

SEQ ID NO: 16

5'- GGUCCCAUGGUGUAAUGGUUAGCACUCUGGACUGGCCAGCUGUGAGUGUUU

CUUUGAGGUAGUAGGUUGUAUGGUUUGUGAGCAAUAGUAAGGAAGAACUGUACACCUUACUACC

UUUCAGAAGUGCUGCACGUUGUUGGCCCAAUCCAGCGAUCCGAGUUCAAAUCUCGGUGGGACCU

CCA-3' hCAR<sup>Cys</sup>/let-7c-5p(182 nt)

SEQ ID NO: 17

5'- GGGGGCAUAGCUCAGUGGUAGAGCAUUUGACUGGCCAGCUGUGAGUGUUUC

UUUGAGGUAGUAGGUUGUAUGGUUUGUGAGCAAUAGUAAGGAAGAACUGUACACCUUACUACCU

UUCAGAAGUGCUGCACGUUGUUGGCCCGAUCAAGAGGUCCCUGGUUCAAAUCCAGGUGCCCCCU

CCA-3' htRNA<sup>Ser</sup>/pre-let-7c-5p(166 nt)

SEQ ID NO: 18

5'- GCAGCGAUGGCCGAGUGGUUAAGGCGUUGGACUGCAUCCGGGUUGAGGUA

GUAGGUUGUAUGGUUUAGAGUUACACCCUGGGAGUUAACUGUACAACCUUCUAGCUUUCCUUGG

AGCAAUCCAAUGGGGUCUCCCCGCGCAGGUUCGAACCCUGCUCGCUGCGCCA-3' htRNA<sup>Leu</sup>/pre-let-7c-5p(168 nt)

SEQ ID NO: 19

5'- ACCAGGAUGGCCGAGUGGUUAAGGCGUUGGACUGCAUCCGGGUUGAGGUA

GUAGGUUGUAUGGUUUAGAGUUACACCCUGGGAGUUAACUGUACAACCUUCUAGCUUUCCUUGG

AGCAGAUCCAAUGGACAUAUGUCCGCGUGGGUUCGAACCCCACUCCUGGUACCA-3' htRNA<sup>Lys</sup>/pre-let-7c-5p(152 nt)

SEQ ID NO: 20

5'- GCCUGGAUAGCUCAGUUGGUAGAGCAUGCAUCCGGGUUGAGGUA

GUAGGUUGUAUGGUUUAGAGUUACACCCUGGGAGUUAACUGUACAACCUUCUAGCUUUCCUUGG

AGCAAAUCUGAGGGUCCAGGGUUCAAGUCCCUGUUCAGGCGCCA-3' htRNA<sup>Cys</sup>/pre-let-7c-5p(157 nt)

SEQ ID NO: 21

5'- GGGGGCAUAGCUCAGUGGUAGAGCAUUUGACUGCAUCCGGGUUGAGGUA

GUAGGUUGUAUGGUUUAGAGUUACACCCUGGGAGUUAACUGUACAACCUUCUAGCUUUCCUUGG

AGCAGAUCAAGAGGUCCCUGGUUCAAAUCCAGGUGCCCCUCCA-3' htRNA<sup>Gln</sup>/pre-let-7c-5p(157 nt)

SEQ ID NO: 22

5'- GGUCCCAUGGUGUAAUGGUUAGCACUCUGGACUGCAUCCGGGUUGAGGUA

GUAGGUUGUAUGGUUUAGAGUUACACCCUGGGAGUUAACUGUACAACCUUCUAGCUUUCCUUGG

AGCAAAUCCAGCGAUCCGAGUUCAAAUCUCGGUGGGACCUCCA-3' nCAR<sup>Met</sup>/miR-328-3p(180 nt)

SEQ ID NO: 23

5'- GGCUACGUAGCUCAGUUGGUUAGAGCAGCGGCCGGGCCAGCUGUGAGUGUU

UCUUCUGGCCCUCUCUGCCCUUCCGUUGUGAGCAAUAGUAAGGAAGCGGGGGGGAGAUGGGGGC

CAUUAGAAGUGCUGCACGUUGUUGGCCCCGCGGGUCACAGGUUCGAAUCCCGUCGUAGCCACC

A-3'

-continued hCAR<sup>Leu</sup>/miR-328-3p(192 nt)
SEQ ID NO: 24
5'- ACCAGGAUGGCCGAGUGGUUAAGGCGUUGGACUGGCCAGCUGUGAGUGUUU
CUUCUGGCCCUCUCUGCCCUUCCGUUGUGAGCAAUAGUAAGGAAGCGGGGGGGAGAUGGGGCC
AUUAGAAGUGCUGCACGUUGUUGGCCCGAUCCAAUGGACAUAUGUCCGCGUGGGUUCGAACCCC
ACUCCUGGUACCA-3' hCAR<sup>Ser</sup>/miR-328-3p(191 nt)
SEQ ID NO: 25
5'- GCAGCGAUGGCCGAGUGGUUAAGGCGUUGGACUGGCCAGCUGUGAGUGUUU
CUUCUGGCCCUCUCUGCCCUUCCGUUGUGAGCAAUAGUAAGGAAGCGGGGGGGAGAUGGGGCC
AUUAGAAGUGCUGCACGUUGUUGGCCCAAUCCAAUGGGGUCUCCCCGCGCAGGUUCGAACCCUG
CUCGCUGCGCCA-3' hCAR<sup>Lys</sup>/miR-328-3p(182 nt)
SEQ ID NO: 26
5'- GCCUGGAUAGCUCAGUUGGUAGAGCAUCAGACUGGCCAGCUGUGAGUGUUU
CUUCUGGCCCUCUCUGCCCUUCCGUUGUGAGCAAUAGUAAGGAAGCGGGGGGGAGAUGGGGCC
AUUAGAAGUGCUGCACGUUGUUGGCCCAAUCUGAGGGUCCAGGGUUCAAGUCCCUGUUCAGGCG
CCA-3' hCAR<sup>Gln</sup>/miR-328-3p(181 nt)
SEQ ID NO: 27
5'- GGUCCCAUGGUGUAAUGGUUAGCACUCUGGACUGGCCAGCUGUGAGUGUUU
CUUCUGGCCCUCUCUGCCCUUCCGUUGUGAGCAAUAGUAAGGAAGCGGGGGGGAGAUGGGGCC
AUUAGAAGUGCUGCACGUUGUUGGCCCAAUCCAGCGAUCCGAGUUCAAAUCUCGGUGGGACCUC
CA-3' hCAR<sup>Cys</sup>/miR-328-3p(181 nt)
SEQ ID NO: 28
5'- GGGGGCAUAGCUCAGUGGUAGAGCAUUUGACUGGCCAGCUGUGAGUGUUUC
UUCUGGCCCUCUCUGCCCUUCCGUUGUGAGCAAUAGUAAGGAAGCGGGGGGGAGAUGGGGCCA
UUAGAAGUGCUGCACGUUGUUGGCCCGAUCAAGAGGUCCCUGGUUCAAAUCCAGGUGCCCCCUC
CA-3' nCAR<sup>Met</sup>/miR-124-3p(180 nt)
SEQ ID NO: 29
5'- GGCUACGUAGCUCAGUUGGUUAGAGCAGCGGCCGGGCCAGCUGUGAGUGUU
UCUUUAAGGCACGCGGUGAAUGCCGUUGUGAGCAAUAGUAAGGAAGCGGUGUUCCCGUCGUGCC
UUCUAGAAGUGCUGCACGUUGUUGGCCCCCGCGGGUCACAGGUUCGAAUCCCGUCGUAGCCACC
A-3' hCAR<sup>Leu</sup>/miR-124-3p(192 nt)
SEQ ID NO: 30
5'- ACCAGGAUGGCCGAGUGGUUAAGGCGUUGGACUGGCCAGCUGUGAGUGUUU
CUUUAAGGCACGCGGUGAAUGCCGUUGUGAGCAAUAGUAAGGAAGCGGUGUUCCCGUCGUGCCU
UCUAGAAGUGCUGCACGUUGUUGGCCCGAUCCAAUGGACAUAUGUCCGCGUGGGUUCGAACCCC
ACUCCUGGUACCA-3' hCAR<sup>Ser</sup>/miR-124-3p(191 nt)
SEQ ID NO: 31
5'- GCAGCGAUGGCCGAGUGGUUAAGGCGUUGGACUGGCCAGCUGUGAGUGUUU
CUUUAAGGCACGCGGUGAAUGCCGUUGUGAGCAAUAGUAAGGAAGCGGUGUUCCCGUCGUGCCU
UCUAGAAGUGCUGCACGUUGUUGGCCCAAUCCAAUGGGGUCUCCCCGCGCAGGUUCGAACCCUG
CUCGCUGCGCCA-3'

-continued hCAR<sup>Lys</sup>/miR-124-3p(182 nt)
SEQ ID NO: 32
5'- GCCUGGAUAGCUCAGUUGGUAGAGCAUCAGACUGGCCAGCUGUGAGUGUUU

CUUUAAGGCACGCGGUGAAUGCCGUUGUGAGCAAUAGUAAGGAAGCGGUGUUCCCGUCGUGCCU

UCUAGAAGUGCUGCACGUUGUUGGCCCAAUCUGAGGGUCCAGGGUUCAAGUCCCUGUUCAGGCG

CCA-3' hCARsin/miR-124-3p(181 nt)
SEQ ID NO: 33
5'- GGUCCCAUGGUGUAAUGGUUAGCACUCUGGACUGGCCAGCUGUGAGUGUUU

CUUUAAGGCACGCGGUGAAUGCCGUUGUGAGCAAUAGUAAGGAAGCGGUGUUCCCGUCGUGCCU

UCUAGAAGUGCUGCACGUUGUUGGCCCAAUCCAGCGAUCCGAGUUCAAAUCUCGGUGGGACCUC

CA-3' hCAR<sup>Cys</sup>/miR-124-3p(181 nt)
SEQ ID NO: 34
5'- GGGGGCAUAGCUCAGUGGUAGAGCAUUUGACUGGCCAGCUGUGAGUGUUUC

UUUAAGGCACGCGGUGAAUGCCGUUGUGAGCAAUAGUAAGGAAGCGGUGUUCCCGUCGUGCCUU

CUAGAAGUGCUGCACGUUGUUGGCCCGAUCAAGAGGUCCCUGGUUCAAAUCCAGGUGCCCCCUC

CA-3' nCAR<sup>Met</sup>/miR-126-3p(180 nt)
SEQ ID NO: 35
5'- GGCUACGUAGCUCAGUUGGUUAGAGCAGCGGCCGGGCCAGCUGUGAGUGUUU

UCUUUCGUACCGUGAGUAAUAAUGCGUGUGAGCAAUAGUAAGGAAGUGCAUUAUUCUCUAUGGU

ACGCAGAAGUGCUGCACGUUGUUGGCCCCGCGGGUCACAGGUUCGAAUCCCGUCGUAGCCACC

A-3' hCAR<sup>Leu</sup>/miR-126-3p(192 nt)
SEQ ID NO: 36
5'- ACCAGGAUGGCCGAGUGGUUAAGGCGUUGGACUGGCCAGCUGUGAGUGUUU

CUUUCGUACCGUGAGUAAUAAUGCGUGUGAGCAAUAGUAAGGAAGGUGCAUUAUUCUCUAUGGU

ACGAGAAGUGCUGCACGUUGUUGGCCCGAUCCAAUGGACAUAUGUCCGCGUGGGUUCGAACCCC

ACUCCUGGUACCA-3' hCAR<sup>Ser</sup>/miR-126-3p(191 nt)
SEQ ID NO: 37
5'- GCAGCGAUGGCCGAGUGGUUAAGGCGUUGGACUGGCCAGCUGUGAGUGUUU

CUUUCGUACCGUGAGUAAUAAUGCGUGUGAGCAAUAGUAAGGAAGGUGCAUUAUUCUCUAUGGU

ACGAGAAGUGCUGCACGUUGUUGGCCCAAUCCAAUGGGGUCUCCCCGCGCAGGUUCGAACCCUG

CUCGCUGCGCCA-3' hCAR<sup>Lys</sup>/miR-126-3p(182 nt)
SEQ ID NO: 38
5'- GCCUGGAUAGCUCAGUUGGUAGAGCAUCAGACUGGCCAGCUGUGAGUGUUU

CUUUCGUACCGUGAGUAAUAAUGCGUGUGAGCAAUAGUAAGGAAGGUGCAUUAUUCUCUAUGGU

ACGAGAAGUGCUGCACGUUGUUGGCCCAAUCUGAGGGUCCAGGGUUCAAGUCCCUGUUCAGGCG

CCA-3'.

hCAR<sup>Gln</sup>/miR-126-3p(181 nt)
SEQ ID NO: 39
5'- GGUCCCAUGGUGUAAUGGUUAGCACUCUGGACUGGCCAGCUGUGAGUGUUU

CUUUCGUACCGUGAGUAAUAAUGCGUGUGAGCAAUAGUAAGGAAGGUGCAUUAUUCUCUAUGGU

ACGAGAAGUGCUGCACGUUGUUGGCCCAAUCCAGCGAUCCGAGUUCAAAUCUCGGUGGGACCUC

CA-3' hCAR$^{Cys}$/miR-126-3p(181 nt)

SEQ ID NO: 40

5'- GGGGGCAUAGCUCAGUGGUAGAGCAUUUGACUGGCCAGCUGUGAGUGUUUC

UUUCGUACCGUGAGUAAUAAUGCGUGUGAGCAAUAGUAAGGAAGGUGCAUUAUUCUCUAUGGUA

CGAGAAGUGCUGCACGUUGUUGGCCCGAUCAAGAGGUCCCUGGUUCAAAUCCAGGUGCCCCCUC

CA-3' nCAR$^{Met}$/miR-298-5p(180 nt)

SEQ ID NO: 41

5'- GGCUACGUAGCUCAGUUGGUUAGAGCAGCGGCCGGGCCAGCUGUGAGUGUU

UCUUAGCAGAAGCAGGGAGGUUCUCCCAUGAGCAAUAGUAAGGAGGGGAGAACCCCCAUGCUUU

UGACAGAAGUGCUGCACGUUGUUGGCCCCCGCGGGUCACAGGUUCGAAUCCCGUCGUAGCCACC

A-3' hCAR$^{Leu}$/miR-298-5p(194 nt)

SEQ ID NO: 42

5'- ACCAGGAUGGCCGAGUGGUUAAGGCGUUGGACUGGCCAGCUGUGAGUGUUU

CUUAGCAGAAGCAGGGAGGUUCUCCCAUGUGAGCAAUAGUAAGGAAGGGAGAACCCCCAUGCUU

UUGACAGAAGUGCUGCACGUUGUUGGCCCGAUCCAAUGGACAUAUGUCCGCGUGGGUUCGAACC

CCACUCCUGGUACCA-3' hCAR$^{Ser}$/miR-298-5p(193 nt)

SEQ ID NO: 43

5'- GCAGCGAUGGCCGAGUGGUUAAGGCGUUGGACUGGCCAGCUGUGAGUGUUU

CUUAGCAGAAGCAGGGAGGUUCUCCCAUGUGAGCAAUAGUAAGGAAGGGAGAACCCCCAUGCUU

UUGACAGAAGUGCUGCACGUUGUUGGCCCAAUCCAAUGGGGUCUCCCCGCGCAGGUUCGAACCC

UGCUCGCUGCGCCA-3' hCAR$^{Lys}$/miR-298-5p(184 nt)

SEQ ID NO: 44

5'- GCCUGGAUAGCUCAGUUGGUAGAGCAUCAGACUGGCCAGCUGUGAGUGUUU

CUUAGCAGAAGCAGGGAGGUUCUCCCAUGUGAGCAAUAGUAAGGAAGGGAGAACCCCCAUGCUU

UUGACAGAAGUGCUGCACGUUGUUGGCCCAAUCUGAGGGUCCAGGGUUCAAGUCCCUGUUCAGG

CGCCA-3' hCAR$^{Gln}$/miR-298-5p(183 nt)

SEQ ID NO: 45

5'- GGUCCCAUGGUGUAAUGGUUAGCACUCUGGACUGGCCAGCUGUGAGUGUUU

CUUAGCAGAAGCAGGGAGGUUCUCCCAUGUGAGCAAUAGUAAGGAAGGGAGAACCCCCAUGCUU

UUGACAGAAGUGCUGCACGUUGUUGGCCCAAUCCAGCGAUCCGAGUUCAAAUCUCGGUGGGACC

UCCA-3' hCAR$^{Cys}$/miR-298-5p(183 nt)

SEQ ID NO: 46

5'- GGGGGCAUAGCUCAGUGGUAGAGCAUUUGACUGGCCAGCUGUGAGUGUUUC

UUAGCAGAAGCAGGGAGGUUCUCCCAUGUGAGCAAUAGUAAGGAAGGGAGAACCCCCAUGCUUU

UGACAGAAGUGCUGCACGUUGUUGGCCCGAUCAAGAGGUCCCUGGUUCAAAUCCAGGUGCCCCC

UCCA-3' htRNA$^{Leu}$-seph(aptamer is not underlined )

SEQ ID NO: 47

ACCAGGAUGGCCGAGUGGUUAAGGCGUUGGACUAGUAAUUUACGUCGACGGUGACGUCGAUGGU

UGCGGGAUCCAAUGGACAUAUGUCCGCGUGGGUUCGAACCCCACUCCUGGUACCA htRNA$^{Ser}$-seph(aptamer is not underlined )

SEQ ID NO: 48

GCAGCGAUGGCCGAGUGGUUAAGGCGUUGGACUAGUAAUUUACGUCGACGGUGACGUCGAUGGU

UGCGGAAUCCAAUGGGGUCUCCCCGCGCAGGUUCGAACCCUGCUCGCUGCGCCA

-continued htRNA<sup>Lys</sup>-seph(aptamer is not underlined)
SEQ ID NO: 49
GCCUGGAUAGCUCAGUUGGUAGAGCAUCAGACUAGUAAUUUACGUCGACGGUGACGUCGAUGGU

UGCGGAAUCUGAGGGUCCAGGGUUCAAGUCCCUGUUCAGGCACCA htRNA<sup>Gln</sup>-seph(aptamer is not underlined)
SEQ ID NO: 50
GGUCCCAUGGUGUAAUGGUUAGCACUCUGGACUAGUAAUUUACGUCGACGGUGACGUCGAUGGU

UGCGGAAUCCAGCGAUCCGAGUUCAAAUCUCGGUGGGACCUCCA htRNA<sup>Cys</sup>-seph(aptamer is not underlined)
SEQ ID NO: 51
GGGGGCAUAGCUCAGUGGUAGAGCAUUUGACUAGUAAUUUACGUCGACGGUGACGUCGAUGGUU

GCGGGAAUCAAGAGGUCCCUGGUUCAAAUCCAGGUGCCCCCUCCA htRNA<sup>Met</sup>-seph(aptamer is not underlined)
SEQ ID NO: 52
GCCUCGUUAGCGCAGUAGGUAGCGCGUCAGUCUAGUAAUUUACGUCGACGGUGACGUCGAUGGU

UGCGGAAUCUGAAGGUCGUGAGUUCGAUCCUCACACGGGGCACCA htRNA<sup>Leu</sup>-EpCA(aptamer is not underlined)
SEQ ID NO: 53
ACCAGGAUGGCCGAGUGGUUAAGGCGUUGGACUGCGACUGGUUACCCGGUCGGAUCCAAUGGAC

AUAUGUCCGCGUGGGUUCGAACCCCACUCCUGGUACCA htRNA<sup>Ser</sup>-EpCA(aptamer is not underlined)
SEQ ID NO: 54
GCAGCGAUGGCCGAGUGGUUAAGGCGUUGGACUGCGACUGGUUACCCGGUCGAAUCCAAUGGGG

UCUCCCCGCGCAGGUUCGAACCCUGCUCGCUGCGCCA htRNA<sup>Lys</sup>-EpCA(aptamer is not underlined)
SEQ ID NO: 55
GCCUGGAUAGCUCAGUUGGUAGAGCAUCAGACUGCGACUGGUUACCCGGUCGAAUCUGAGGGUC

CAGGGUUCAAGUCCCUGUUCAGGCACCA htRNA<sup>Gln</sup>-EpCA(aptamer is not underlined)
SEQ ID NO: 56
GGUCCCAUGGUGUAAUGGUUAGCACUCUGGACUGCGACUGGUUACCCGGUCGAAUCCAGCGAUC

CGAGUUCAAAUCUCGGUGGGACCUCCA htRNA<sup>Cys</sup>-EpCA(aptamer is not underlined)
SEQ ID NO: 57
GGGGGCAUAGCUCAGUGGUAGAGCAUUUGACUGCGACUGGUUACCCGGUCGGAUCAAGAGGUCC

CUGGUUCAAAUCCAGGUGCCCCCUCCA htRNA<sup>Met</sup>-EpCA(aptamer is not underlined)
SEQ ID NO: 58
GCCUCGUUAGCGCAGUAGGUAGCGCGUCAGUCUGCGACUGGUUACCCGGUCGAAUCUGAAGGUC

GUGAGUUCGAUCCUCACACGGGGCACCA htRNA<sup>Leu</sup>-Theo(aptamer is not underlined)
SEQ ID NO: 59
ACCAGGAUGGCCGAGUGGUUAAGGCGUUGGACUGGCGAUACCAGCCGAAAGGCCCUUGGCAGCG

UCGAUCCAAUGGACAUAUGUCCGCGUGGGUUCGAACCCCACUCCUGGUACCA htRNA<sup>Ser</sup>-Theo(aptamer is not underlined)
SEQ ID NO: 60
GCAGCGAUGGCCGAGUGGUUAAGGCGUUGGACUGGCGAUACCAGCCGAAAGGCCCUUGGCAGCG

UCAAUCCAAUGGGGUCUCCCCGCGCAGGUUCGAACCCUGCUCGCUGCGCCA htRNA<sup>Lys</sup>-Theo(aptamer is not underlined)
SEQ ID NO: 61
GCCUGGAUAGCUCAGUUGGUAGAGCAUCAGACUGGCGAUACCAGCCGAAAGGCCCUUGGCAGCG

UCAAUCUGAGGGUCCAGGGUUCAAGUCCCUGUUCAGGCACCA

-continued htRNA$^{Gln}$-Theo(aptamer is not underlined)
SEQ ID NO: 62
GGUCCCAUGGUGUAAUGGUUAGCACUCUGGACUGGCGAUACCAGCCGAAAGGCCCUUGGCAGCG

UCAAUCCAGCGAUCCGAGUUCAAAUCUCGGUGGGACCUCCA htRNA$^{Cys}$-Theo(aptamer is not underlined)
SEQ ID NO: 63
GGGGGCAUAGCUCAGUGGUAGAGCAUUUGACUGGCGAUACCAGCCGAAAGGCCCUUGGCAGCGU

CGAUCAAGAGGUCCCUGGUUCAAAUCCAGGUGCCCCUCCA htRNA$^{Met}$-Theo(aptamer is not underlined)
SEQ ID NO: 64
GCCUCGUUAGCGCAGUAGGUAGCGCGUCAGUCUGGCGAUACCAGCCGAAAGGCCCUUGGCAGCG

UCAAUCUGAAGGUCGUGAGUUCGAUCCUCACACGGGGCACCA

EXAMPLES

The following examples are offered to illustrate, but not to limit the claimed invention.

Bioengineered Let-7c Loaded Lipopolyplex Inhibits Hepatocellular Carcinoma (HCC) and Improves Overall Survival with Minimal Immunogenicity Materials and Methods Materials.

In vivo-jetPEI (linear 22 kDa PEI; 1PEI) was purchased from Polyplus Transfection (Illkirch, France). Branched polyethylenimine with molecular weight 10,000 Da (bPEI10k) was bought from Alfa Aesar (Wardhill, Mass.). 1,2-di-O-octadecenyl-3-trimethylammonium propane (DOTMA) and cholesterol were purchased from Avanti Polar Lipids (Alabaster, Ala.). 1,2-Dimyristoyl-sn-glycerol, methoxypolyethylene glycol (DMG-PEG2000) was purchased from NOF America Corporation (White Plains, N.Y.). Lipofectamine 3000 (LF3000), TRIzol RNA isolation reagent, and BCA protein assay kit were purchased from Thermo Fisher Scientific (Waltham, Mass.). Direct-zol RNA MiniPrep Kit was from Zymo Research (Irvine, Calif.). Celltiter-Glo assay was purchased from Promega (Madison, Wis.). Matrigel was purchased from Corning (Corning, N.Y.). Human α-fetoprotein ELISA kit was purchased from R&D Systems (San Diego, Calif.). All other chemicals and organic solvents of analytical grade were purchased from Sigma Aldrich or Thermo Fisher Scientific.

Cell Culture.

Sk-Hep-1 cells were obtained from American Type Culture Collection and grown in Eagle's minimal essential medium (Cellgro, Manassas, Va.), and Huh7 cells were bought from Japanese Collection of Research Bioresources and grown in Dulbecco's modified Eagle medium (Gibco, Grand Island, N.Y.). Both cell lines were supplemented with 10% fetal bovine serum (Gibco, Grand Island, N.Y.) and 1% antibiotic/antimycotic (Cellgro, Manassas, Va.). GFP/luciferase-expressing cell lines were established after transduction of parental cells with pCCLc-Luc-EGFP lentiviral constructs (Vector Core, UC Davis Medical Center, Sacramento, Calif.). All cells were transfected with Lipofectamine 3000 (Invitrogen, Carlsbad, Calif.) per the manufacturer's instructions for in vitro RNA delivery, unless otherwise indicated.

Production of Recombinant miRNA Agents.

Bioengineering of miRNA molecules was conducted as described very recently (21). Briefly, inserts encoding target miRNA-containing ncRNAs were cloned into a pBSMrna vector using In-Fusion cloning technology and transformed into HST08 *Escherichia coli*. Recombinant ncRNAs were purified by anion exchange fast protein liquid chromatography (FPLC) to >96% purity that was determined by a high performance liquid chromatography (HPLC) assay (23). Bioengineered let-7c less than 95% pure was re-purified by the same FPLC method to reach >96% homogeneity. Endotoxin activity was examined with Pyrogent-5000 kinetic LAL assay (Lonza, Walkersville, Md.).

Cell Viability Assay.

GFP/luciferase-expressing Sk-Hep-1 and Huh7 cells (5,000 cells/well) were seeded in 96-well plates and grown overnight. let-7c or MSA was administered in triplicate with either Lipofectamine 3000 or LPP. Cell viability was measured using Cell Titer-Glo kit. Inhibition of cell viability was determined as relative to vehicle control (0% inhibition) and pharmacodynamics parameters were estimated by fitting the data to fitting the data to a normalized dose response equation with variable slope:

$$Y=100/(1+[10]\hat{}[EC]\_50-X)*\text{Hill Slope}))$$

Given low efficacy, MSA (Emax, Emin=100, 20.64%) and miR-144 (Emax, Emin=44.42, 17.27%) in Huh7 cells were best fit to the full dose response equation equation:

$$Y=E\_min+(E\_max-E\_min)/$$
$$(1+[10]\hat{}((Log[EC])\_50-X)*$$
$$\text{Hill Slope}))$$

Immunoblot and Immunofluorescence Analyses.

Huh7 and Sk-Hep-1 cells were seeded in 6-well plate at 300,000 cells/well and transfected with 15 nM RNA. After 72 h, cells were harvested and lysed in RIPA buffer with protease inhibitor (Pierce, Rockford, Ill.). Protein levels were determined by BCA assay (Pierce, Rockford, Ill.). After separated on a 12% SDS-PAGE gel (Bio-Rad, Hercules, Calif.), proteins were transferred onto a polyvinylidene difluoride membrane, and blocked in 5% milk/1% Tween-20 in tris-buffered saline. Total immobilized protein was imaged per the manufacturer's instructions. Membranes were incubated with primary antibodies (Bcl-xl rabbit mAb [CST 2764], c-Myc rabbit mAb [CST 13987], and LIN28B rabbit mAb [CST 11965] from Cell Signaling Inc.; ARID3B rabbit pAb [AB 92328] from Abcam) overnight at 4° C. at 1:1,000 dilution in 5% bovine serum albumin in TBS-T, followed by horseradish peroxidase-conjugated goat-anti-rabbit secondary antibody (1:10,000 dilution) for 2 h at room temperature prior to chemiluminescent imaging with Clarity ECL (Bio-Rad, Hercules, Calif.). Relative band intensity was normalized to total immobilized protein.

To assay HMGA2 expression, Huh7 and Sk-Hep-1 cells were grown on glass chamber slides and transfected with MSA or let-7c. After 72 h, cells were fixed with 10% formalin, permeabilized with 1% Triton X-100, and incubated with HMGA2 rabbit mAb [CST 8179] (1:400 dilution in 5% bovine serum albumin) overnight at 4° C. Antigen was detected with Alexa 488-conjugated anti-rabbit IgG Fab fragment [CST 4412] and nuclei were counterstained with DAPI [CST 4803].

Flow Cytometry.

Huh7 and Sk-Hep-1 cells were plated in 6-well plates at a density of 150,000 cells/well and transfected with 5 nM RNA. After 48 h, cells were stained with propidium iodide and Annexin V-FITC per manufacturer's instructions (Trevigen, Gaithersburg, Md.). Cell count and fluorophore intensity was measured using a BD Biosciences Fortessa 20 color cytometer. Total event count was gated at 10,000 events and quadrant gating was set relative to vehicle control.

Tumorsphere Assay.

Huh7 cells were seeded under adherent conditions at a density of 300,000 cells/well in 6-well plates and transfected with 15 nM RNA. After 48 hours, live cells were transferred to 24-well ultra-low attachment plates (Corning, Kennebunk, Me.) at a density of 2,500 cells/well and grown in DMEM/F12+B27 with penicillin/streptomycin, GlutaMax (Gibco, Grand Island, N.Y.), 20 ng/ml human epidermal growth factor, and 10 ng/ml human basic-fibroblast growth factor (Peprotech, Rocky Hill, N.J.). After 7 days, primary tumorspheres (>10 μm diameter) were counted, sphere diameter was measured in ImageJ, and dissociated with trypsin to single cell. After all cells were transferred to new wells in ultra-low attachment/serum free conditions, cells were transfected again with 15 nM RNA. After 7 days, secondary tumorspheres were again counted, diameter was measured, and dissociated to count individual cells. Sphere formation efficiency (%) was calculated relative to total single cells seeded from the previous generation.

Formulation and Characterization of LPP Nanocomplex.

5.07 mg DOTMA, 2.92 mg cholesterol and 0.38 mg DMG-PEG2000 (molar ratio=50:50:1) were dissolved in chloroform in a round-bottom flask. The organic solvent was removed by rotary evaporation, and the thin lipid film formed at the bottom of flasks was hydrated in 1 mL diethylpyrocarbonate-treated water using bath sonication, followed by further intermittent sonication by a Probe Sonicator (Thermo Fisher Scientific) for 100 s. The resultant liposomes were sterilized by passing through 0.22-μm sterile filter. Polyplex was formed by mixing 250 μL of purified RNA (1 mg/mL) and 250 μL bPEI10k (250 μg/mL) by pipetting, followed by incubation at room temperature for 5 min. LPP was produced by adding 500 μL freshly prepared polyplex into 500 μL liposomes through vigorous pipetting and incubating for 30 min Zeta potentials and particle sizes of RNA-loaded LPP were measured by dynamic light scattering (Malvern Zetasizer Nano ZS90 instrument, Malvern instruments Ltd. U. K.). The morphology of LPP/let-7c was observed on a Philips CM-120 transmission electron microscope (TEM) after staining with phosphotungstic acid on copper grid.

Serum stability. To determine stability in serum, 500 μL RNA-loaded formulations were mixed with 500 μL FBS or human serum and incubated at 37° C. At different time points, 100 μL of samples were subjected to total RNA isolation using TRIzol and analyzed by denaturing urea polyacrylamide (8%) gel electrophoresis (PAGE) to assess RNA integrity.

In Vitro Knockdown of GFP-mRNA by GFP-siRNA in SK-Hep-Luc-GFP Cells.

SK-Hep1-Luc-GFP was seeded in 12-well plate and grown overnight at the density of 5×10⁴ cells/well. BERA/GFP-siRNA-loaded LPP nanocomplex was added into each well to a final concentration of 5 nM. LP3000 and IVJ-PEI formulations were included for comparison. After 72 h of treatment, cells were collected and total RNA was extracted with Trizol and Direct-zol RNA MiniPrep Kit (Zymo Research). cDNA was synthesized from 500 ng total RNA using NxGen M-MuLV reverse transcriptase (Lucigen, Middleton, Wis., USA), with random hexamers. Levels of GFP-mRNA were determined by using 18S as the internal standard. Primers used in this study are listed in Table 1. All real-time qPCR experiments were performed using iTaq Universal SYBR Green Supermix on a CFX96 Touch real-time PCR system (Bio-Rad, Hercules, Calif., USA). Cells were treated in triplicate and assayed separately. The comparative threshold cycle (Ct) approach with the formula $2^{-\Delta\Delta ct}$ was utilized to calculate the relative gene expression.

TABLE 1

| List of Primers | |
| --- | --- |
| Let-7c (RT) | 5'-GTCGTATCCAGTGCAGGGTCCCAGGTA TTCGCACTGGATACGACAACCAT-3' (SEQ ID NO: 65) |
| Let-7c (PCR) | Reverse: 5'-GCGCTAAGGCACGCGGTG-3' (SEQ ID NO: 66) Forward 5'-CGCGCTGAGGTAGTAGGTTGT-3' (SEQ ID NO: 67) |
| GFP | Forward 5'-ACGTAAACGGCCACAAGTTC-3' (SEQ ID NO: 68) Reverse 5'-AAGTCGTGCTGCTTCATGTG-3' (SEQ ID NO: 69) |
| 18S | Forward 5'-GTAACCCGTTGAACCCCATT-3' (SEQ ID NO: 70) Reverse 5'-CCATCCAATCGGTAGTAGCG-3' (SEQ ID NO: 71) |
| U6 | Forward 5'-CTCGCTTCGGCAGCACA-3' (SEQ ID NO: 72) Reverse 5'-AACGCTTCACGAATTTGCGT-3' (SEQ ID NO: 73) |

In Vitro Delivery of let-7c and Inhibition of Cell Growth.

To assess in vitro let-7c delivery, GFP/luciferase-transduced Sk-Hep-1 or Huh7 cells (50,000 cells/well) were seeded in 12-well plate and grown overnight. LPP nanocomplex or LF3000-formulated let-7c was added into each well to a final concentration of 15 nM RNA. After 72 h, cells were lysed with Trizol, RNA was collected with Direct-zol RNA MiniPrep Kit (Zymo Research, Irvine, Calif.), and subject to RT-qPCR evaluation of let-7c and precursor let-7c levels. Primers used in this study are listed in Table 1. All real-time qPCR experiments were performed using iTaq Universal SYBR Green Supermix on a CFX96 real-time thermocycler (Bio-Rad, Hercules, Calif., USA). Amplicon abundance was reported relative to U6 small nucleolar RNA and vehicle control by the $2^{-\Delta\Delta Ct}$ method.

Therapy Studies in Orthotopic HCC Xenograft Mouse Models.

All animal procedures were approved by the Institutional Animal Care and Use Committee of the University of California, Davis.

Establishment of Orthotopic HCC Xenograft Mouse Model.

Luciferase/GFP-expressing Huh7 cells were mixed with Matrigel to a final concentration of 1×10⁸ cells/ml. 4-week-old male athymic nude mice (Jackson Laboratory, Bar Harbor, Me.) were anesthetized and an incision (~1 cm) along the linea alba in the midline of the abdominal muscle layer was made. 20 µL of Huh7 cells in Matrigel suspension (2×10⁶ cells) were injected into the left lobe of liver. Successful engraftment of Huh7 cells was confirmed by bioluminescent imaging using ChemiDoc™ MP Imaging System (BioRad, Hercules, Calif.), following the intraperitoneal injection of D-luciferin (150 mg/kg) (BioVision, Inc. Milpitas, Calif.).

Tumor Progression Study.

One-week post-inoculation, mice were assigned into 5 groups (Untreated, 1PEI/MSA, LPP/MSA, IPEI/let-7c and LPP/let-7c) according to tumor sizes determined by in vivo bioluminescence imaging, and treated (40 µg RNA) three times per week. Mice were imaged once per week to monitor tumor growth. Mice were sacrificed 2 h after the last dose on day 15. Livers with engrafted tumors were harvested and imaged for GFP fluorescence using ChemiDoc™ MP Imaging System. RNA was extracted from healthy livers and HCC tumors and the levels of let-7c were quantified using stem loop RT-qPCR using gene selective primers (Table 1). Blood was collected for blood chemistry profiling (Comparative Pathology Laboratory, UC Davis) and serum α-fetoprotein (AFP) was examined by ELISA (R&D Systems, Minneapolis, Minn.). Hematoxylin and eosin (H&E) histopathological study was performed by the Clinical Immunohistochemistry Laboratory at Roswell Park Cancer Institute (Buffalo, N.Y.).

Survival Study.

One-week post-inoculation, a separate batch of tumor-bearing mice were assigned into 2 groups (LPP/MSA and LPP/let-7c) according to tumor sizes determined by bioluminescence imaging, and treated with (40 µg RNA) three times per week continuously for 3 weeks. Body weights were recorded twice a week to assess animal health. Survival was analyzed by Kaplan-Meier method and compared by log-rank (Mantel-Cox) test.

Induction of Cytokine Release.

Human PMCs were purchased from Lonza (Walkerville, Md.) and maintained in RPMI 1640 supplemented with 10% human AB serum (Sigma, St. Louis, Mo.). PBMCs were seeded onto a 96-well plate at a density of 2×10⁵ cells/well and allowed to grow overnight. Cells were treated with 10 ng/mL or 100 ng/mL LPS (positive control), LPP/MSA (5 nM), LPP/let-7c (5 nM), or LPP vehicle. Twenty-four hours post-treatment, medium was harvested and cell debris was removed by centrifugation. IL-6, TNF-α, IL-4 and IL-10 levels were quantified using corresponding human cytokine ELISA assay kit (Invitrogen, Carlsbad, Calif.).

Healthy Balb/c and CD-1 mice (5-6 weeks old) were randomly assigned into different groups (3 female and 3 male per group) and injected with 40 µg of either MSA or let-7c loaded LPP nanocomplex, or 20 µg LPS (positive control), or LPP vehicle (negative control). Blood was collected 1 h post treatment and serum IL-6 and IL-4 levels were quantified using a mouse IL-6 and IL-4 ELISA assay kit (Invitrogen, Carlsbad, Calif.).

Statistical Analysis.

All values are mean±standard deviation (SD). Statistical analysis was performed using 1- or 2-way ANOVA with Bonferroni's post-hoc test or Student's t-test where appropriate (GraphPad Prism, San Diego, Calif.).

Results

Bioengineered Let-7c is the Most Potent Inhibitor Against HCC Cell Proliferation Among a Collection of ncRNA Agents.

Figure 1B:
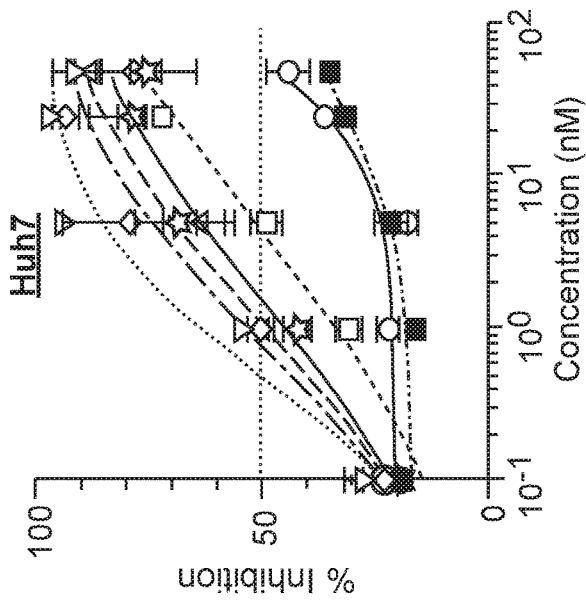
Figure 1C:
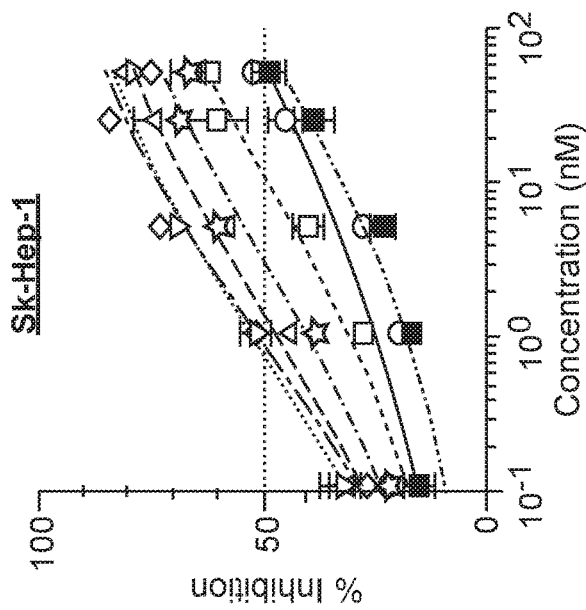
Figure 2A:
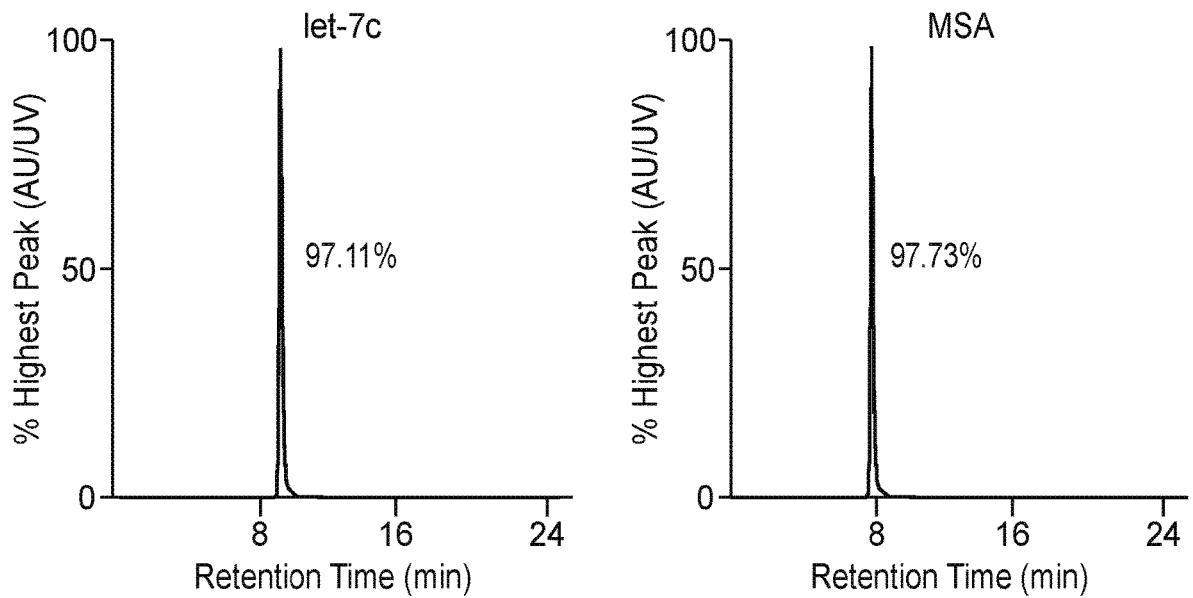
FIGS. 2A-B illustrate that isolated let-7c and control MSA agents are >97% pure with an endotoxin level <3 EU/μg RNA, which were determined by HPLC and Pyrogent-5000 kinetic LAL assay, respectively.
Figure 2B:
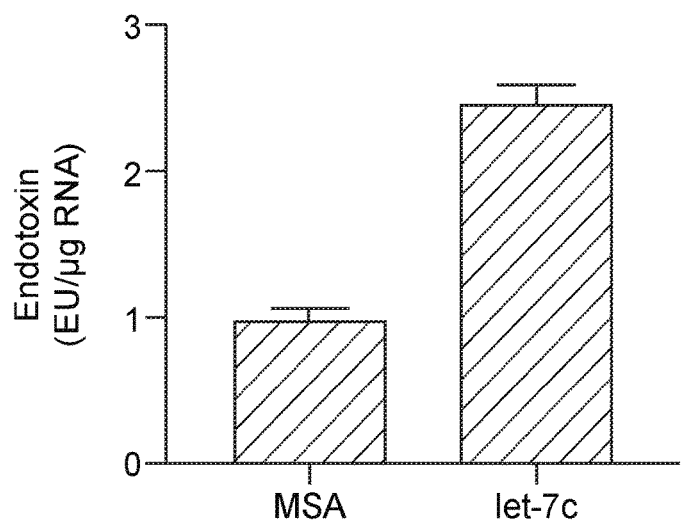

Screening of a small collection of bioengineered miRNA agents was predictive for their anti-proliferative activities, as control RNA (MSA) consistently yielded the least inhibition of cell viability (FIG. 1A). A number of miRNA agents showing overlapped and greater antiproliferative activities in both cell lines, including miR-298, miR-124, let-7c, miR-328, miR-144, and miR-126, were pursued for dose response study (FIG. 1B). Let-7c was revealed as the most potent ncRNA, with EC50 values of 0.78 and 0.51 nM in Sk-Hep-1 and Huh7 cells, respectively (FIG. 1C). Furthermore, let-7c was as pure (>97%, by HPLC) as other tested ncRNAs (FIG. 1) purified by the same anion exchange FPLC method (21) and had a low endotoxin level (FIG. 2), suggesting a minimal interference by impurities.

Bioengineered Let-7c Reduces Protein Levels of Target Genes.

Figure 3A:
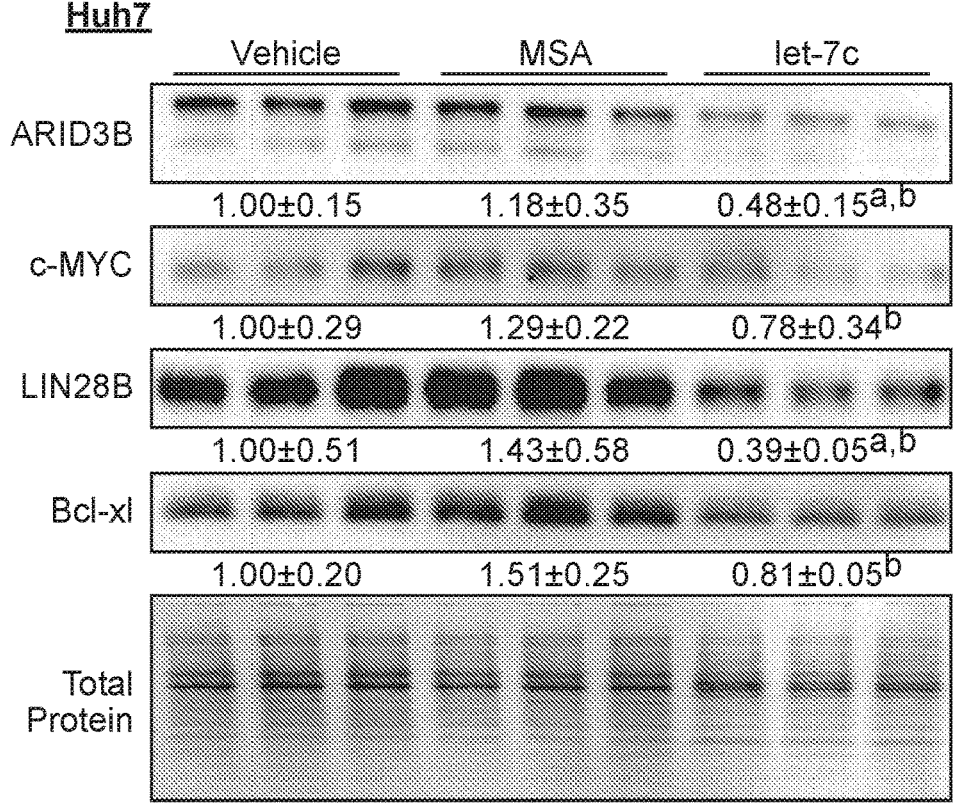
FIGS. 3A-B illustrates suppression of protein levels of target genes by bioengineered let-7c in HCC cell lines. (A) Immunoblot analyses of let-7c targeted ARID3B, c-MYC, LIN28B and Bcl-xl protein levels and (B) immunofluorescent analysis of HMGA2 in Huh7 and Sk-Hep-1 cells treated with 15 nM let-7c or control MSA Immunoblot intensity was normalized to total protein and vehicle control for comparison between groups; P<0.05 compared to vehicle (a) or MSA (b) (1-way ANOVA with Bonferroni's post-hoc test). Immunofluorescent intensity of HMGA2 staining was normalized to total DAPI-positive cells. *P<0.05 compared to MSA (Student's t-test).
Figure 3A:
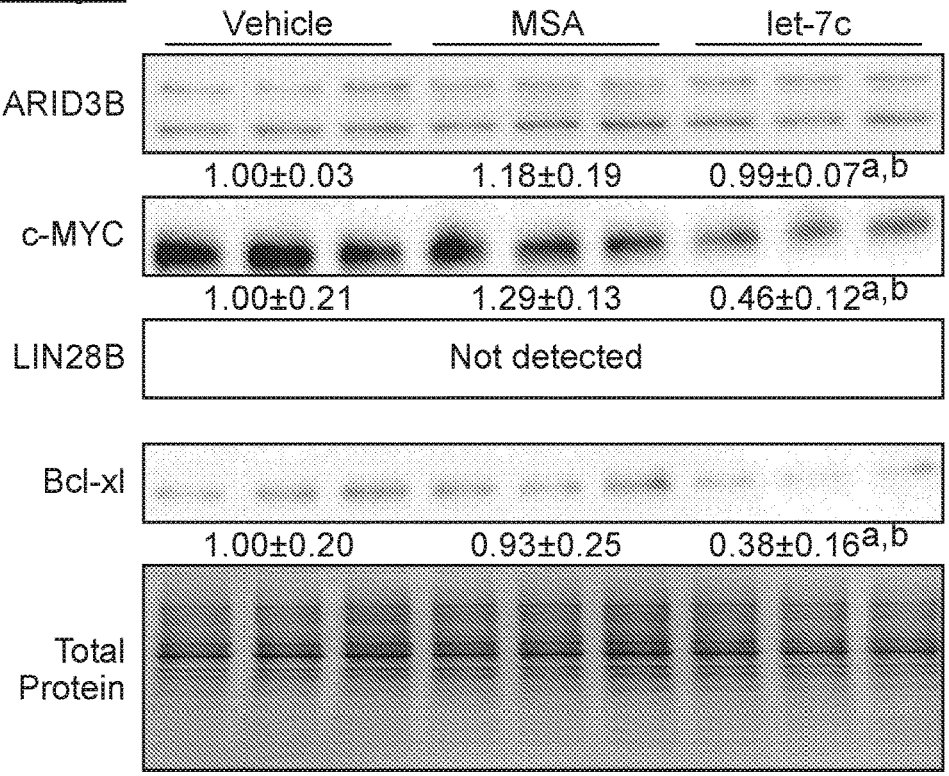
Figure 3B:
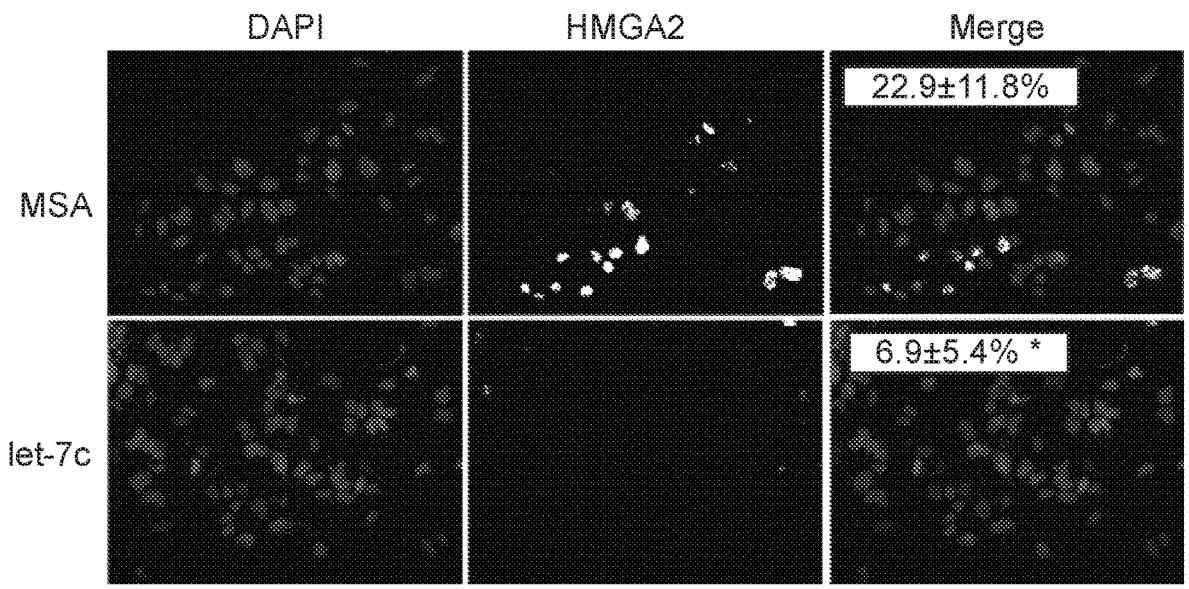
Figure 3B:
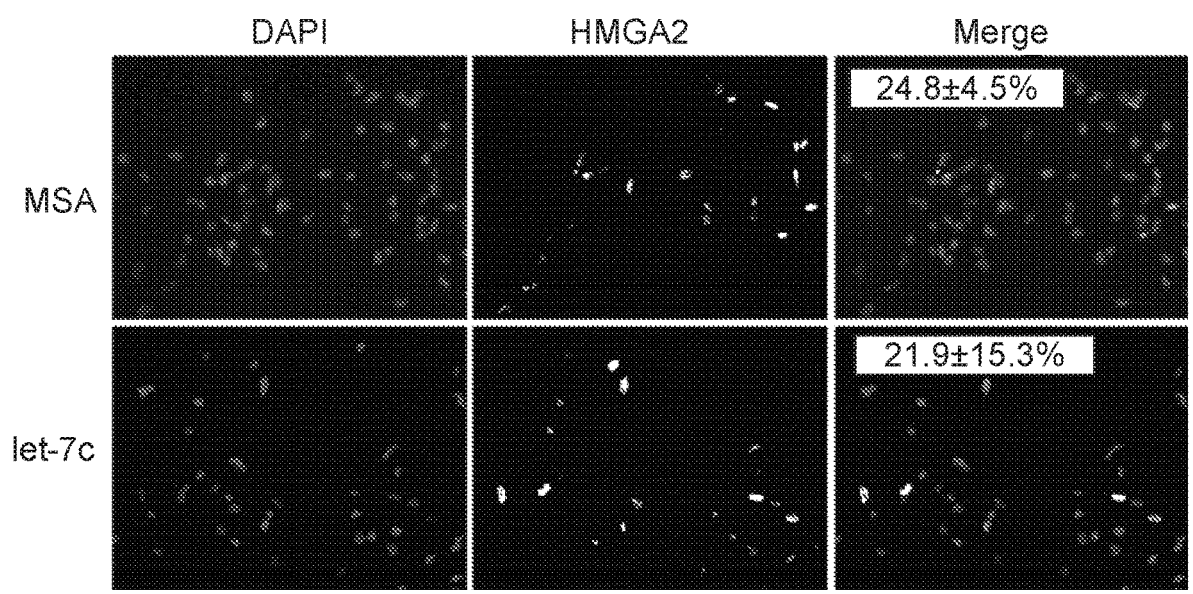

To verify the actions of recombinant let-7c, we examined protein levels of several known let-7 targets important in cancer. LIN28B, a canonical target of let-7 family miRNAs, was reduced by let-7c over 60% in Huh7 cells, while it was not detected in Sk-Hep-1 cells by immunoblot (FIG. 3A). This was associated with much higher levels of let-7c in cells treated with biologic let-7c-than control MSA. Furthermore, Bcl-xl and c-Myc protein levels were suppressed consistently by let-7c in both Huh7 and Sk-Hep-1 cells, whereas downregulation of ARID3B was only observed in Huh7 cells. In addition, immunofluorescence study demonstrated that HMGA2 expression was reduced significantly in Huh7 cells, whereas it was not significantly in Sk-Hep-1 cells (FIG. 3B).

Induction of Apoptosis of HCC Cells by Bioengineered Let-7c.

Figure 4:
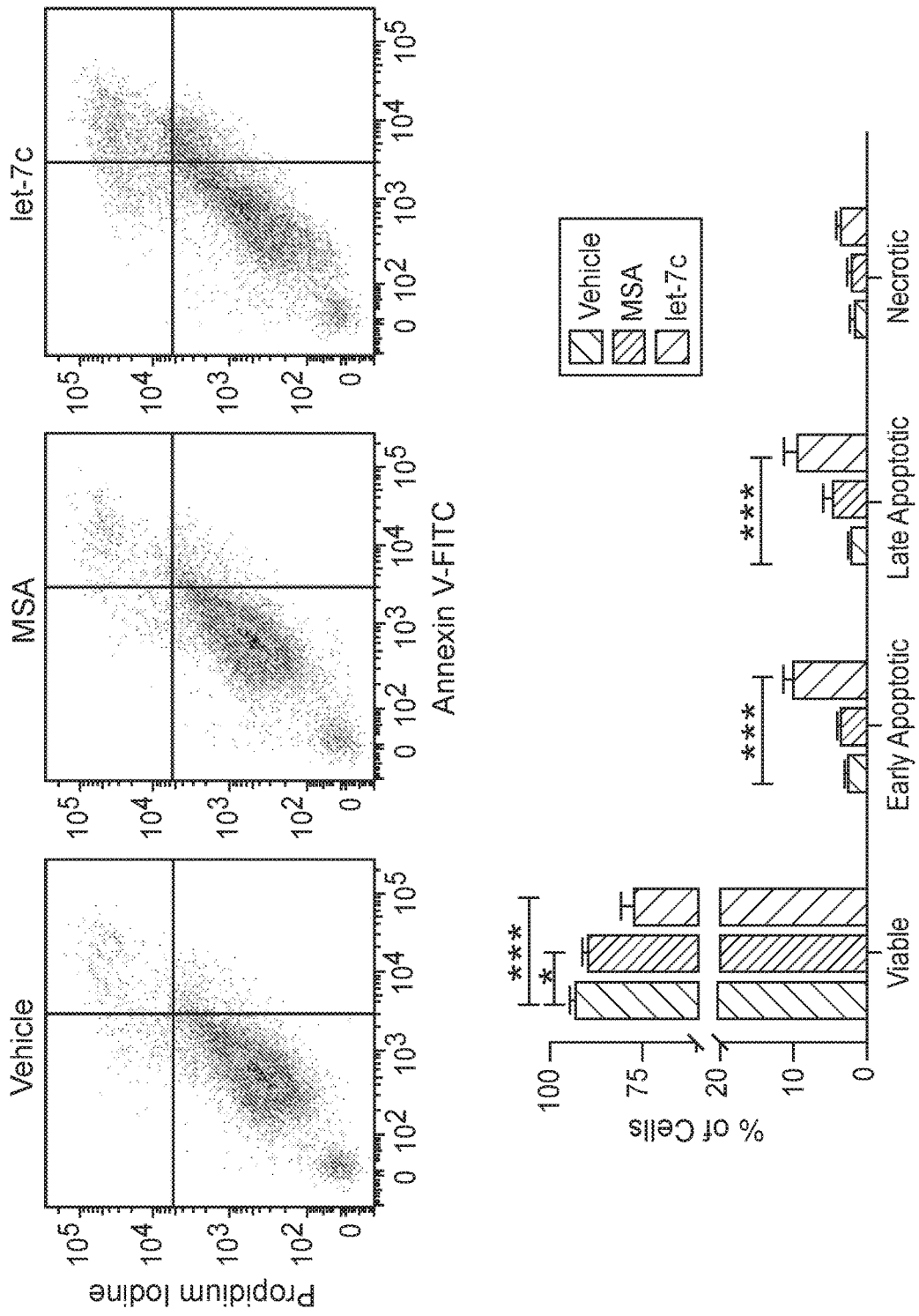
FIG. 4 illustrates apoptotic cell death is significantly induced by bioengineered let-7c. Sk-Hep-1 and Huh7 cells were transfected with 5 nM of MSA or let-7c for 48 h, stained with propidium iodide and Annexin V-FITC, and counted by a flow cytometer with a total cell gate of 10,000 events. A significant shift of the total population towards early and late apoptotic cells was observed, while total necrotic population showed no difference. Values are mean±SD (N=3 per group). *P<0.05, P<0.01, *P<0.001 (1-way ANOVA with Bonferroni's post-hoc test).
Figure 4:
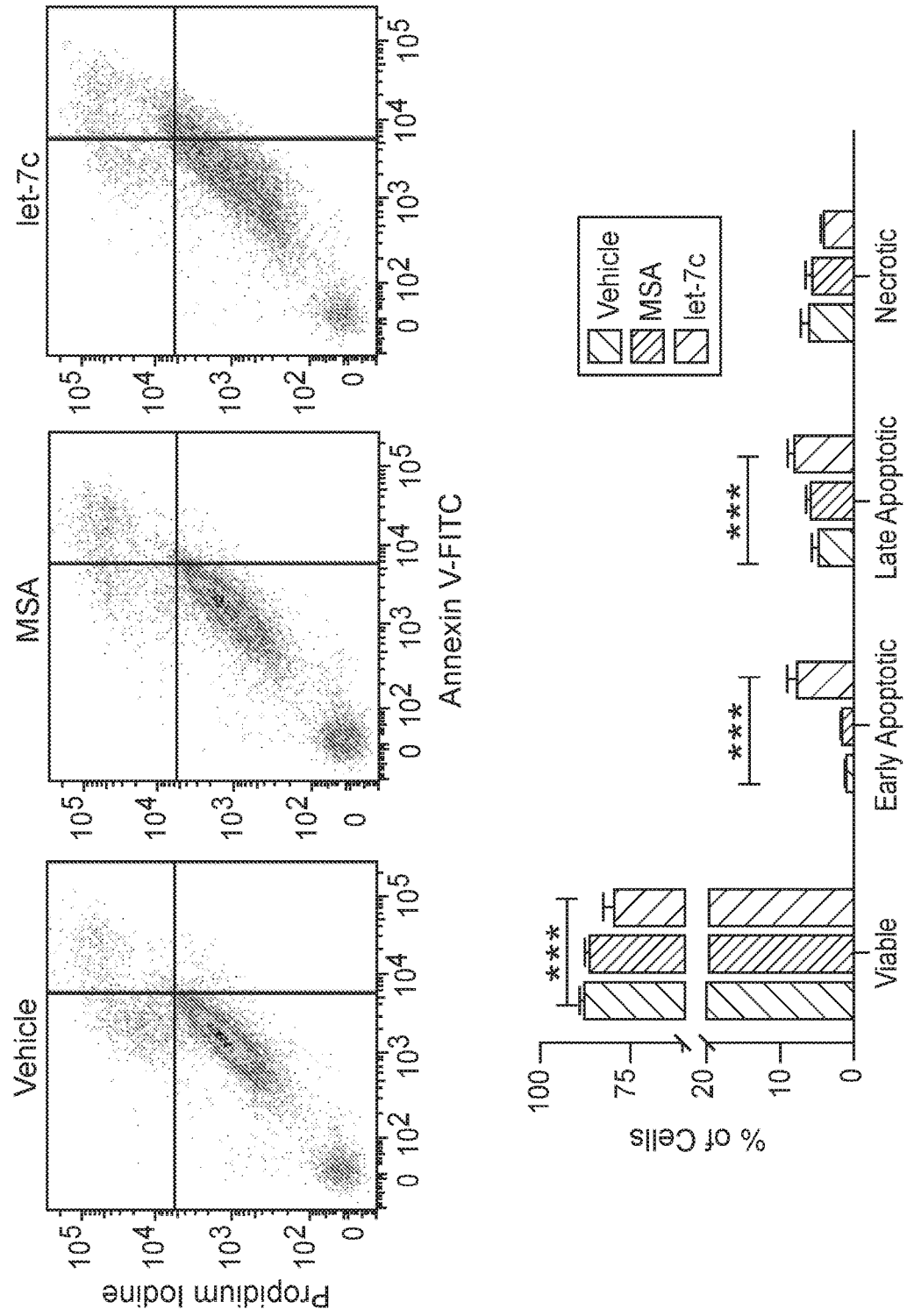
Figure 5A:
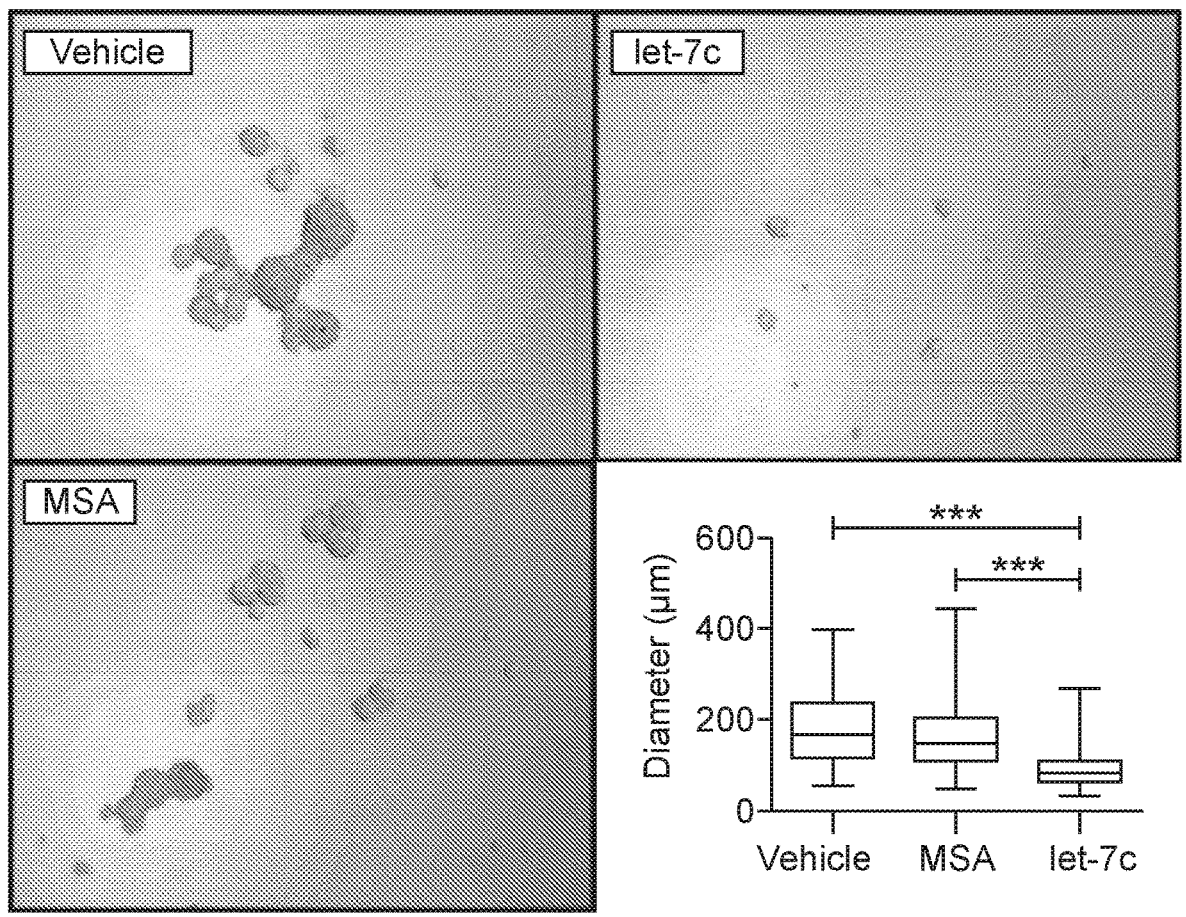
FIG. 5A-B illustrates bioengineered let-7c sharply reduces tumorsphere growth. Following transfection with MSA or let-7c in adherent conditions, an equal number of Huh7 cells were grown in serum-free/ultra-low attachment conditions for 7 days to yield primary tumorspheres. Primary tumorspheres were then digested to single-cell, transfected again, and grown for another 7 days in serum-free/ultra-low attachment conditions to yield secondary tumorspheres. let-7c treatment resulted in smaller primary and secondary tumorspheres. Values are mean±SD (N=3 per group). *P<0.05, P<0.01, *P<0.001 (1-way ANOVA with Bonferroni's post-hoc test).
Figure 5A:
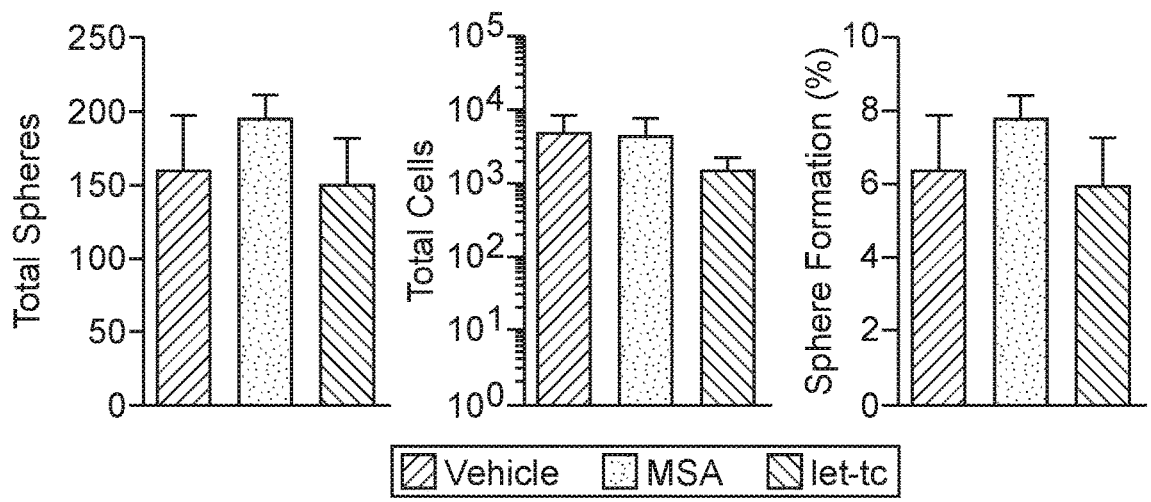
Figure 5B:
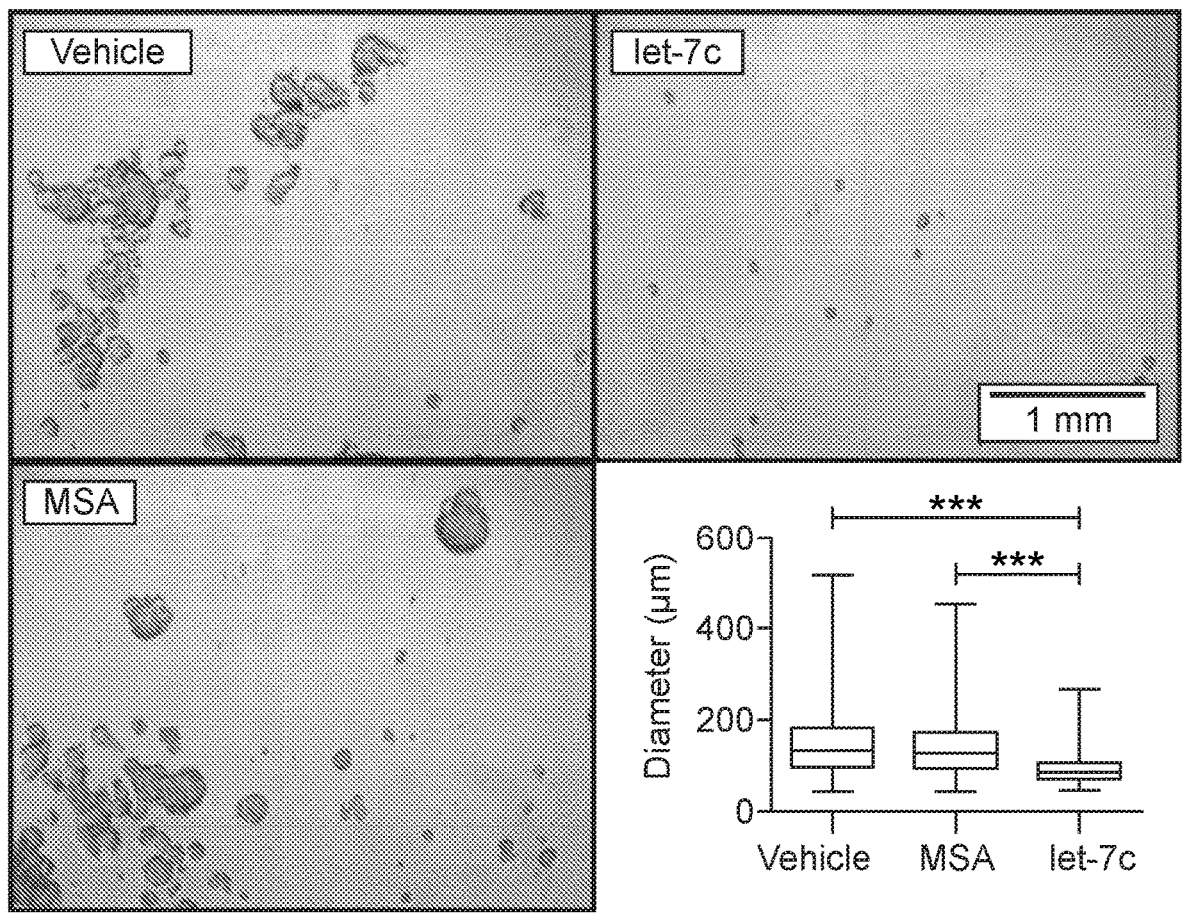
Figure 5B:
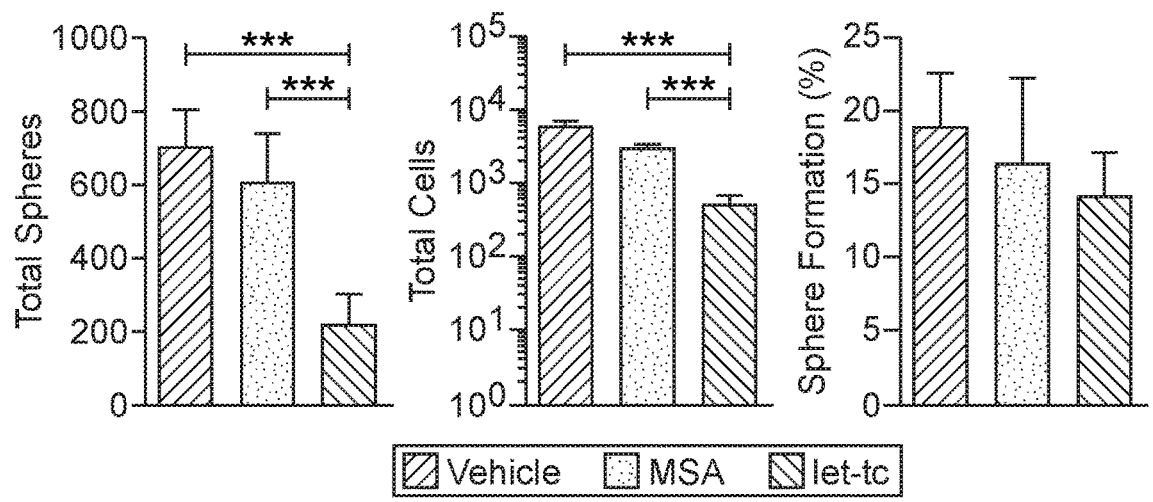

Let-7 family miRNAs have been shown to induce apoptosis via targeting of Bcl-xl, among other mechanisms (32). Likewise, our data showed that a low dose (5 nM) of let-7c induced a modest yet robust increase in early and late apoptotic cell populations in both Huh7 and Sk-Hep-1 cells (FIG. 4), compared to vehicle- and MSA treatments. Additionally, necrotic cell populations were not altered following the transfection of let-7c and MSA.

Biologic Let-7c Suppresses HCC Cell Sternness.

Negative feedback between let-7 and LIN28 influences the stemness of cancer cells (33) critical for therapeutic outcomes. As such, we evaluated cancer stem cell (CSC) growth using a tumorsphere assay in Huh7 cells; Sk-Hep-1 cells did not form tumorshperes under similar conditions. Following transfection in adherent conditions and subsequent growth in ultra-low attachment/serum-free conditions, we observed a significant half-diameter reduction in primary tumorsphere size, but not tumorsphere count, in let-7c-treated cells (FIG. 5). Upon subsequent dissociation, transfection, and growth in ultra-low attachment/serum-free conditions to form secondary tumorspheres, a similar 50% reduction in diameter was observed in let-7c-treated cells. While sphere formation efficiency from primary tumorspheres was not significantly reduced, sphere count and individual cell number were significantly reduced in secondary tumorspheres by let-7c treatment (FIG. 5).

Preparation and Characterization of Let-7c-Loaded LPP Nanocomplex.

Figure 6A:
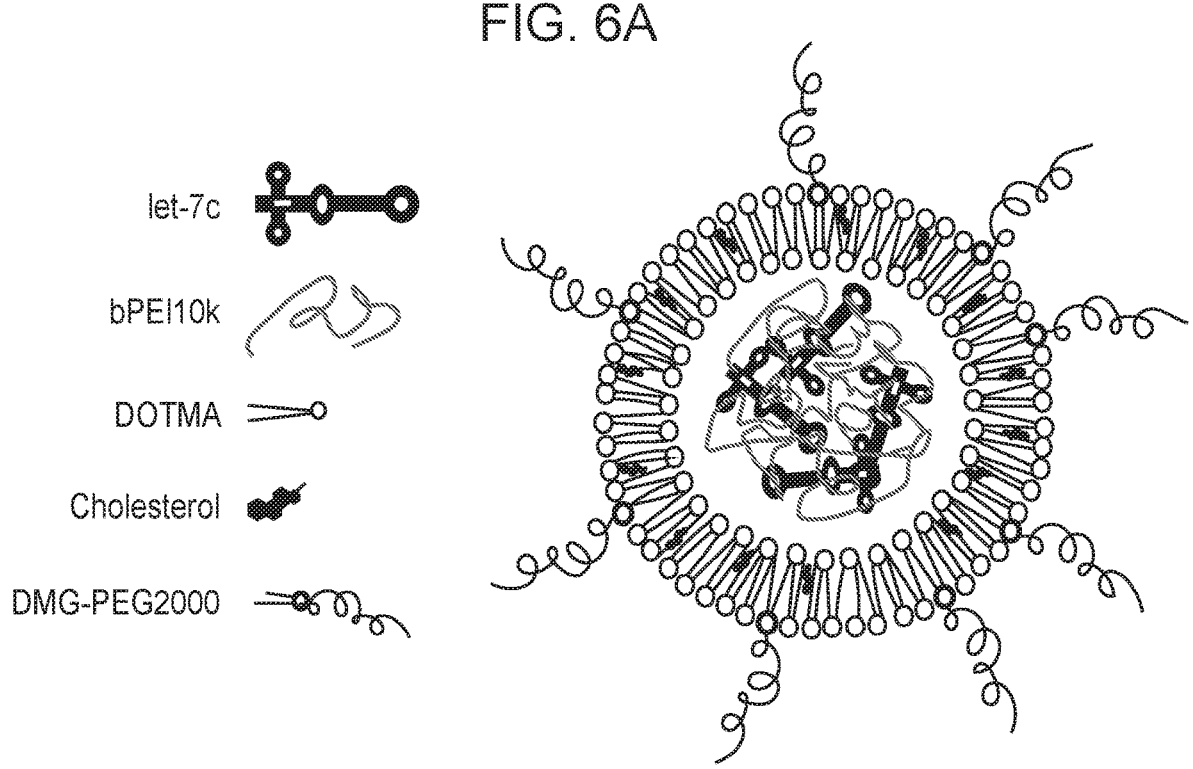
FIGS. 6A-F illustrate that Let-7c is efficiently delivered into HCC cells by LPP nanocomplex to control cell proliferation. (A) Schematic illustration of let-7c-loaded lipopolyplex (LPP). (B) TEM image of let-7c-loaded LPP (indicated by red arrows) nanocomplex, as well as the size and zeta potential measured by dynamic light scattering. Bar indicates 500 nm. (C and E) Efficient delivery of let-7c (15 nM) led to sharp suppression of Huh7 and Sk-Hep-1 cell growth (D and F). Lipofectamine 3000 (LF3000) treatments were used for comparison. Values are mean±SD of triplicate treatments (N=3 per group). P<0.01 and *P<0.001 (1- or 2-way ANOVA with Bonferroni's post-hoc test).
Figure 6B:
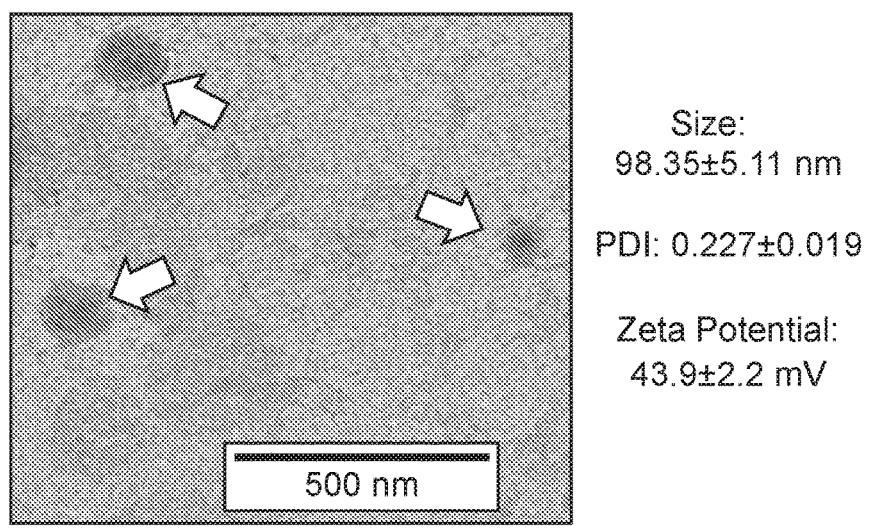
Figure 7:
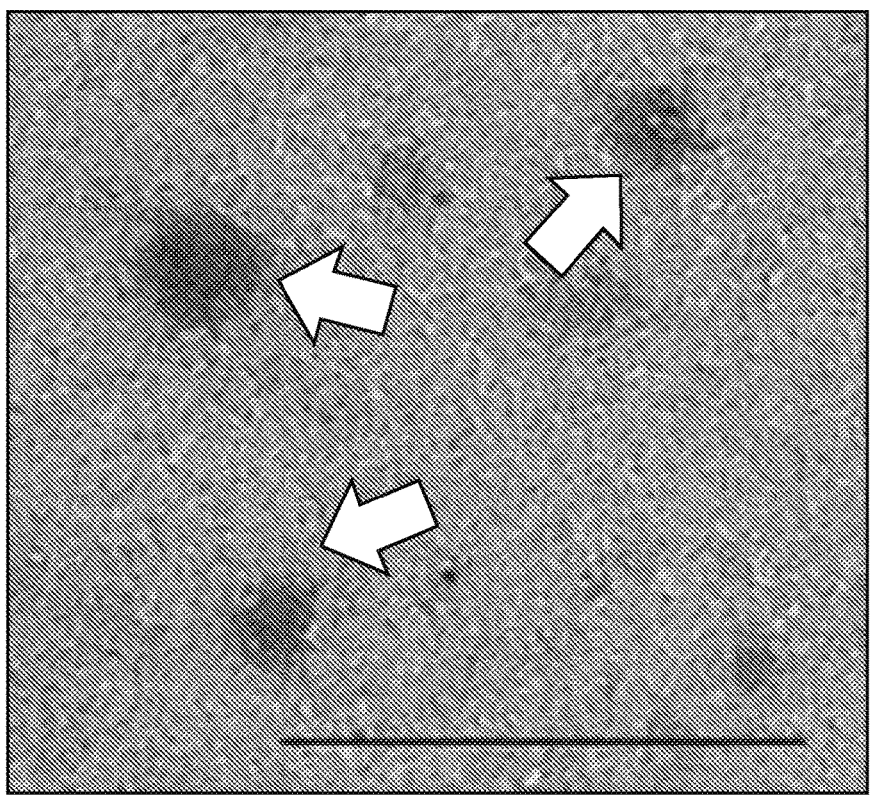
FIG. 7 illustrates transmission electron microscopy (TEM) examination of LPP/MSA nanocomplex. Particle size and zeta potential were measured by dynamic light scattering.
Figure 8A:
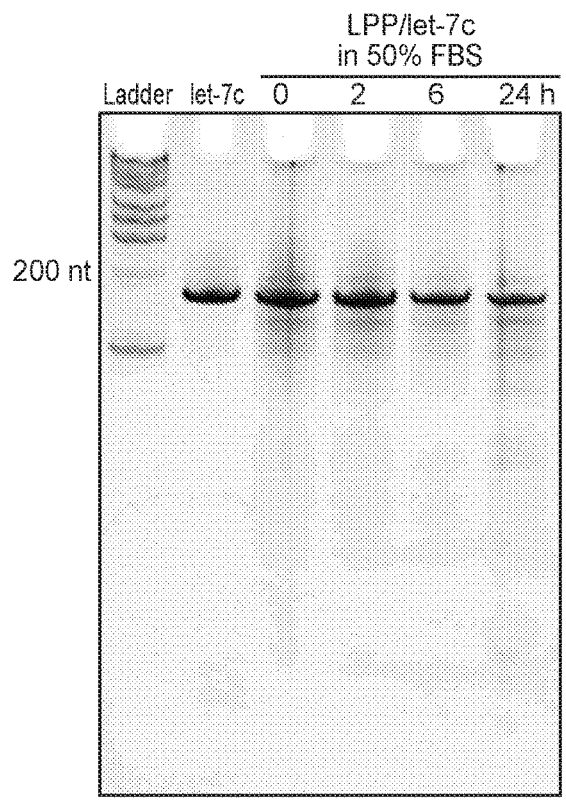
FIGS. 8A-C illustrate serum stability of LPP/let-7c nanocomplex, in comparison to IPEI/let-7c formulation. Shown are urea-PAGE analyses of isolated let-7c after different let-7c formulations were incubated in serum for 0, 2, 6 and 24 h under 37° C.
Figure 8B:
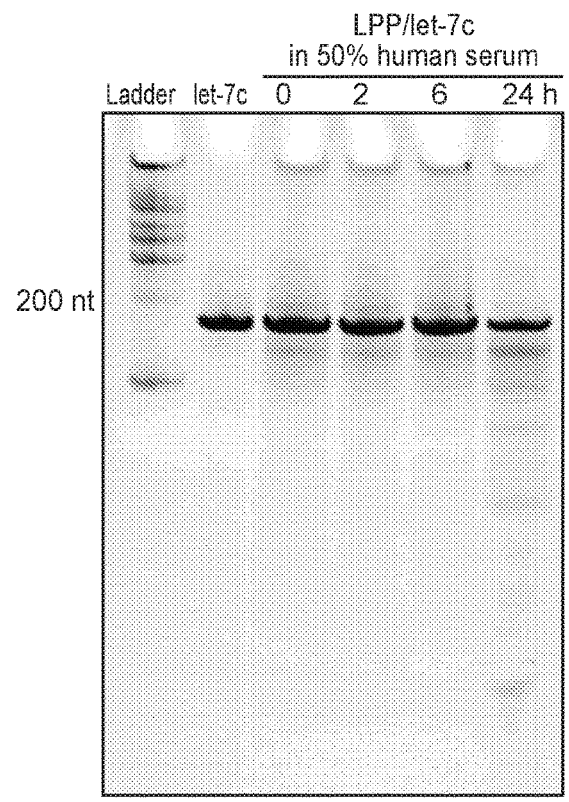
Figure 8C:
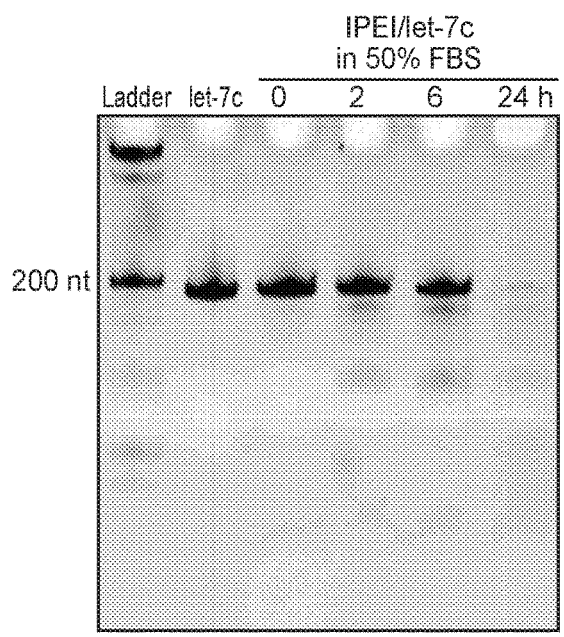

We thus employed LPP to load bioengineered let-7c molecule (FIG. 6A) towards therapy study in animal models. The size of let-7c-loaded LPP was 98.35±5.11 nm with a zeta potential value of 43.9±2.2 mV, which was complemented by TEM examination (FIG. 6B). Control RNA MSA was formulated in the same manner and LPP/MSA nanocomplex showed similar size (102.4±5.9 nm) and zeta potential (45.1±1.2 mV) (FIG. 7). In addition, LPP could effectively protect let-7c from degradation in both FBS and human serum up to 24 h (FIG. 8A-B), to a greater degree than polyplex (FIG. 8C).

LPP Efficiently Delivers Let-7c into HCC Cells to Elicit Inhibition of Cell Growth.

Figure 6C:
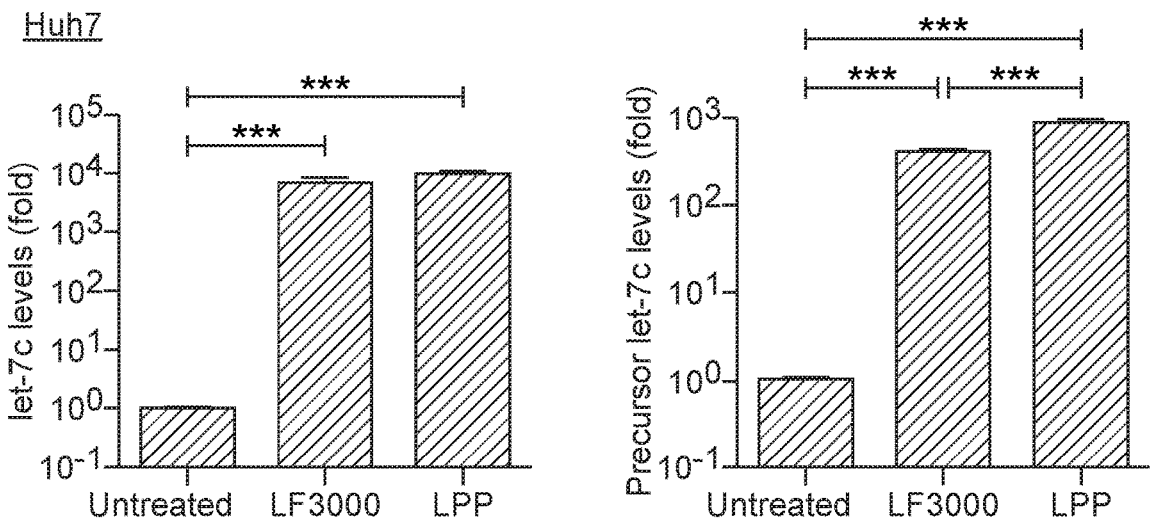
Figure 6D:
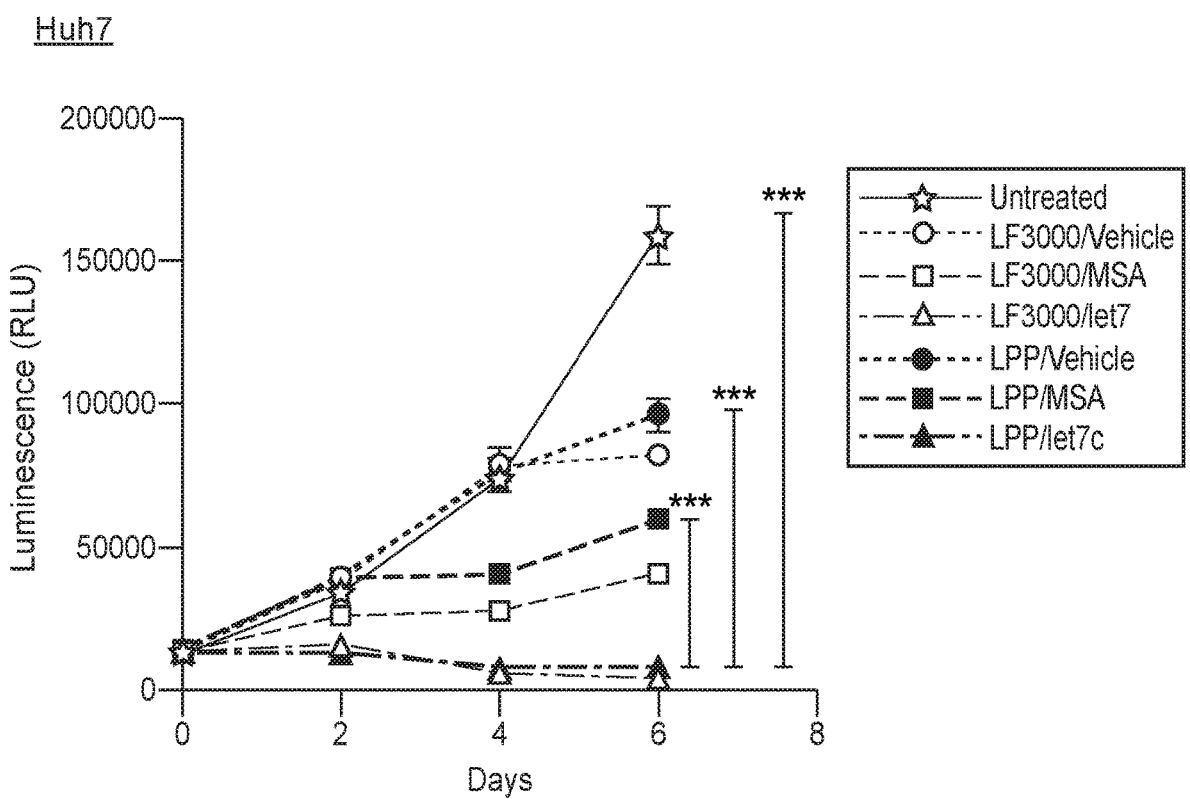
Figure 6E:
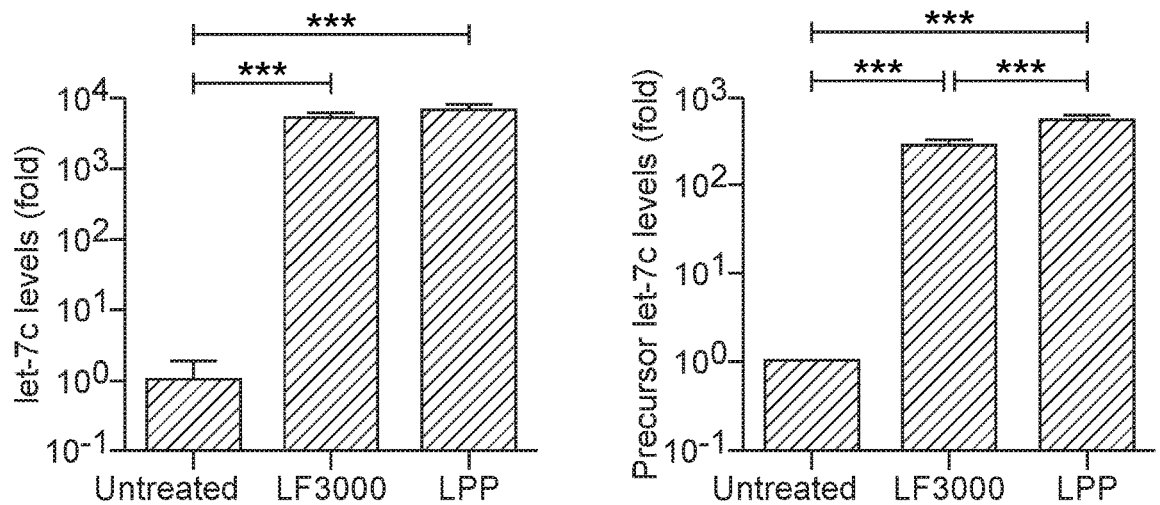
Figure 6F:
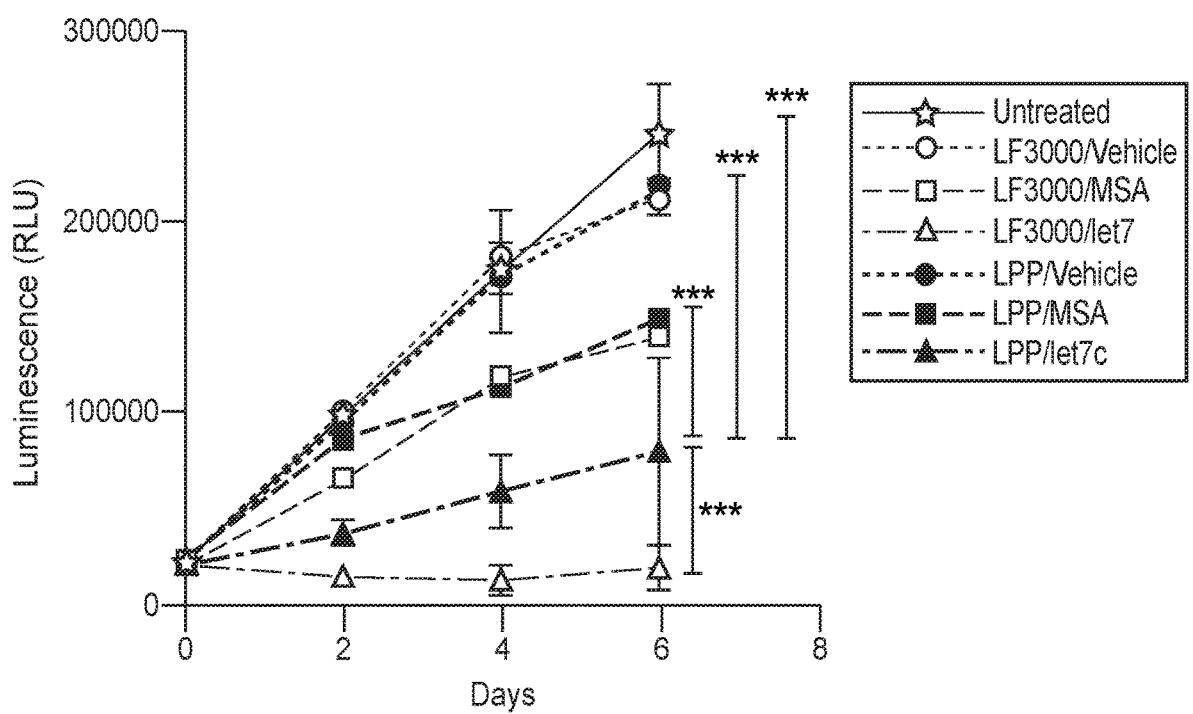
Figure 9:
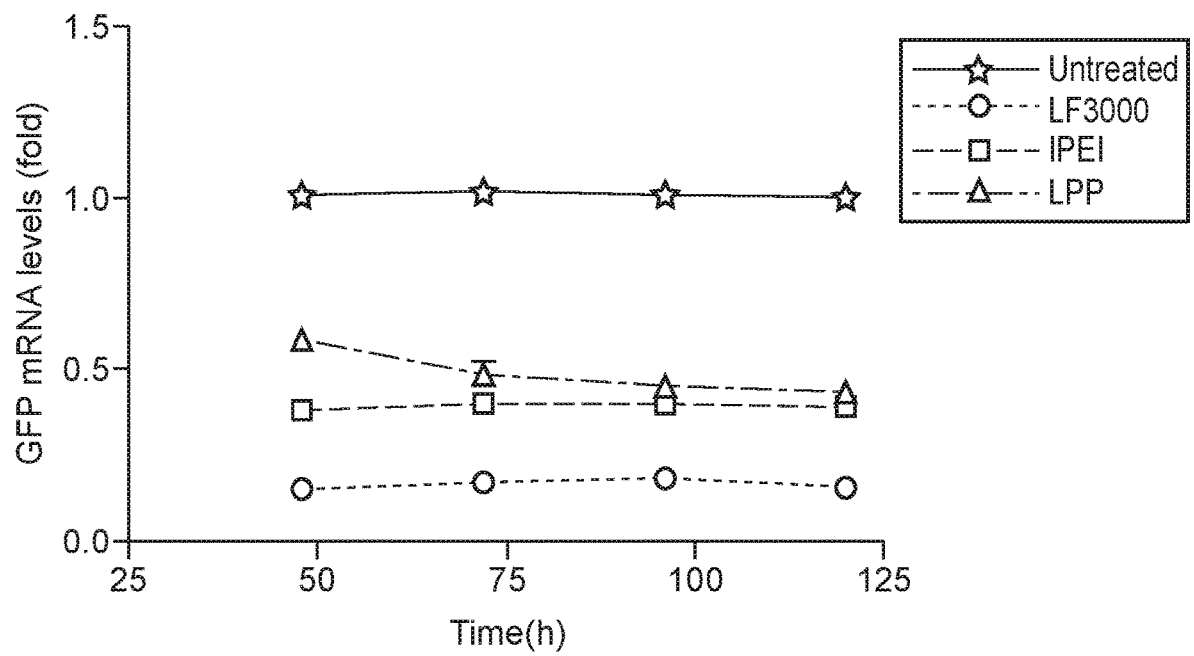
FIG. 9 illustrates LPP is effective to delivery bioengineered ncRNA for target gene regulation, as demonstrated by the delivery of bioengineered GFP-siRNA (5 nM) and effective reduction of target GFP mRNA levels in GFP/luciferase-expressing SK-Hep1 cells. Lipofectamine 3000 (LP3000) and in vivo-jetPEI (IPEI) formulations were used for comparison. GFP mRNA levels were determined by selective RT-qPCR assay. Values are mean±SD of triplicate treatments (N=3 per group).

We further assessed delivery efficiency by LPP in both Huh7 and Sk-Hep-1 cells, in parallel to Lipofectamine 3000 (LF3000). Our data demonstrated that let-7c was efficiently delivered into Huh7 cells by LPP nanocomplex, as manifested by the increase in comparable level of let-7c as LF3000 formulations (FIG. 6C), which led to a sharp suppression of cell proliferation (FIG. 6D). Similar results were observed for LF3000- and LPP-formulated let-7c in Sk-Hep-1 cells (FIG. 6E-F). These data were also complemented by efficient delivery of another bioengineered ncRNA molecule, GFP-siRNA (20, 21), by LPP nanoparticles, as indicated by the knockdown of target GFP levels in GFP/luciferase-expressing Huh7 cells (FIG. 9).

Bioengineered Let-7c Significantly Reduces HCC Tumor Progression in Orthotopic Xenograft Mouse Models and it is Well Tolerated.

Figure 10A:
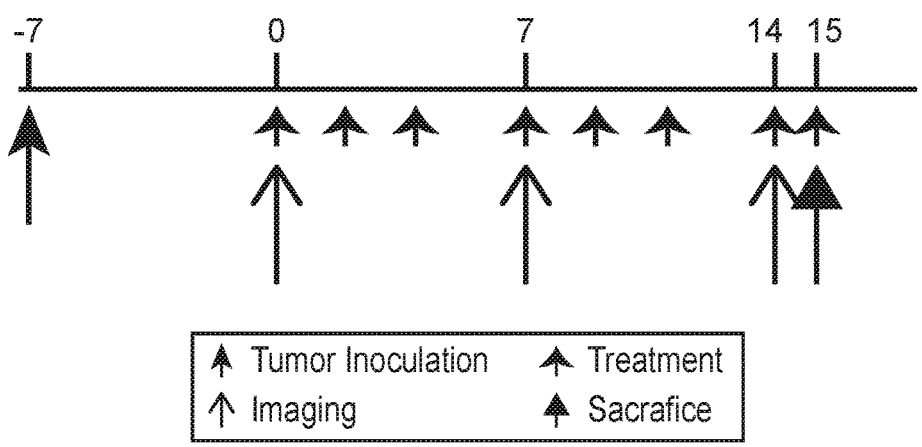
Figure 10C:
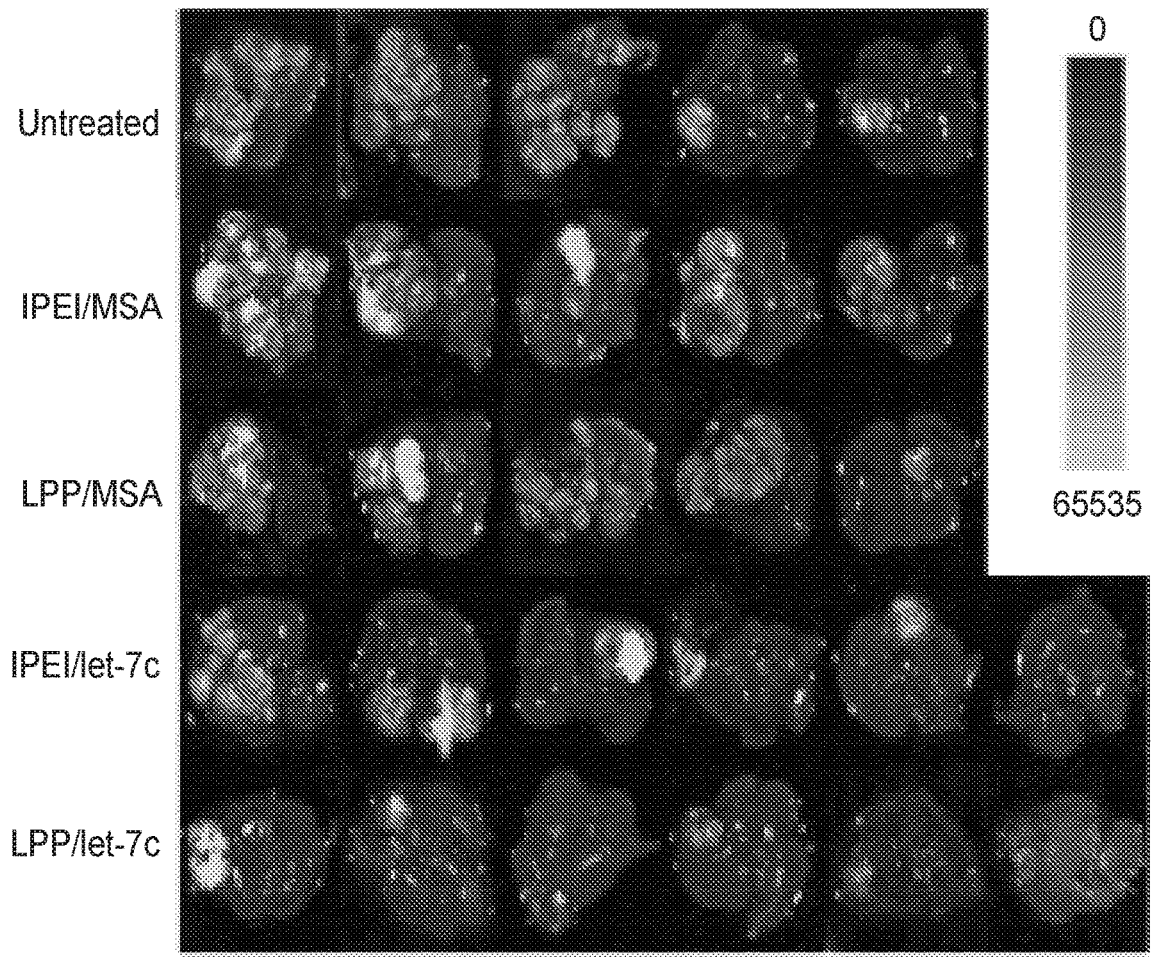
Figure 10C:
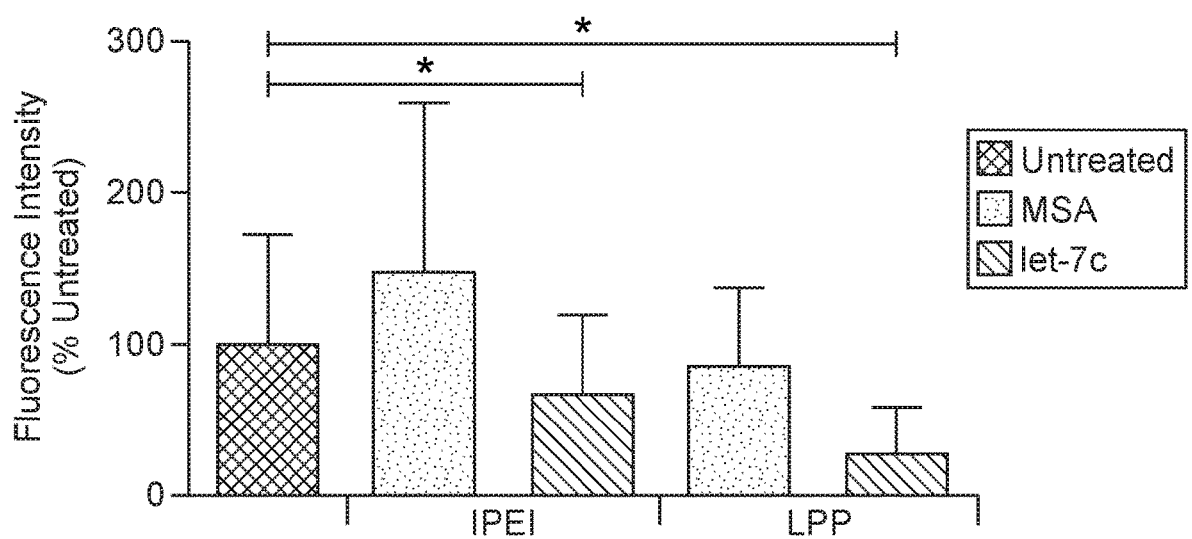
Figure 10D:
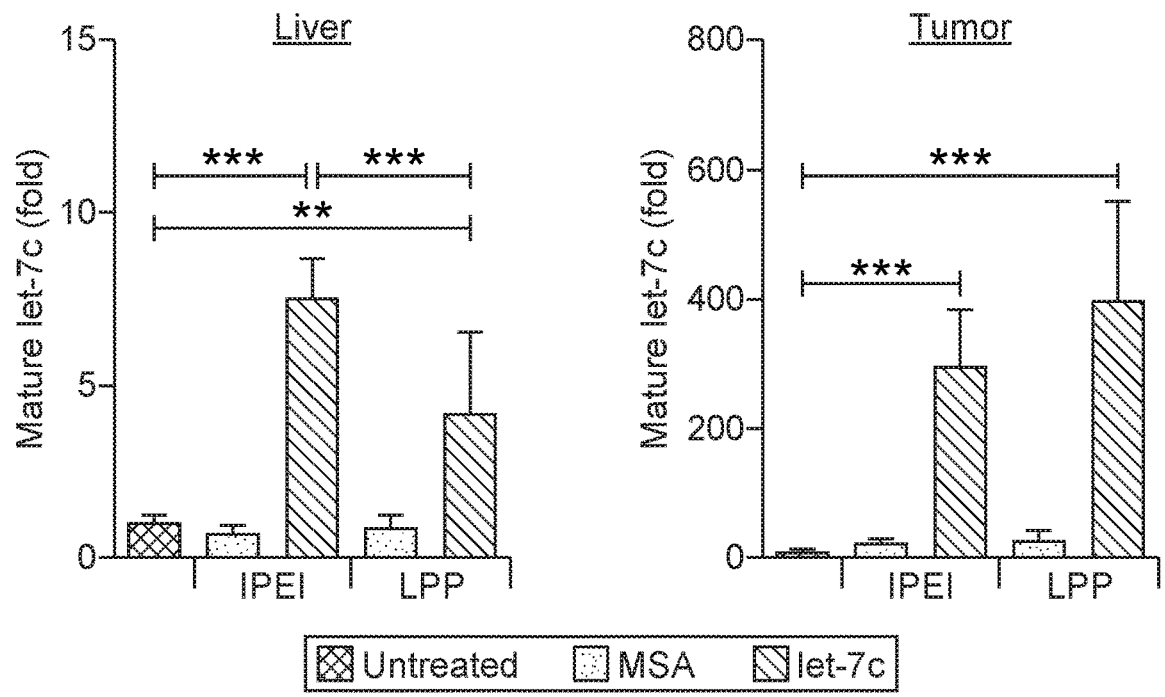
Figure 10E:
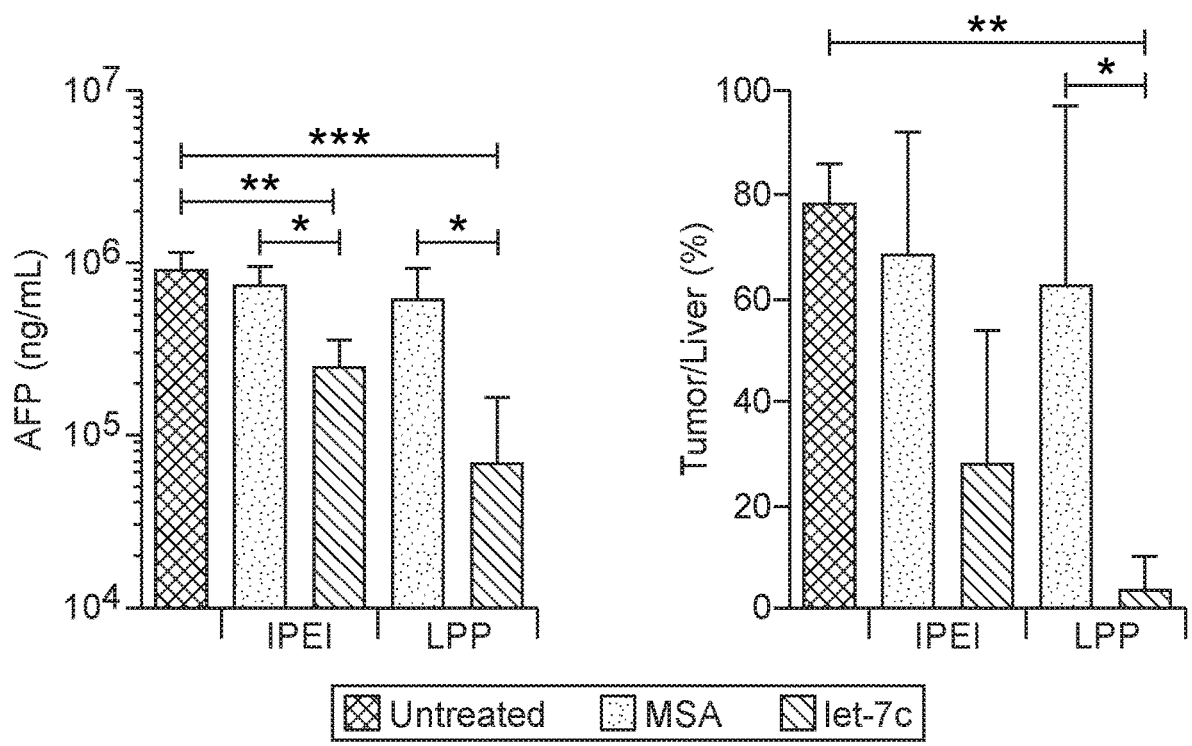
Figure 10F:
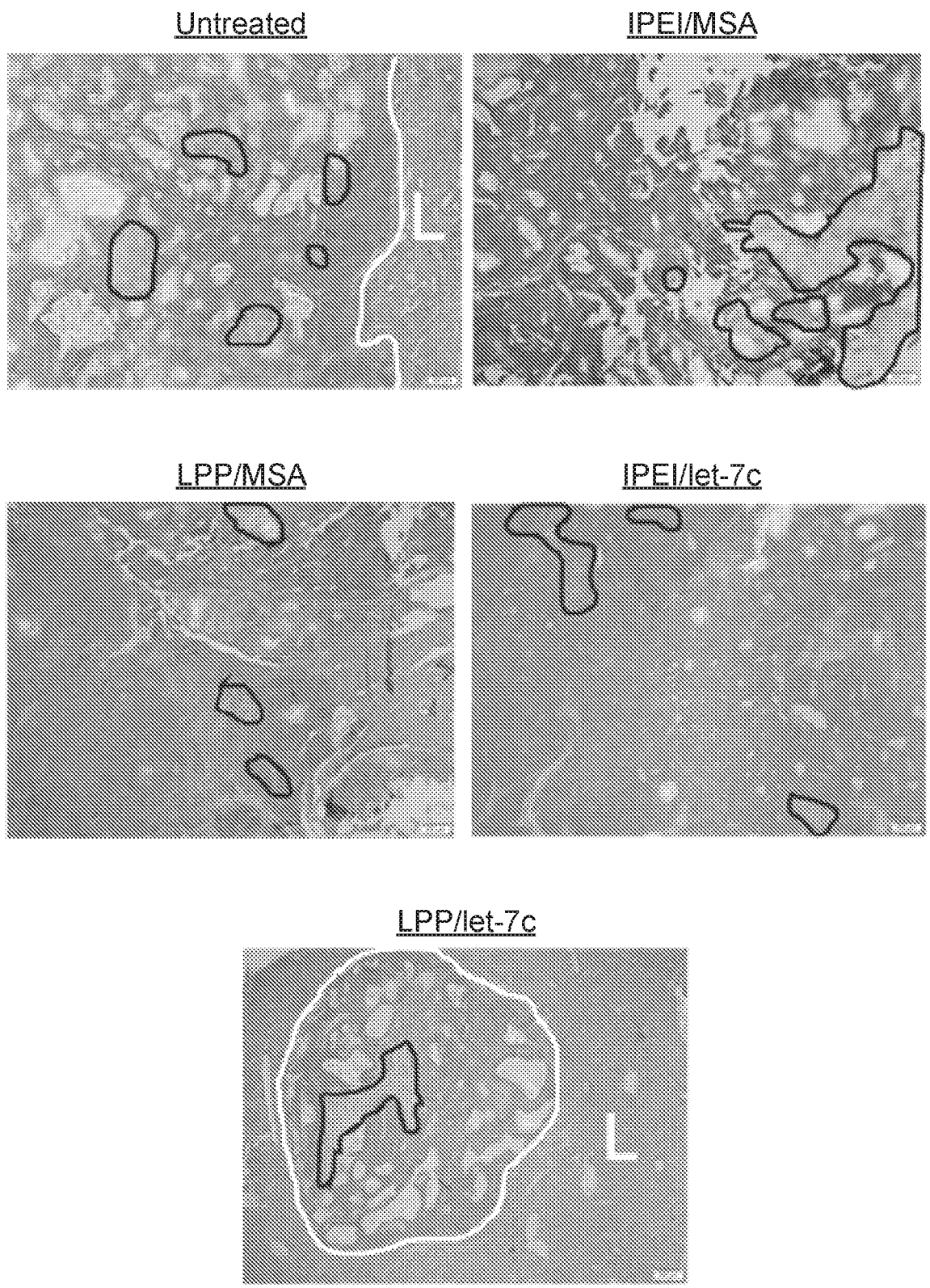

We thus established orthotopic HCC xenograft mouse models with luciferase/GFP-expressing Huh7 cells to investigate the efficacy of let-7c therapy (FIG. 10A). As revealed by bioluminescent imaging in live animals (FIG. 10B), HCC tumor burden was inhibited by approximately 50% by both LPP- and IPEI-delivered let-7c, compared to untreated mice; whereas control MSA had no impact. Ex vivo imaging of liver tumoral GFP signals (FIG. 10C) further demonstrated the effectiveness of let-7c for the control of HCC, which was reduced over 70% by LPP/let-7c and around 33% by IPEI/let-7c as compared with untreated mice. Suppression of HCC was associated with higher levels of let-7c in both healthy livers and tumors isolated from let-7c treated mice (FIG. 10D). In addition, efficacy of let-7c therapy in the inhibition of orthotopic HCC was supported significant lower serum AFP levels in let-7c-treated mice (FIG. 10E), as well as histopathological examination of HCC tissues (FIG. 10F). It is also noteworthy that, consistent with a greater serum stability (FIG. 8), LPP/let-7c was more effective than IPEI/let-7c in the control of HCC, as indicated by a more ubiquitous and significantly greater degree of reduction of tumor burden (FIG. 10).

Figure 11A:
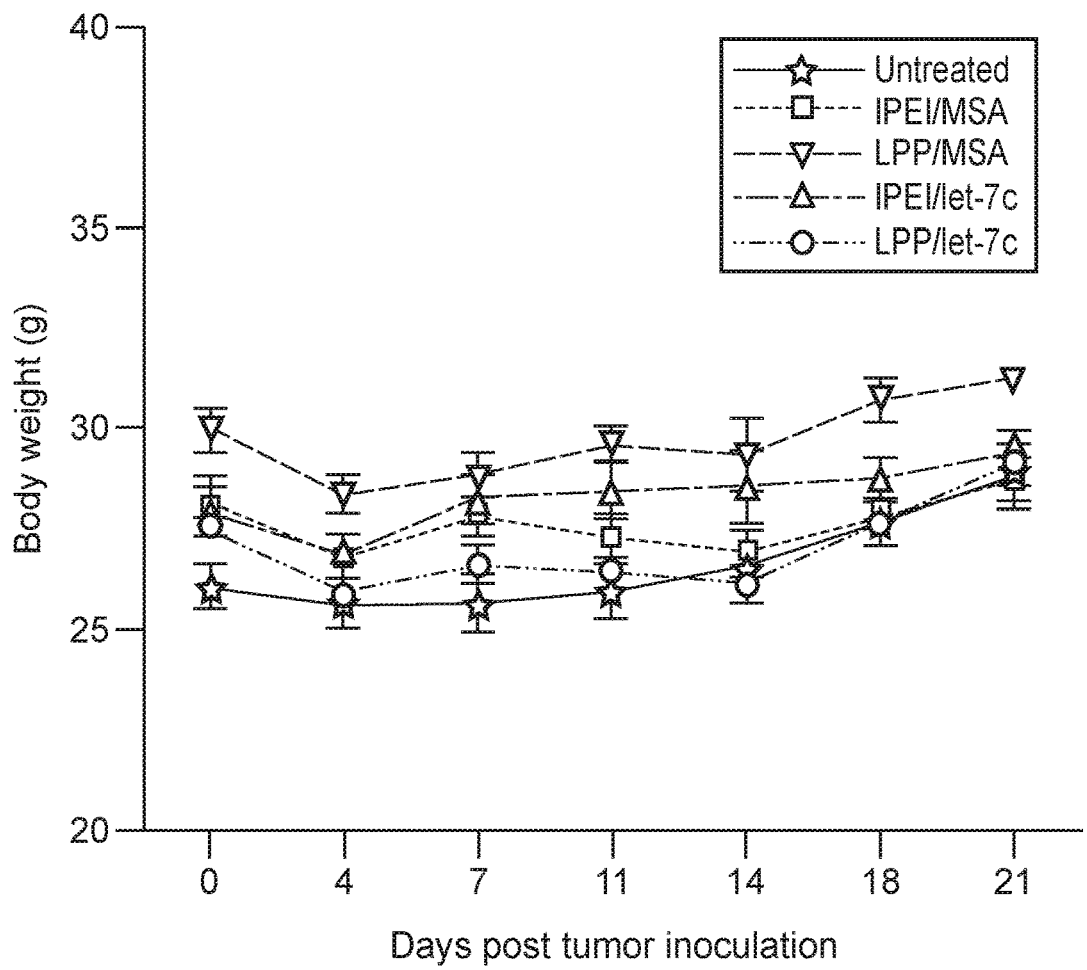

All treatments were well tolerated as body weights of all mice showed steady increases over time (FIG. 11A). To further investigate the safety of let-7c, blood biochemistry profiles were determined (FIG. 9B-F). Biomarkers of hepatic and renal functions including alanine aminotransferase (ALT), aspartate aminotransferase (AST), blood urea nitrogen (BUN) and creatinine were all within the normal ranges. To our surprise, blood total bilirubin levels in untreated and MSA-treated mice were highly variable and inclined to be above normal range, whereas they retained within normal range in let-7c-treated mice, which may be another indication of effectiveness of let-7c in the control of HCC.

LPP/Let-7c Nanotherapeutics Significantly Improves the Overall Survival of Orthotopic HCC Tumor-Bearing Mice.

Figure 11B:
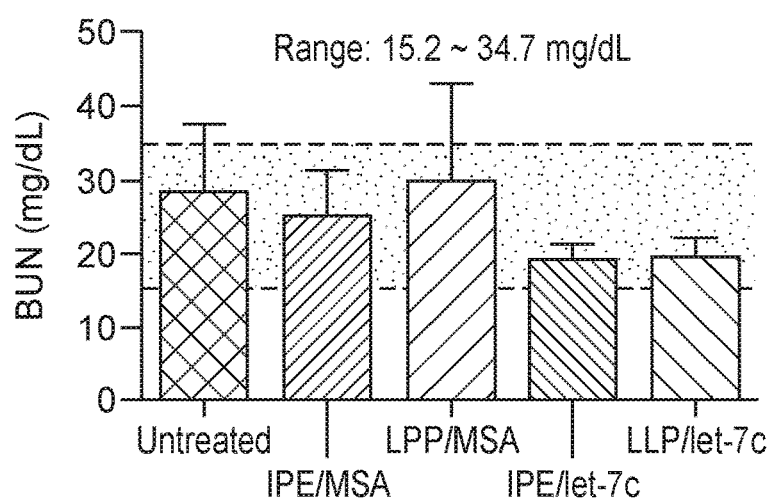
Figure 12A:
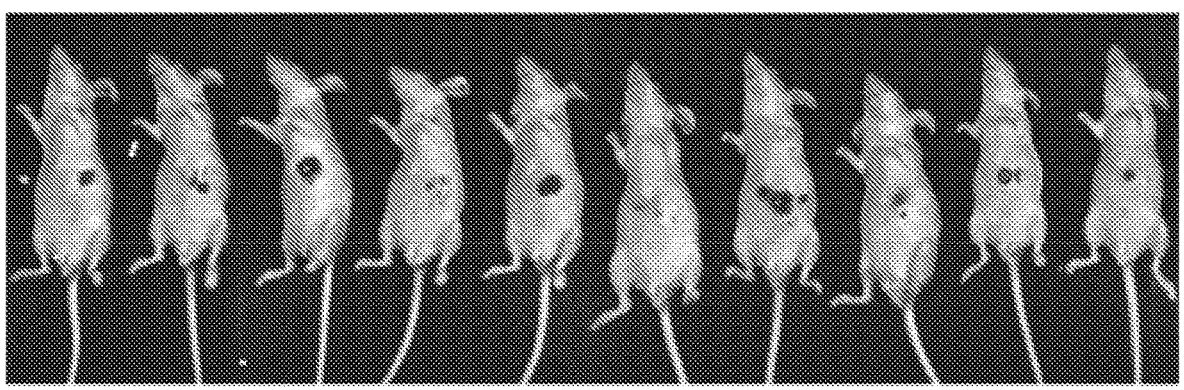
FIGS. 12A-C illustrate that LPP/let-7c nanotherapeutics significantly improves overall survival of orthotopic HCC xenograft tumor-bearing mice. (A) Bioluminescence images of HCC tumor-bearing animals before the treatment with LPP/let-7c and control LPP/MSA, and quantitative measurement of bioluminescent intensities. (B) Survival analysis showed that LPP/let-7c-treated mice lived much longer than the control (**P<0.01; N=10 per group; Log-rank (Mantel-Cox) Test). The median survival was 26.0 days for LPP/let-7c-treated mice and 19.5 days for LPP/MSA-treated animals. (C) Mouse body weights during the treatment. indicates days on which mice received treatments.
Figure 12A:
Figure 12A:
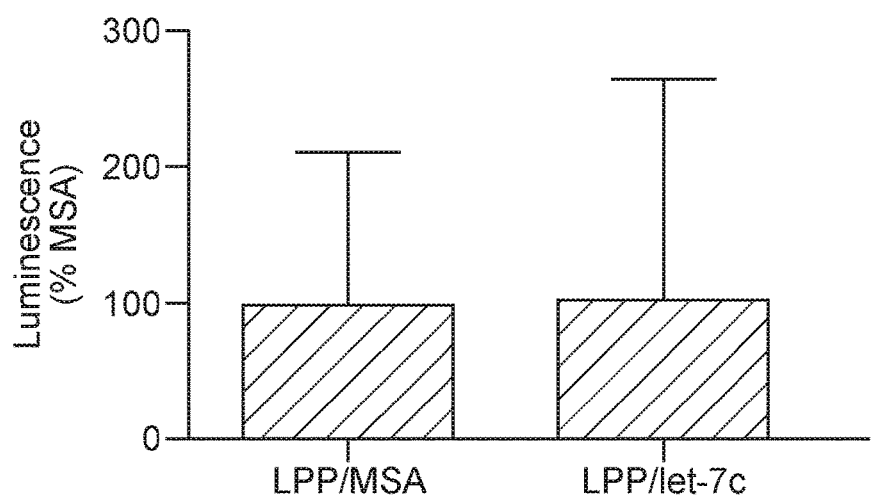
Figure 12B:
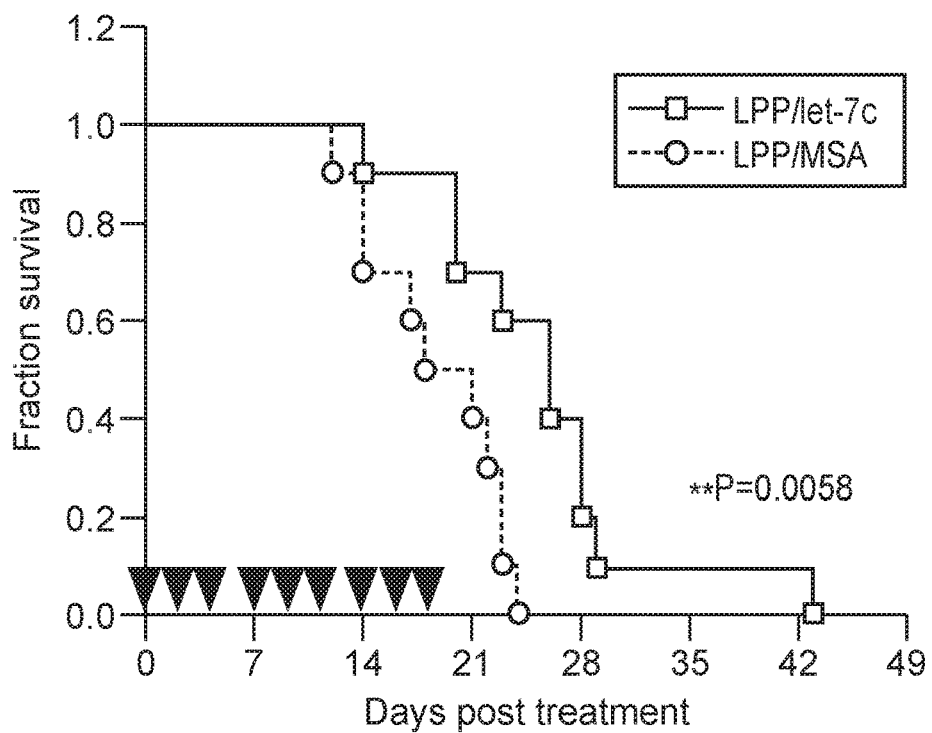
Figure 12C:
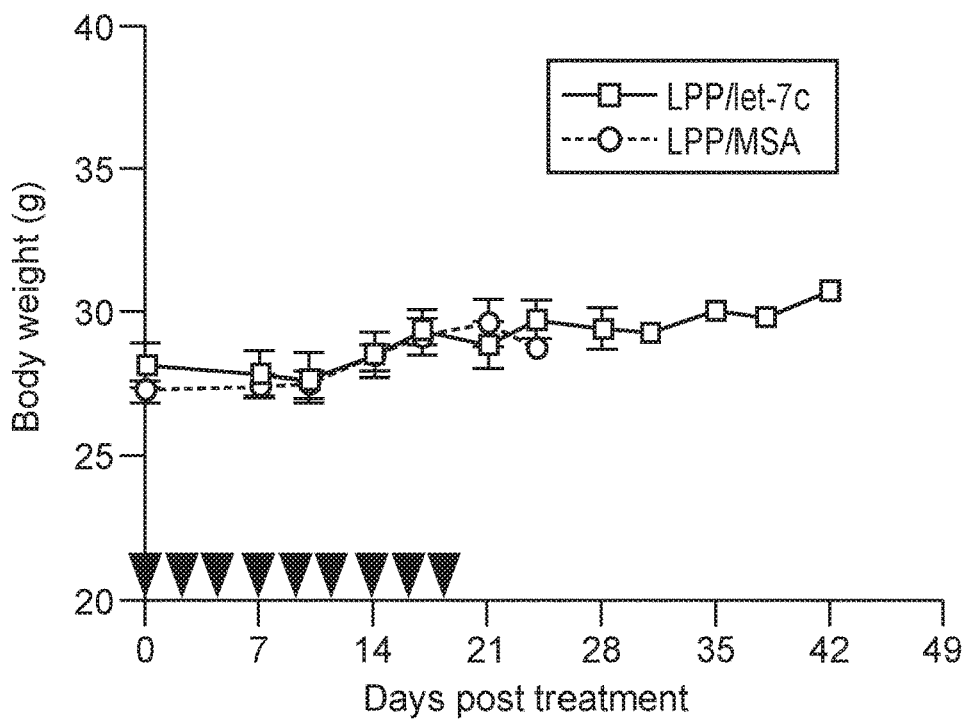

A separate cohort of orthotopic HCC Huh7 xenograft mice was further produced to define the magnitude of benefit of LPP/let-7c nanotherapeutics on overall survival. After the development of HCC was confirmed by quantitative bioluminescence imaging of live mice, subjects showing the same degrees of tumor burden were randomized for LPP/let-7c and control LPP/MSA treatments (FIG. 12A). Survival analysis showed that, compared to LPP/MSA, LPP/let-7c therapy significantly improved overall survival of HCC tumor-bearing mice (FIG. 12B). This was also indicated by a longer median survival of LPP/let-7c-treated mice (26.0 days) than LPP/MSA controls (19.5 days). In agreement with the safety profiles of let-7c treatment in the other therapy study (FIG. 11), LPP/let-7c treatment did not alter mouse body weights compared to LPP/MSA (FIG. 12C).

LPP/Let-7c Produces No or Minimal Immunogenicity in Human PBMCs and Immunocompetent Mice.

Figure 13A:
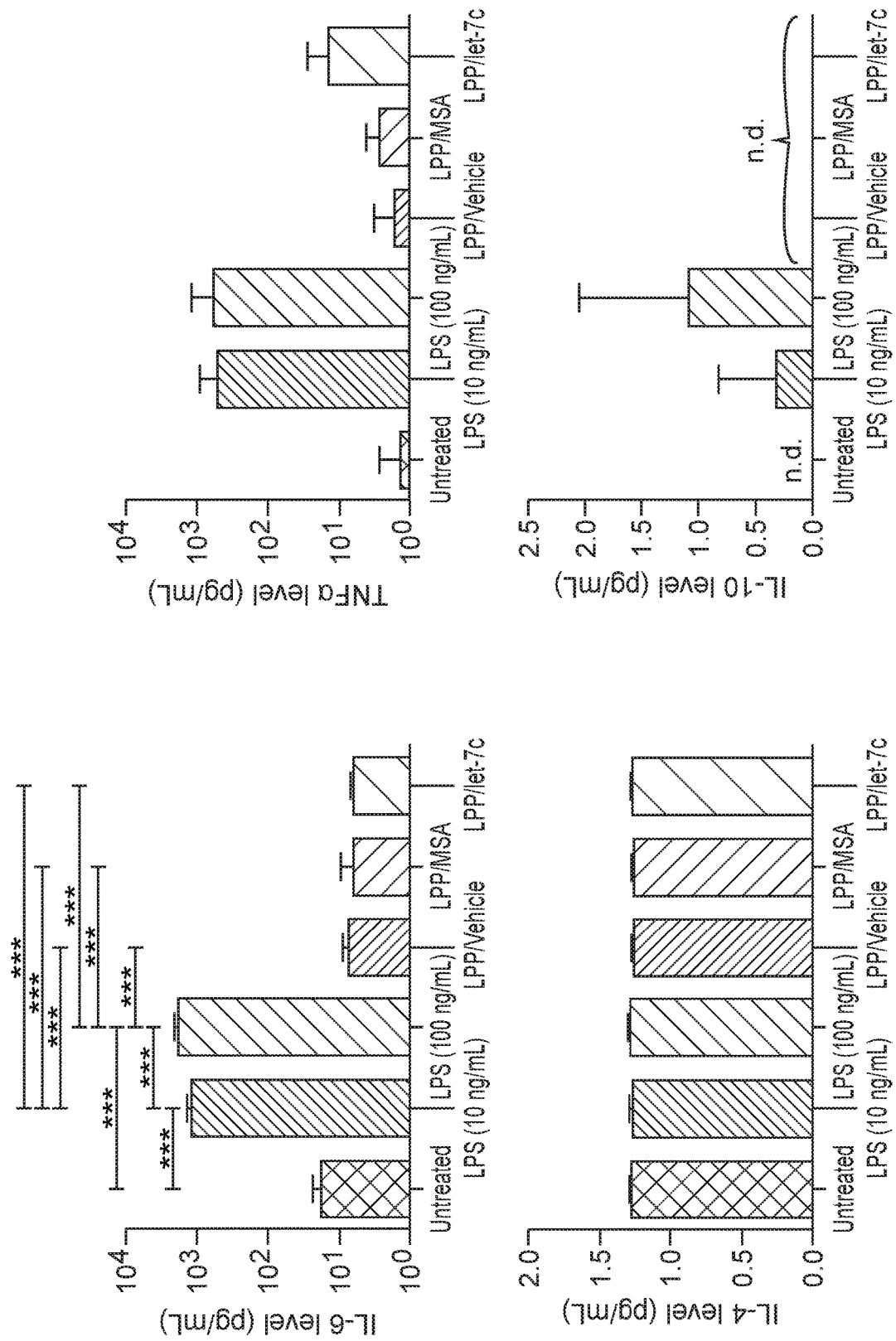
Figure 14A:
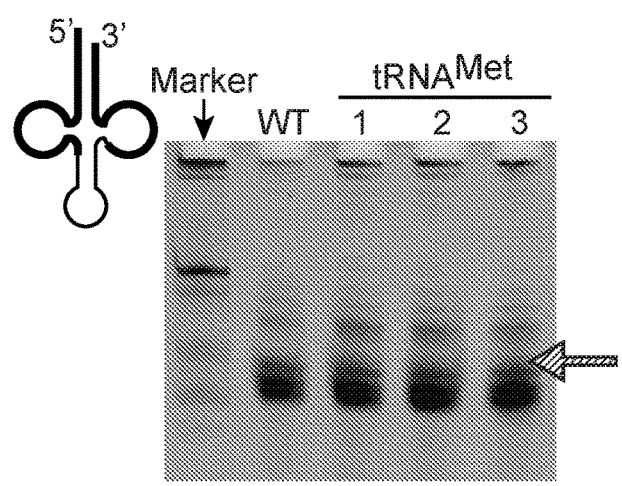
FIGS. 14 A-F illustrate bioengineering hybrid tRNA-pre-miRNA molecules. (A) tRNA standalone showed no expression in E. coli, whereas (B) the fusion of a Sephadex aptamer (SepApm) led to an overexpression of resulting MSA. (C) Human pre-miR-34a itself showed relatively lower-level expression (<3% of total RNA) in E. coli and chimeric MSA/mir-34a was overexpressed (10-20% of total RNA). (D) The pre-miRNA (e.g., pre-miR-34a) could be refined towards a more stable structure to achieve much higher-level expression (>30% of total RNA), independent on SephApm. Use of a human tRNA specie (htRNA) retained or offered even higher-level expression (30-80% of total RNA). (E) Replacing miRNA duplex with miRNA/siRNA/asRNA/sRNA/RNA fragment of interest and/or inserting an aptamer permitted the production of target fully-humanized bioengineered RNA agent (hBERA). (F) Assembling another pre-miRNA for multi-targeting was also accomplished.
Figure 14B:
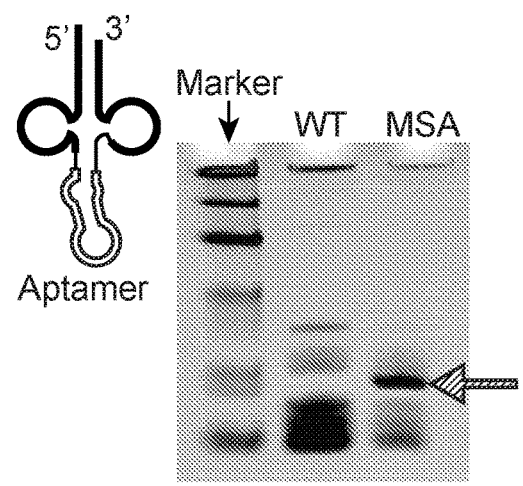
Figure 14C:
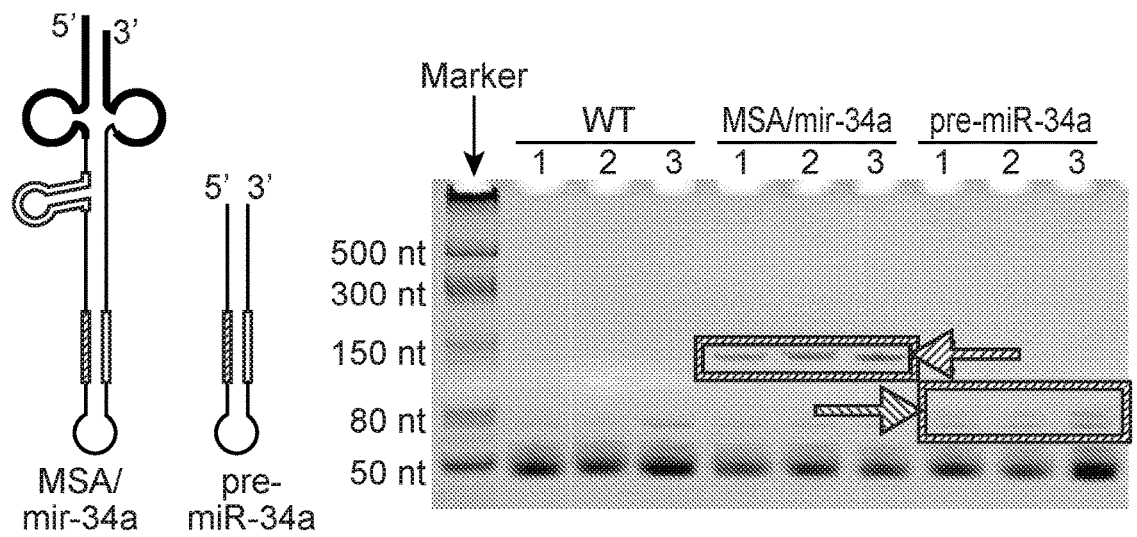
Figure 14D:
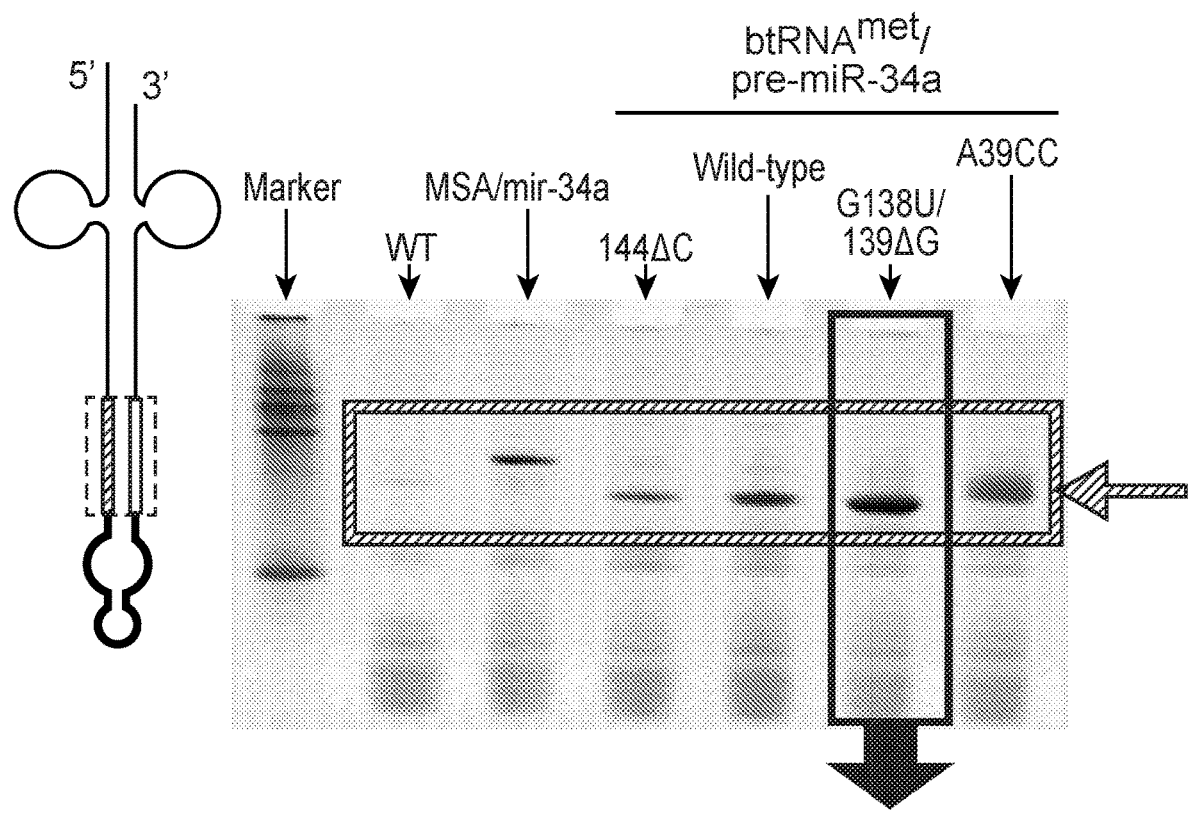
Figure 14D:
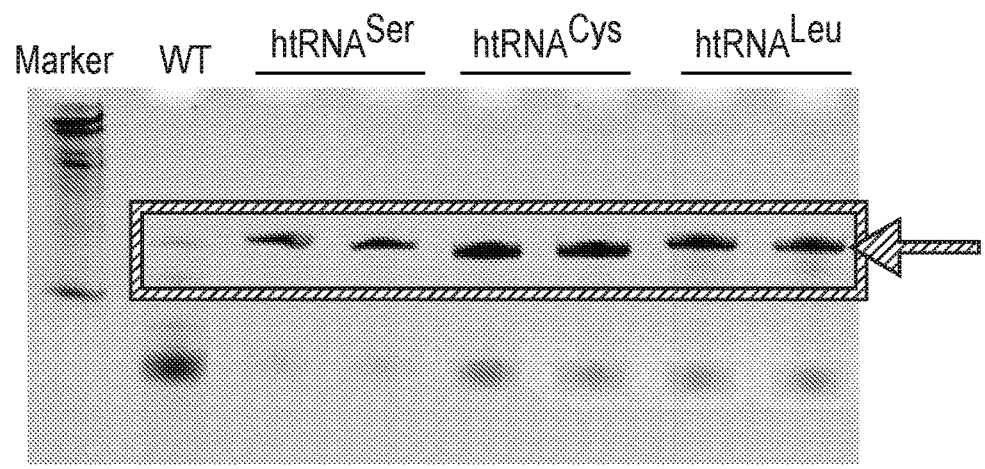
Figure 14E:
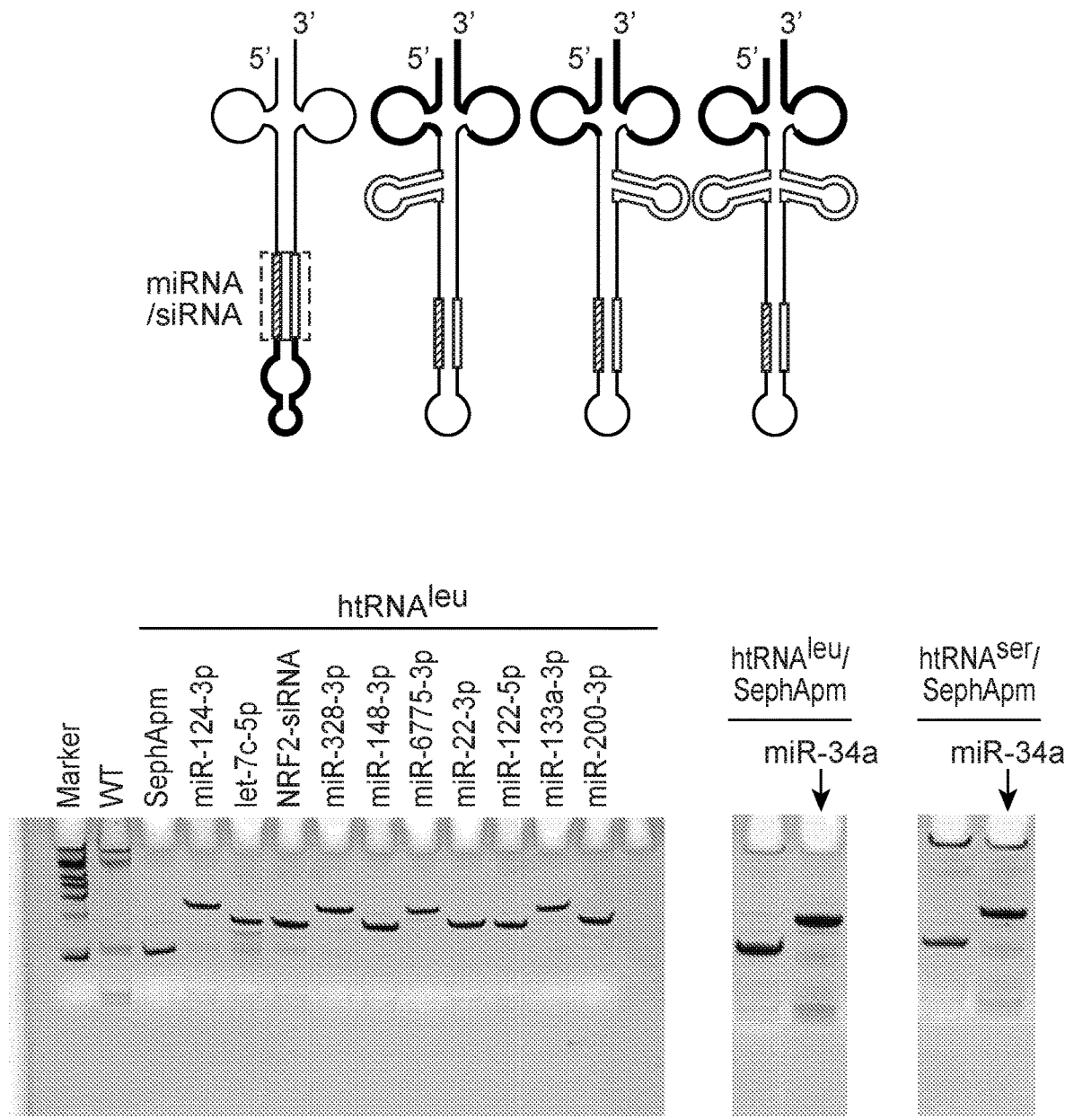
Figure 14F:
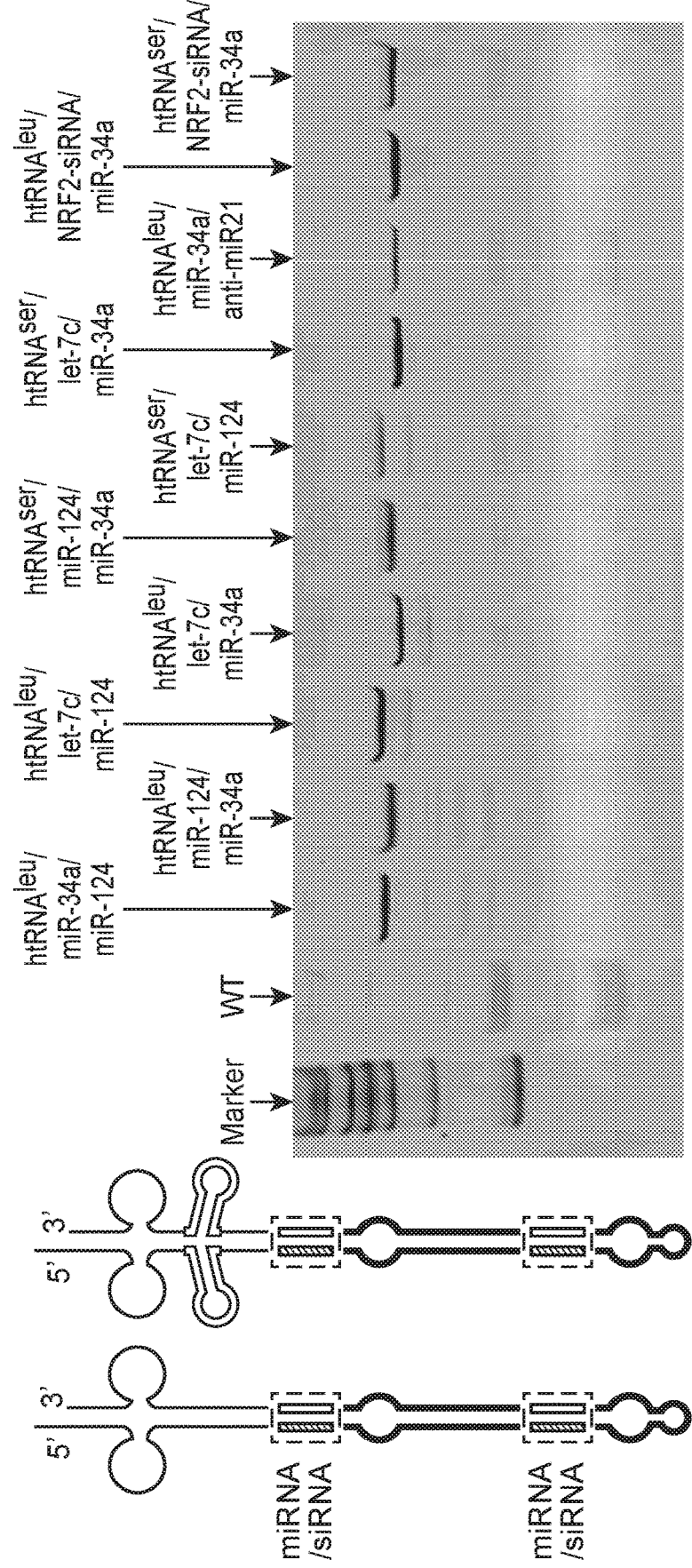
Figure 15A:
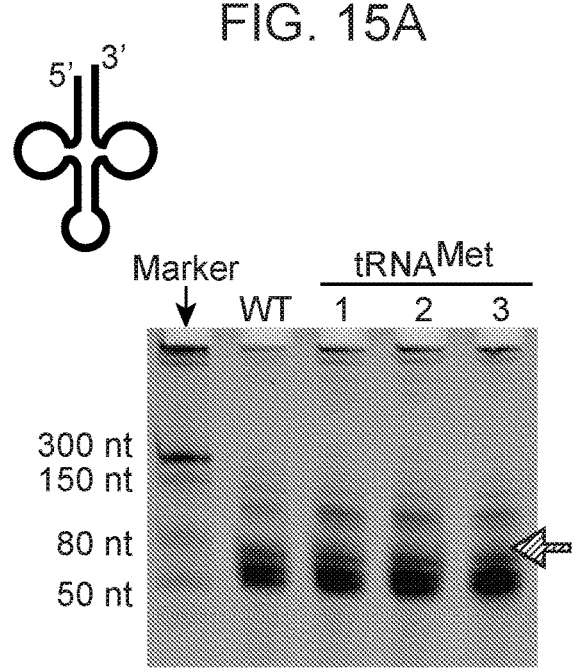
FIGS. 15A-D further illustrate bioengineering of hybrid tRNA-pre-miRNA molecules. Nucleotide sequences shown from Top to Bottom: SEQ ID NO:74, SEQ ID NO:75, SEQ ID NO:76, SEQ ID NO:77, SEQ ID NO:76, SEQ ID NO:78, SEQ ID NO:76, SEQ ID NO:79, SEQ ID NO:80, SEQ ID NO:81, SEQ ID NO:82, SEQ ID NO:83, SEQ ID NO:84, SEQ ID NO:85, SEQ ID NO:84, SEQ ID NO:86, SEQ ID NO:87, and SEQ ID NO:85.
Figure 15B:
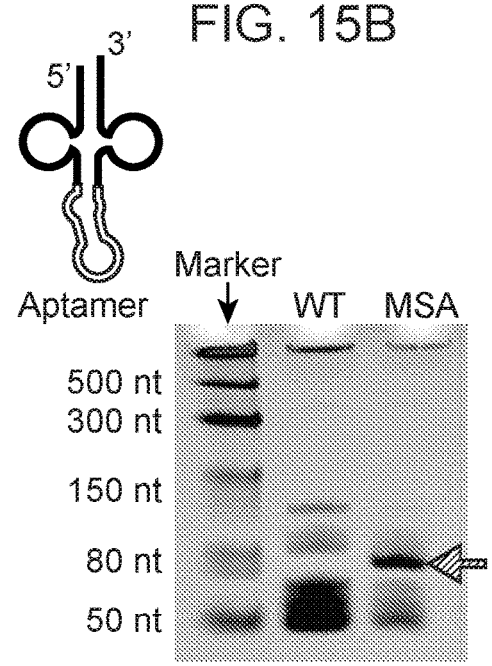
Figure 15C:
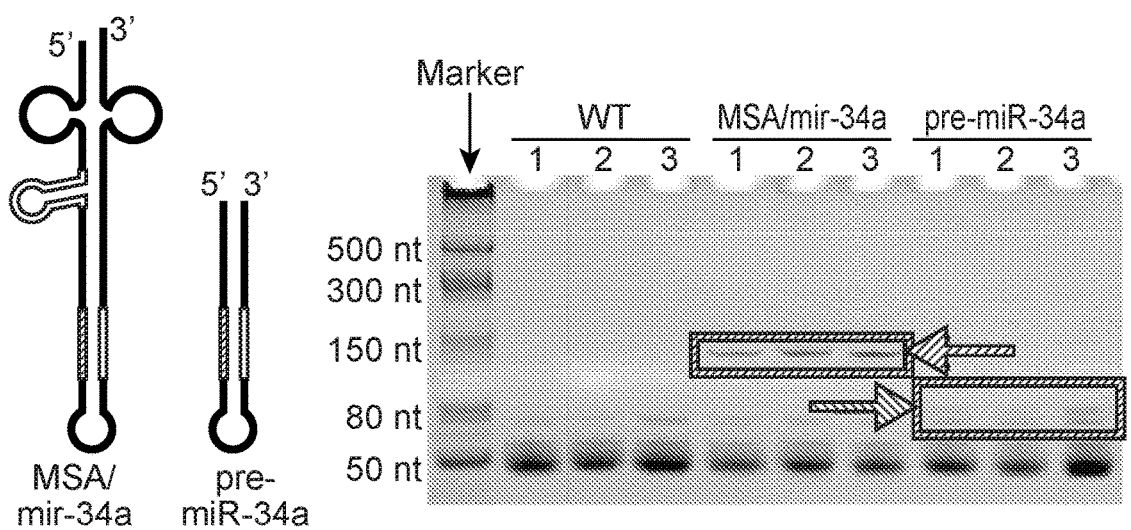
Figure 15D:
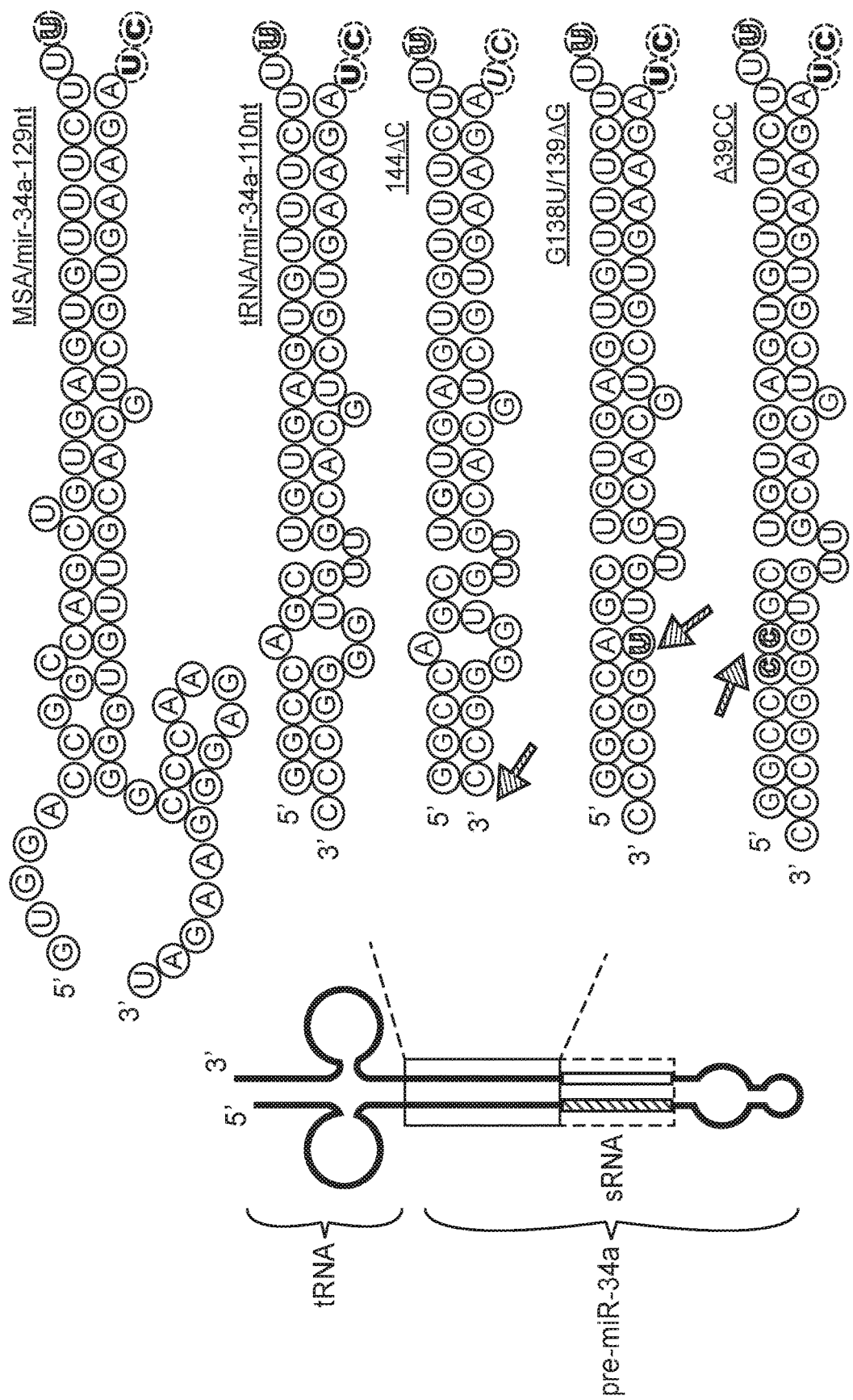
Figure 15D:
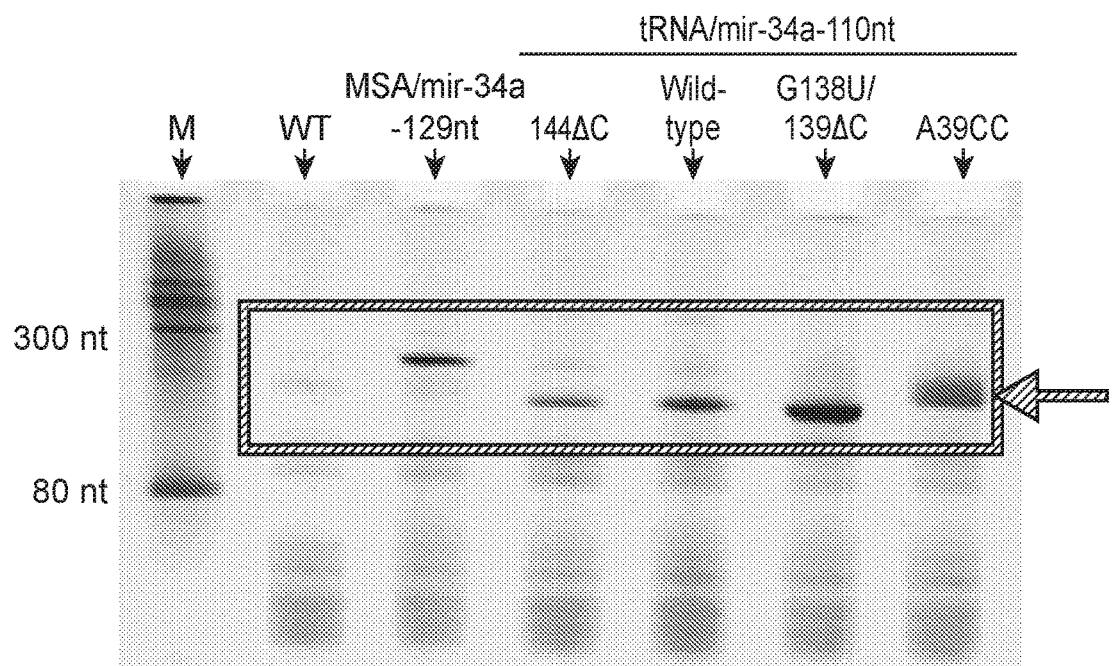
Figure 15D:
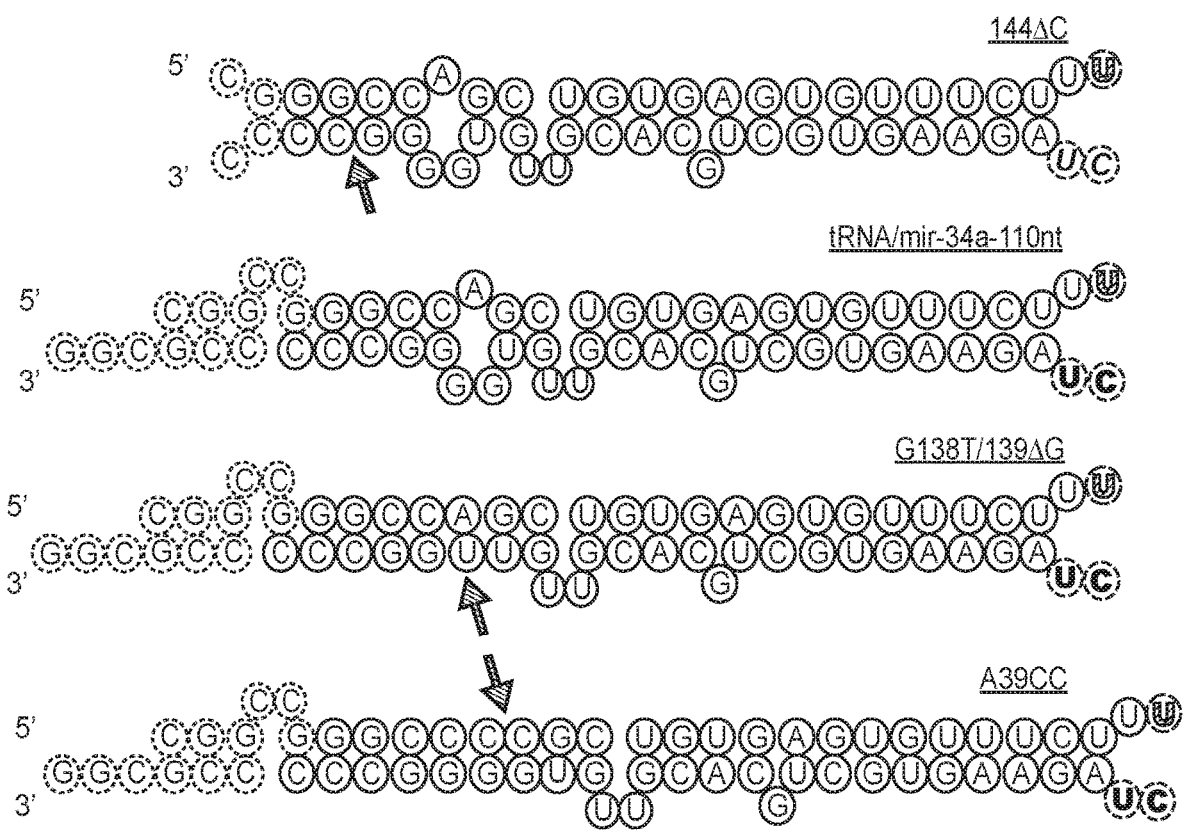

Lastly we assessed if LPP/let-7c nanotherapeutics induces any immune response in human PBMCs and two different strains of healthy immunocompetent mice (Balb/c and CD-1). As expected, LPS treatment provoked a cytokine release syndrome in both human PBMCs (FIG. 13A) and Balb/c (FIG. 13B) and CD-1 (FIG. 13C) mice, as indicated by a significantly sharp elevation of IL-6 levels as well as increase in TNFα and IL-10 levels. By contrast, LPP/let-7c treatment did not alter the levels of IL-6, IL-4 or IL-10 in human PBMCs while it slighted increased TNFα level that is not statistically significant different from untreated cells. Although LPP/vehicle, LPP/MSA and LPP/let-7c all caused a mild increase in serum IL-6 levels in Balb/c and CD-1 mice, the elevated IL-6 levels were still significantly, two to three orders of magnitude lower than those induced by LPS. These results suggest that LPP/let-7c is not immunogenic.

Discussion miRNA replacement therapy represents a novel promising strategy for the control of tumor progression given the findings on a loss of expression/function of tumor suppressive miRNAs in cancerous cells. However, due to the complexity in dysregulation of miRNAs as well as other regulatory factors and pathways, reintroduction of functional miRNAs may not necessarily coincide with optimal efficacy. As such, while miR-122 is the most abundant hepatic miRNA and a number of miRNAs are associated with HCC progression, we found that bioengineered let-7c showed the highest antiproliferative activity against HCC cells among a small collection of ncRNA agents including miR-122. Although the in vivo efficacy of other miRNAs is not compared with let-7c herein, this screening method is predictive of potential benefits of let-7c in relieving HCC tumor burden and improving overall survival revealed in this study.

Current miRNA research and drug development primarily uses miRNA mimics synthesized in test tubes, which are comprised of extensive chemical modifications expected to improve metabolic stability and display more favorable pharmacokinetic properties. However, such synthetic miRNA agents or oligonucleotides from different manufacturers are widely variable in terms of the types, positions and degrees of artificial modifications. These miRNA agents, which are thought to retain "the same sequences", are literally different molecules and inevitably have distinct secondary and higher-order structures as well as physicochemical and biological activities. Moreover, synthetic RNA agents pose high risk of the induction of cytokine release syndrome (34-36). This is also in sharp contrast to protein research and therapy that is proven successful by using recombinant proteins produced and folded in living cells rather than synthetic polypeptides/proteins. Bioengineered miRNA molecules presented in this study represent a novel class of biologic miRNA agents, which are folded and tolerated in living cells and thus may better capture the properties of cellular RNA macromolecules (22). With minimal natural modifications and exhibiting favorable stability in human cells (23, 37), recombinant miRNA agents are selectively processed to target mature miRNAs that rewrite cellular miRNome profile and execute regulatory functions (21).

The pleiotropic nature of miRNA-controlled gene regulation behind cancer cellular processes warrants extensive validation. The interplay between LIN28 and let-7 family miRNAs (33, 38) is a critical component in the regulation of pluripotency as well as HCC and other liver diseases (39). LIN28 that has been shown to be upregulated in stem-like cells can reprogram cells into an undifferentiated state (40) and thus LIN28 may be a druggable target for the suppression of CSCs and tumor initiation. By contrast, LIN28-regulatory let-7 family miRNAs shown to inhibit pluripotency and favor differentiation may be employed to manage CSC maintenance and replication (41, 42). This study demonstrated a consistent action of bioengineered let-7c agent in the inhibition of tumorsphere growth, which is likely attributable to the strong suppression of LIN28B expression in Huh7 cells, and provides an explanation for the greater sensitivity of Huh7 cells to let-7c agent over Sk-Hep-1 cells. Moreover, induction of apoptosis is a common mechanism of antineoplastic agents, and resistance to apoptosis is a common feature of CSCs. let-7 family miRNAs have also been shown to either induce or sensitize cells to apoptosis via attenuation of anti-apoptotic proteins, including Bcl-xl (32, 43). In this study, we found the suppression of Bcl-xl expression by let-7c in both HCC cell lines, which is consistent with the induction of apoptotic, but not necrotic cell populations by a low dose of let-7c.

RNA drugs for systemic administration currently under clinical investigation are mainly delivered by lipid-based systems (e.g., liposomes), given their excellent biocompatibility and favorable lipid composition (44-46). As an example, a Phase I trial is underway to evaluate a small activating, double stranded RNA targeting the transcription factor C/EBP-α formulated in SMARTICLES® liposomal nanoparticle for advanced HCC (https://clinicaltrials.gov/ct2/show/NCT02716012). Among lipid-based delivery systems, LPPs convey the favorable properties of both liposomes and polyplexes (28, 29, 47). Our recent studies have demonstrated that IPEI is able to deliver biologic RNAs to livers to achieve target gene knockdown (20) as well as tumor tissues to control disease (21, 24, 26) in a whole body system. In the present study, we identified an improvement of serum stability for let-7c formulated in LPP nanocomplex as compared to IPEI, owing to the outer PEGylated lipid coating of polyplex. As a result, LPP showed high in vitro delivery efficiency in HCC cell lines. Most importantly, LPP/let-7c provided significantly greater extent suppression of orthotopic HCC tumor burden in vivo, consistently indicated by multiple independent endpoints including live animal luciferase bioluminescent signal, ex vivo GFP intensity, serum AFP level, and histological tumor area. In addition, we revealed that LPP/let-7c nanotherapeutics significantly improved the median survival of orthotopic HCC mice by 6.5-day, which seems to be small. However, considering the difference in lifespans between mice and humans and their possible correlation (48), this would be equivalent to an approximately 9-month extension of survival benefit for HCC patients, which warrants clinical investigation.

Consistent with our previous findings (23), current study demonstrated that highly-purified low-endotoxin recombinant RNAs were well tolerated in HCC tumor-bearing immunodeficient mice and caused no or minimal degree of cytokine release in immunocompetent mice. Interestingly, serum bilirubin level, an indicator of liver damage, fell within normal range in let-7c-treated mice only. This is likely attributable to the effectiveness of let-7c therapy in the control of HCC tumor growth, leading to the suppression of further liver damage, which highlights the aggressive nature of this HCC model (49). Moreover, the present study showed for the first time that bioengineered RNAs are not immunogenic in human PBMCs, an addition to the safety profile of recombinant miRNA molecules produced in living cells.

In conclusion, demonstrated herein is the efficacy of LPP/let-7c nanotherapeutics in an aggressive HCC tumor mouse model, showing no or minimal immunogenicity in mice and human PBMCs. The first-of-a-kind biologic let-7c agent was identified as the most potent among a small set of miRNAs in inhibiting HCC cell viability via interference of specific targets and critical cell functions. Our findings suggest that LPP-formulated biologic let-7c may serve as an effective and safe treatment for HCC which deserves clinical verification.

Further details regarding the present Examples section may be found in Jilek et al. (2019) Molecular Therapy: Nucleic Acids 14:498-508, the disclosure of which is incorporated herein by reference in its entirety for all purposes.

REFERENCES

1. Siegel R L, Miller K D, Jemal A. Cancer statistics, 2018. CA Cancer J Clin 2018; 68:7-30.
2. Kim N G, Nguyen P P, Dang H, Kumari R, Garcia G, Esquivel C O, Nguyen M H. Temporal trends in disease presentation and survival of patients with hepatocellular carcinoma: A real-world experience from 1998 to 2015. Cancer 2018.
3. Sun W, Cabrera R. Systemic Treatment of Patients with Advanced, Unresectable Hepatocellular Carcinoma: Emergence of Therapies. J Gastrointest Cancer 2018.
4. Gbolahan O B, Schacht M A, Beckley E W, LaRoche T P, O'Neil B H, Pyko M. Locoregional and systemic therapy for hepatocellular carcinoma. J Gastrointest Oncol 2017; 8:215-228.
5. Galle P R, Tovoli F, Foerster F, Worns M A, Cucchetti A, Bolondi L. The treatment of intermediate stage tumours beyond TACE: From surgery to systemic therapy. J Hepatol 2017; 67:173-183.
6. Llovet J M, Ricci S, Mazzaferro V, Hilgard P, Gane E, Blanc J F, de Oliveira A C, et al. Sorafenib in advanced hepatocellular carcinoma. N Engl J Med 2008; 359:378-390.
7. Bruix J, Qin S, Merle P, Granito A, Huang Y H, Bodoky G, Pracht M, et al. Regorafenib for patients with hepatocellular carcinoma who progressed on sorafenib treatment (RESORCE): a randomised, double-blind, placebo-controlled, phase 3 trial. Lancet 2017; 389:56-66.
8. Inarrairaegui M, Melero I, Sangro B. Immunotherapy of Hepatocellular Carcinoma: Facts and Hopes. Clin Cancer Res 2018; 24:1518-1524.
9. Torre L A, Siegel R L, Ward E M, Jemal A. Global Cancer Incidence and Mortality Rates and Trends—An Update. Cancer Epidemiol Biomarkers Prev 2016; 25:16-27.
10. Ambros V. The functions of animal microRNAs. Nature 2004; 431:350-355.
11. Bader A G, Brown D, Winkler M. The promise of microRNA replacement therapy. Cancer Res 2010; 70:7027-7030.
12. Rupaimoole R, Slack F J. MicroRNA therapeutics: towards a new era for the management of cancer and other diseases. Nat Rev Drug Discov 2017; 16:203-222.

13. Yu A M, Tian Y, Tu M J, Ho P Y, Jilek J L. MicroRNA Pharmacoepigenetics: Posttranscriptional Regulation Mechanisms behind Variable Drug Disposition and Strategy to Develop More Effective Therapy. Drug Metab Dispos 2016; 44:308-319.
14. Kota J, Chivukula R R, O'Donnell K A, Wentzel E A, Montgomery C L, Hwang H W, Chang T C, et al. Therapeutic microRNA Delivery Suppresses Tumorigenesis in a Murine Liver Cancer Model. Cell 2009; 137: 1005-1017.
15. Fu X, Rivera A, Tao L, De Geest B, Zhang X. Construction of an oncolytic herpes simplex virus that precisely targets hepatocellular carcinoma cells. Mol Ther 2012; 20:339-346.
16. Sandbothe M, Buurman R, Reich N, Greiwe L, Vajen B, Gurlevik E, Schaffer V, et al. The microRNA-449 family inhibits TGF-beta-mediated liver cancer cell migration by targeting SOX4. J Hepatol 2017; 66:1012-1021.
17. Wu H, Tao J, Li X, Zhang T, Zhao L, Wang Y, Zhang L, et al. MicroRNA-206 prevents the pathogenesis of hepatocellular carcinoma by modulating expression of met proto-oncogene and cyclin-dependent kinase 6 in mice. Hepatology 2017; 66:1952-1967.
18. Zhang J, Yang Y, Yang T, Yuan S, Wang R, Pan Z, Yang Y, et al. Double-negative feedback loop between microRNA-422a and forkhead box (FOX)G1/Q1/E1 regulates hepatocellular carcinoma tumor growth and metastasis. Hepatology 2015; 61:561-573.
19. Lu Y, Yue X, Cui Y, Zhang J, Wang K. MicroRNA-124 suppresses growth of human hepatocellular carcinoma by targeting STATS. Biochem Biophys Res Commun 2013; 441:873-879.
20. Chen Q X, Wang W P, Zeng S, Urayama S, Yu A M. A general approach to high-yield biosynthesis of chimeric RNAs bearing various types of functional small RNAs for broad applications. Nucleic Acids Res 2015; 43:3857-3869.
21. Ho P Y, Duan Z, Batra N, Jilek J L, Tu M J, Qiu J X, Hu Z, et al. Bioengineered ncRNAs selectively change cellular miRNome profiles for cancer therapy. J Pharmacol Exp Ther 2018.
22. Ho P Y, Yu A M. Bioengineering of noncoding RNAs for research agents and therapeutics. Wiley Interdisciplinary Reviews: RNA 2016; 7:186-197.
23. Wang W P, Ho P Y, Chen Q X, Addepalli B, Limbach P A, Li M M, Wu W J, et al. Bioengineering Novel Chimeric microRNA-34a for Prodrug Cancer Therapy: High-Yield Expression and Purification, and Structural and Functional Characterization. Journal Of Pharmacology And Experimental Therapeutics 2015; 354:131-141.
24. Jian C, Tu M J, Ho P Y, Duan Z, Zhang Q, Qiu J X, DeVere White R W, et al. Co-targeting of DNA, RNA, and protein molecules provides optimal outcomes for treating osteosarcoma and pulmonary metastasis in spontaneous and experimental metastasis mouse models. Oncotarget 2017; 8:30742-30755.
25. Li P C, Tu M J, Ho P Y, Jilek J L, Duan Z, Zhang Q Y, Yu A X, et al. Bioengineered NRF2-siRNA Is Effective to Interfere with NRF2 Pathways and Improve Chemosensitivity of Human Cancer Cells. Drug Metab Dispos 2018; 46:2-10.
26. Zhao Y, Tu M J, Yu Y F, Wang W P, Chen Q X, Qiu J X, Yu A X, et al. Combination therapy with bioengineered miR-34a prodrug and doxorubicin synergistically suppresses osteosarcoma growth. Biochem Pharmacol 2015; 98:602-613.
27. Lv H T, Zhang S B, Wang B, Cui S H, Yan J. Toxicity of cationic lipids and cationic polymers in gene delivery. Journal Of Controlled Release 2006; 114:100-109.
28. Rezaee M, Oskuee R K, Nassirli H, Malaekeh-Nikouei B. Progress in the development of lipopolyplexes as efficient non-viral gene delivery systems. Journal Of Controlled Release 2016; 236:1-14.
29. Ewe A, Panchal O, Pinnapireddy S R, Bakowsky U, Przybylski S, Temme A, Aigner A. Liposome-polyethylenimine complexes (DPPC-PEI lipopolyplexes) for therapeutic siRNA delivery in vivo. Nanomedicine 2017; 13:209-218.
30. Schafer J, Hobel S, Bakowsky U, Aigner A. Liposome-polyethylenimine complexes for enhanced DNA and siRNA delivery. Biomaterials 2010; 31:6892-6900.
31. Ewe A, Schaper A, Barnert S, Schubert R, Temme A, Bakowsky U, Aigner A. Storage stability of optimal liposome-polyethylenimine complexes (lipopolyplexes) for DNA or siRNA delivery. Acta biomaterialia 2014; 10:2663-2673.
32. Shimizu S, Takehara T, Hikita H, Kodama T, Miyagi T, Hosui A, Tatsumi T, et al. The let-7 family of microRNAs inhibits Bcl-xL expression and potentiates sorafenib-induced apoptosis in human hepatocellular carcinoma. Journal of hepatology 2010; 52:698-704.
33. Nam Y, Chen C, Gregory R I, Chou J J, Sliz P. Molecular basis for interaction of let-7 microRNAs with Lin28. Cell 2011; 147:1080-1091.
34. Robbins M, Judge A, MacLachlan I. siRNA and innate immunity. Oligonucleotides 2009; 19:89-102.
35. Yu H, Wang Z, Sun G, Yu Y. Recognition of nucleic acid ligands by toll-like receptors 7/8: importance of chemical modification. Curr Med Chem 2012; 19:1365-1377.
36. Bramsen J B, Kjems J. Development of Therapeutic-Grade Small Interfering RNAs by Chemical Engineering. Front Genet 2012; 3:154.
37. Li M-M, Addepalli B, Tu M-J, Chen Q-X, Wang W-P, Limbach P A, LaSalle J M, et al. Chimeric microRNA-1291 biosynthesized efficiently in *Escherichia coli* is effective to reduce target gene expression in human carcinoma cells and improve chemosensitivity. Drug Metabolism and Disposition 2015; 43:1129-1136.
38. Guo Y, Chen Y, Ito H, Watanabe A, Ge X, Kodama T, Aburatani H. Identification and characterization of lin-28 homolog B (LIN28B) in human hepatocellular carcinoma. Gene 2006; 384:51-61.
39. McDaniel K, Hall C, Sato K, Lairmore T, Marzioni M, Glaser S, Meng F, et al. Lin28 and let-7: roles and regulation in liver diseases. Am J Physiol Gastrointest Liver Physiol 2016; 310:G757-765.
40. Yu J, Vodyanik M A, Smuga-Otto K, Antosiewicz-Bourget J, Frane J L, Tian S, Nie J, et al. Induced pluripotent stem cell lines derived from human somatic cells. Science 2007; 318:1917-1920.
41. Reinhart B J, Slack F J, Basson M, Pasquinelli A E, Bettinger J C, Rougvie A E, Horvitz H R, et al. The 21-nucleotide let-7 RNA regulates developmental timing in *Caenorhabditis elegans*. Nature 2000; 403:901-906.
42. Viswanathan S R, Daley G Q. Lin28: A microRNA regulator with a macro role. Cell 2010; 140:445-449.
43. Tian N, Han Z, Li Z, Zhou M, Fan C. Lin28/let-7/Bcl-xL pathway: the underlying mechanism of drug resistance in Hep3B cells. Oncol Rep 2014; 32:1050-1056.
44. Xue H Y, Guo P B, Wen W C, Wong H L. Lipid-Based Nanocarriers for RNA Delivery. Current Pharmaceutical Design 2015; 21:3140-3147.

45. Sullenger B A, Nair S. From the RNA world to the clinic. Science 2016; 352:1417-1420.
46. Kim H J, Kim A, Miyata K, Kataoka K. Recent progress in development of siRNA delivery vehicles for cancer therapy. Advanced Drug Delivery Reviews 2016; 104:61-77.
47. Xia Y, Tian J, Chen X. Effect of surface properties on liposomal siRNA delivery. Biomaterials 2016; 79:56-68.
48. Dutta S, Sengupta P. Men and mice: Relating their ages. Life Sci 2016; 152:244-248.
49. Carr B I, Guerra V, Giannini E G, Farinati F, Ciccarese F, Rapaccini G L, Di Marco M, et al. Association of abnormal plasma bilirubin with aggressive hepatocellular carcinoma phenotype. In: Seminars in oncology; 2014: Elsevier; 2014. p. 252-258.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polynucleotide comprising a tRNA operably linked to pre-microRNA 34a (pre-miRNA-34a), wherein the tRNA and/or pre-miRNA-34a are operably linked to an inserted let-7 RNA molecule that inhibits the growth or proliferation of a hepatocellular carcinoma (HCC) cell, and wherein the polynucleotide comprises a sequence having at least 90% sequence identity to a sequence selected from the group consisting of SEQ ID NOs: 12-17.

2. The polynucleotide of claim 1, wherein all or part of the stem-loop anticodon of the tRNA is replaced with the pre-miRNA.

3. The polynucleotide of claim 1, wherein the inserted let-7 RNA molecule is inserted at, abutted with, or operably linked to:
   a) the 5' end of the pre-miRNA;
   b) the 3' end of the pre-miRNA;
   c) 5' of a dicer or RNase cleavage site of the pre-miRNA; or
   d) 3' of a dicer or RNase cleavage site of the pre-miRNA.

4. The polynucleotide of claim 1, wherein the inserted let-7 RNA molecule prevents, reduces or inhibits the expression of a target polypeptide in an HCC cell.

5. The polynucleotide of claim 1, wherein the inserted let-7 RNA molecule is a mature let-7c miRNA.

6. The polynucleotide of claim 1, wherein the tRNA is a mammalian tRNA.

7. The polynucleotide of claim 1, wherein the tRNA has a nucleic acid sequence having at least 90% sequence identity to one of SEQ ID NOs:47-64.

8. An expression cassette comprising the polynucleotide of claim 1.

9. A liposome or a nanoparticle comprising the polynucleotide of claim 1.

10. The liposome or nanoparticle of claim 9, which is a liposome comprising an inner core comprising the polynucleotide complexed with a polyethylenimine (PEI) and an outer lipid bilayer.

11. The liposome or nanoparticle of claim 9, which is a liposome comprising an outer lipid bilayer comprising a mixture of 1,2-di-O-octadecenyl-3-trimethylammonium propane (DOTMA), cholesterol and 1,2-Dimyristoyl-sn-glycerol, methoxypolyethylene glycol (DMG-PEG2000).

12. A non-human host cell transfected or transformed with the polynucleotide of claim 1.

13. A composition, comprising:
   the polynucleotide of claim 1; and
   a pharmaceutically acceptable carrier.

14. A kit, comprising:
   the polynucleotide of claim 1; and
   instructions for administering the polynucleotide to a subject having hepatocellular carcinoma (HCC).

15. A method of inhibiting the growth, proliferation, and/or progression of hepatocellular carcinoma (HCC) in a subject in need thereof, comprising administering to the subject an effective amount of the polynucleotide of claim 1.

16. The method according to claim 15, wherein the polynucleotide is administered intravenously, intraarterially, intraperitoneally, intrahepatically, subcutaneously, or intratumorally.

17. The method according to claim 15, wherein the subject is tested for the overexpression or underexpression of one or more miRNAs prior to administration.

* * * * *